(12) United States Patent
Taylor et al.

(10) Patent No.: US 10,308,638 B2
(45) Date of Patent: Jun. 4, 2019

(54) SELECTIVE ALPHA-7 NICOTINIC RECEPTOR AGONISTS AND METHODS FOR MAKING AND USING THEM

(71) Applicants: The Regents of the University of California, Oakland, CA (US); The Scripps Research Institute, La Jolla, CA (US)

(72) Inventors: Palmer Taylor, La Jolla, CA (US); Gisela-Andrea Camacho-Hernandez, La Jolla, CA (US); Karl Barry Sharpless, La Jolla, CA (US); M. G. Finn, La Jolla, CA (US); Valery Fokin, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/558,986

(22) PCT Filed: Mar. 24, 2016

(86) PCT No.: PCT/US2016/024008
§ 371 (c)(1),
(2) Date: Sep. 15, 2017

(87) PCT Pub. No.: WO2016/154434
PCT Pub. Date: Sep. 29, 2016

(65) Prior Publication Data
US 2018/0244653 A1    Aug. 30, 2018

Related U.S. Application Data

(60) Provisional application No. 62/138,225, filed on Mar. 25, 2015.

(51) Int. Cl.
| | |
|---|---|
| *A61K 31/46* | (2006.01) |
| *A61K 31/439* | (2006.01) |
| *A61K 31/454* | (2006.01) |
| *A61K 31/496* | (2006.01) |
| *C07D 249/06* | (2006.01) |
| *C07D 401/14* | (2006.01) |
| *C07D 403/04* | (2006.01) |
| *C07D 405/04* | (2006.01) |
| *C07D 451/04* | (2006.01) |
| *C07D 451/14* | (2006.01) |
| *C07D 453/02* | (2006.01) |
| *C07D 473/34* | (2006.01) |
| *A61K 31/4192* | (2006.01) |
| *A61K 31/5377* | (2006.01) |
| *A61K 31/55* | (2006.01) |

(52) U.S. Cl.
CPC ........ *C07D 403/04* (2013.01); *A61K 31/4192* (2013.01); *A61K 31/439* (2013.01); *A61K 31/454* (2013.01); *A61K 31/46* (2013.01); *A61K 31/496* (2013.01); *A61K 31/5377* (2013.01); *A61K 31/55* (2013.01); *C07D 249/06* (2013.01); *C07D 401/14* (2013.01); *C07D 405/04* (2013.01); *C07D 451/04* (2013.01); *C07D 451/14* (2013.01); *C07D 453/02* (2013.01); *C07D 473/34* (2013.01)

(58) Field of Classification Search
None
See application file for complete search history.

(56) References Cited

U.S. PATENT DOCUMENTS

| | | |
|---|---|---|
| 2008/0103170 A1 | 5/2008 | Jacobs et al. |
| 2010/0234349 A1 | 9/2010 | Olsen et al. |
| 2011/0201656 A1 | 8/2011 | Nardi et al. |

OTHER PUBLICATIONS

Arunrungvichian et al, ACS Chem. Neurosci, 6, 1317-1330, received Feb. 11 (Year: 2015).*
Thomas, International Search Report for PCT/US2016/024008, dated Jun. 10, 2016.
Thomas, Written Opinion for PCT/US2016/024008, dated Jun. 10, 2016.
Bai, International Preliminary Report on Patentability and Written Opinion for PCT/US2016/024008, dated Sep. 26, 2017.

* cited by examiner

*Primary Examiner* — Zinna Northington Davis
(74) *Attorney, Agent, or Firm* — Greer, Burns & Crain, LTD.; Gregory P. Einhorn

(57) ABSTRACT

In alternative embodiments, provided are selective agonists having a high affinity for the alpha7 nicotinic acetylcholine receptor (α7 nAChR), assays for selectivity of nicotinic receptor subtype and ligand-gated ion channel subtype based on receptor occupation and response, behavioral assessments for reversing cognitive impairment after scopolamine treatment, enhancing memory retention over time, pharmaceutical compositions and formulations and devices comprising them, and methods for making and using them, including characterizing and efficiently assaying them for receptor subtype selectivity. In alternative embodiments, provided are substituted anti 1,2,3-triazoles compounds with high affinity, and selective binding, for the alpha7 nicotine acetylcholine receptor (α7 nAChR), as exemplified by 5-(1-(2-(Piperidin-1-yl)ethyl)-1H-1,2,3-triazol-4-yl)-1H-indole ("IND1"), 5-((quinuclid-3-yl)-1H-1,2,3-triazol-4-yl)-1H-indole ("IND8") and 3-(4-hydroxyphenyl-1,2,3-triazol-1-yl) quinuclidine ("QND8"). In alternative embodiments, provided are products of manufacture such as pumps, devices, syringes and the like comprising a compound, pharmaceutical composition or formulation as provided herein.

12 Claims, 36 Drawing Sheets

Step (i)

Step (ii)

FIG. 32

Table 1

| Compound | R | $K_d \pm SD$ (µM) | | Agonist $EC_{50} \pm SD$ (µM) | | Antagonist $K_A \pm SD$ (µM) | |
|---|---|---|---|---|---|---|---|
| | | α7 | α4β2 | 5HT$_{3A}$ | α7 | 5HT$_{3A}$ | α4β2 | 5HT$_{3A}$ |
| TTIn-1[31] | | 4.2 ± 2.8 | >10 | 6.0 ± 0.8 | 0.57 ± 0.20 | - | 2.7 ± 0.4[C] | 6.0 ± 3.7[NC] |
| IND1 | | 0.34 ± 0.13 | >10 | 5.5 ± 1.4 | 0.17 ± 0.05 | >13.3 | >10 | >10 |
| IND2 | | 7.2 ± 1.3 | >10 | 8.2 ± 3.4 | 2.2 ± 0.7 | >13.3 | >10 | >10 |
| IND3 | | 13.8 ± 4.1 | >10 | >10 | 0.91 ± 0.20 | >13.3 | >10 | >10 |
| IND4 | | >10 | >10 | >10 | >13.3 | >13.3 | >10 | >10 |
| IND5 | | >10 | >10 | >10 | >13.3 | >13.3 | >10 | >10 |
| IND6 | | 14.1 ± 0.3 | >10 | >10 | 12.2 ± 3.5 | >13.3 | >10 | >10 |
| IND7 | | 4.5 ± 1.2 | >10 | 22 ± 12 | 1.00 ± 0.33 | >13.3 | 22 ± 7[NC] | >10 |

| Compound | R | $K_d \pm SD$ (µM) | | | Agonist $EC_{50} \pm SD$ (µM) | | Antagonist $K_A \pm SD$ (µM) | |
|---|---|---|---|---|---|---|---|---|
| | | α7 | α4β2 | 5HT$_{3A}$ | α7 | 5HT$_{3A}$ | α4β2 | 5HT$_{3A}$ |
| IND8 | 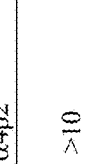 | 0.12 ± 0.06 | 0.75 ± 0.20 | 0.05 ± 0.01 | 0.03 ± 0.01 | 0.21 ± 0.08* | >10 | - |
| IND9 |  | >10 | >10 | >10 | 12.0 ± 1.9 | - | >10 | 4.65 ± 2.01$^C$, 2.98 ± 0.66$^{NC}$ |
| IND10 |  | 3.0 ± 0.2 | >10 | 3.4 ± 0.6 | 0.66 ± 0.16 | - | >10 | 1.01 ± 0.26$^C$, 9.31 ± 5.03$^{NC}$ |
| IND11 | 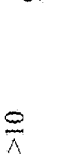 | 5.07 ± 1.37 | >10 | 5.72 ± 1.50 | 3.26 ± 0.74 | >13.3 | >10 | >10 |
| IND12 |  | 7.68 ± 2.99 | >10 | 2.90 ± 0.46 | 5.74 ± 1.06 | - | >10 | 3.21 ± 0.41$^C$, 4.85 ± 1.45$^{NC}$ |
| IND13 |  | 4.84 ± 0.89 | >10 | >10 | 2.17 ± 0.40 | >13.3 | >10 | >10 |
| IND14 |  | 1.N5 ± 0.31 | >10 | 9.32 ± 2.38 | 0.78 ± 0.16 | - | >10 | 2.68 ± 1.09$^C$ |
FIG. 32 (continuation)

| R2 | R1 = [piperidine] | | | | R1 = [quinuclidine] | | |
|---|---|---|---|---|---|---|---|
| | | Kd ± SD (uM) | | | | Kd ± SD (uM) | |
| | | α7 | α4β2 | 5HT3A | | α7 | α4β2 | 5HT3A |
| | PPRD6 | >10 | >10 | >10 | QND6 | 5.58 ± 0.46 | 1.35 ± 0.20 | >10 |
| | PPRD7 | >10 | >10 | >10 | QND7 | >10 | >10 | >10 |
| | PPRD8 | 7.4 ± 1.6 | >10 | >10 | QND8 | 0.08 ± 0.03 | >10 | 0.54 ± 0.05 |
| | PPRD9 | 12.1 ± 1.1 | >10 | >10 | QND9 | 1.90 ± 0.03 | 1.3 ± 0.4 | 0.15 ± 0.03 |
| | PPRD10 | >10 | >10 | >10 | QND10 | >10 | >10 | >10 |
| | PPRD11 | >10 | >10 | 2.6 ± 0.4 | QND11 | 6.7 ± 1.5 | >10 | 0.19 ± 0.09 |
| | PPRD12 | >10 | >10 | >10 | QND12 | 0.92 ± 0.34 | >10 | 0.02 ± 0.00 |
| | PPRD13 | 31.9 ± 10.0 | >10 | 1.9 ± 0.6 | QND13 | 0.36 ± 0.11 | >10 | 0.40 ± 0.06 |
| | PPRD14 | >10 | >10 | >10 | | | | |
| | PPRD15 | 4.4 ± 0.9 | >10 | >10 | QND15 | 3.6 ± 1.3 | >10 | 0.04 ± 0.00 |

FIG. 33 (continuation)

SELECTIVE ALPHA-7 NICOTINIC RECEPTOR AGONISTS AND METHODS FOR MAKING AND USING THEM

RELATED APPLICATIONS

This application is a national phase application claiming benefit of priority under 35 U.S.C. § 371 to International (PCT) Patent Application serial number PCT/US2016/024008, filed Mar. 24, 2016, which claims benefit of priority to U.S. provisional patent application Ser. No. 62/138,225, filed Mar. 25, 2015. The aforementioned applications are expressly incorporated herein by reference in their entirety and for all purposes.

STATEMENT AS TO RIGHTS TO INVENTIONS MADE UNDER FEDERALLY SPONSORED RESEARCH

This invention was made with Government support under GM18360 awarded by the National Institutes of Health. The Government has certain rights in the invention.

TECHNICAL FIELD

This invention generally relates to neurochemistry and medicine. Provided are receptor subtype selective agonists having a high affinity for the alpha7 nicotine acetylcholine receptor ($\alpha$7 nAChR), pharmaceutical compositions and formulations and devices comprising them, and methods for making (synthesizing) and using them. In alternative embodiments, provided are substituted anti 1,2,3-triazoles compounds with high affinity, and selective binding, for the alpha7 nicotine acetylcholine receptor ($\alpha$7 nAChR), as exemplified by 5-(1-(2-(Piperidin-1-yl)ethyl)-1H-1,2,3-triazol-4-yl)-1H-indole ("IND1"). In alternative embodiments, exemplary compounds, such as IND1, are linked through a 1,2,3 triazole, either syn or anti.

BACKGROUND

Nicotinic acetylcholine receptors (nAChRs) are widely distributed in the central and peripheral nervous systems, controlling peripheral voluntary motor, autonomic and central nervous system functions. Since they are found in abundance in presynaptic locations in the CNS, they can control the release of other transmitters. Therefore, they have diverse modulatory functions and are candidate targets for neurologic disorders of development, schizophrenia and autism, and the aging process, Parkinsonism and the Alzheimer dementias,[ref 1-8].

Structurally, nAChRs are members of Cys-loop ligand-gated ion channel (LGIC) superfamily, which are composed of five transmembrane spanning subunits, assembled surrounding a centrosymmetric ion pore.[9] There are at least 12 distinct neuronal subunits ($\alpha$2-$\alpha$10 and $\beta$2-$\beta$4) characterized in mammalian and avian systems.[9,10] The structure of these pentameric receptors is divided into three domains: the N-terminal extracellular, transmembrane, and intracellular domains. Assembly of nAChRs is specific for certain subunit partnerships, and can be categorized in two major assemblies: hetero-pentameric and homo-pentameric. Differences in subunit combinations and localization lead to their functional and pharmacological variances.[9,11,12] The orthosteric ligand binding pocket is located at the interface between a principal (alpha) and a complementary subunit in the extracellular domain.[9,13]

The $\alpha$7-nAChR is unique in being homomeric with identical binding sites formed between its principal, C loop containing face and the opposing face of the neighbor. The $\alpha$7-nAChR is one of the major subtypes localized in cerebral cortex and hippocampus,[12] which are the brain areas accounting for memory and cognition process, resulting in a concerted attempt to discover agonist compounds for this subtype of nAChRs. Accordingly, selective $\alpha$7-nAChR agonists would be very useful for treating conditions involving memory and cognition processes.

Nicotinic receptors that are stimulated by acetylcholine have long been known to modulate neurotransmission in the Central Nervous System by influencing the release of other transmitters or acetylcholine itself from presynaptic sites. Such release relates to transient improvements in cognition, reinforcement of reward, and memory enhancement. The alpha-7 receptor is a prime candidate for influencing cognitive activity and information retention in the form of short term memory. Several disorders of nervous system development and incurring in the ageing process are linked to nicotinic receptor activity. Since there is plethora of nicotinic receptor subtypes, selectivity for subtype becomes critical for achieving the pharmacological action and specificity and for minimizing side effects.

SUMMARY

In alternative embodiments, provided are compounds having one of the following structures or compositions having one or more compounds of the following structures, or equivalents thereof, or a stereoisomer thereof, or an analog thereof, or a pharmaceutically acceptable salt thereof, or a bioisostere thereof; or a composition comprising an isolated or synthetic compound consisting essentially of, or consisting of:

(a) a compound having the formula:

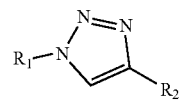

wherein R1 is independently selected from any of the following moieties (1) to (14):

R₁ =

(1)

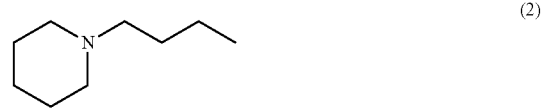

(2)

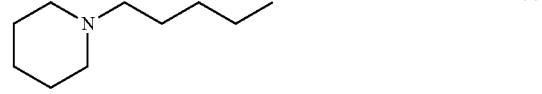

(3)

(4)

-continued
(5)
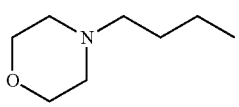
(6)
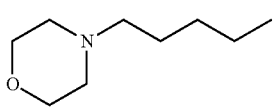
(7)
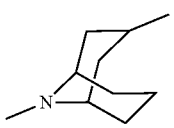
(8)
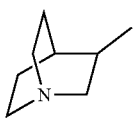
(9)
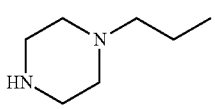
(10)
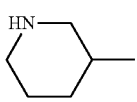
(11)
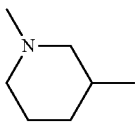
(12)
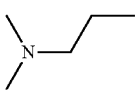
(13)
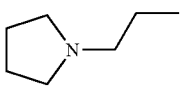
(14)
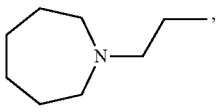
wherein R2 is independently selected from any of the following moieties:
R₂ = (A) Substituted benzene ring
(1)
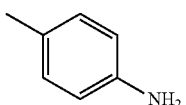
(2)
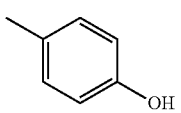
-continued
(3)
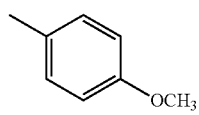
(4)
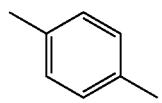
(13)
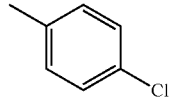
(7)
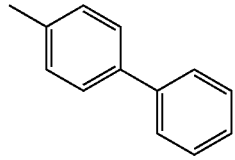
(14)
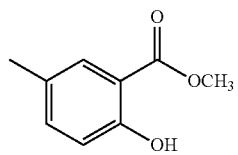
(15)
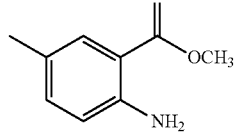
(B) Bicyclic ring
(1)
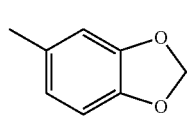
(6)
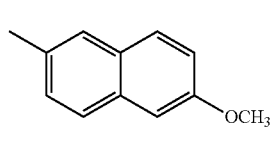
(10)
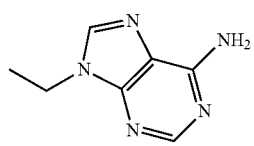
(9)
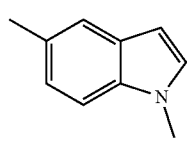
(5)
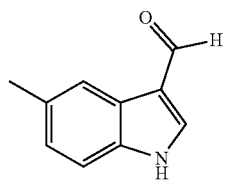

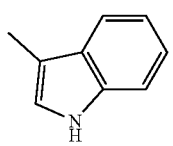
(12)
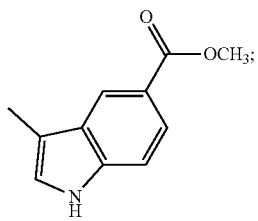
(11)
(b) a compound having the formula:
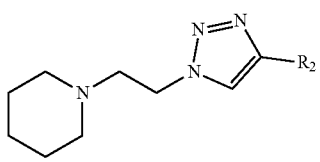
wherein R2 is independently selected from any of the following moieties:
R₂ = (A) Substituted benzene ring
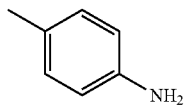
(2)
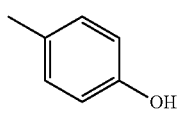
(8)
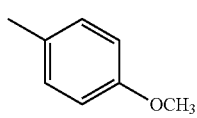
(3)
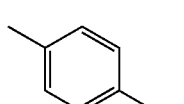
(4)
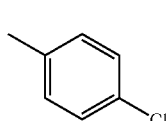
(13)
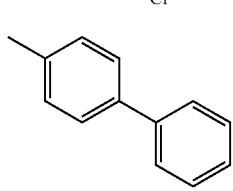
(7)
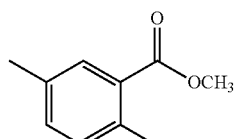
(14)
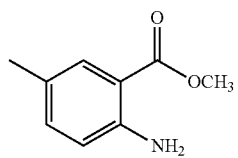
(15)
(B) Bicyclic ring
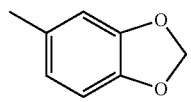
(1)
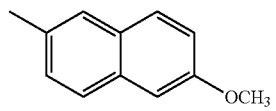
(6)
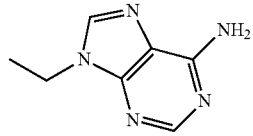
(10)
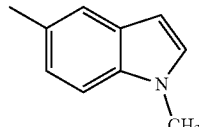
(9)
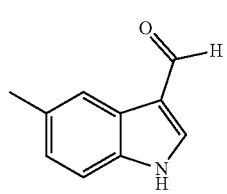
(5)
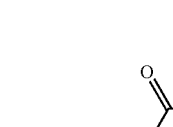
(12)
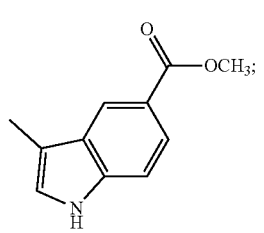
(11)

or
(c) a compound having the formula:
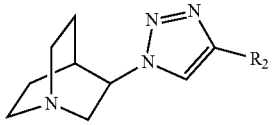
wherein R2 is independently selected from any of the following moieties:
R₂ = (A) Substituted benzene ring
(2)
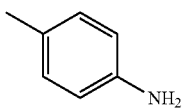
(3)
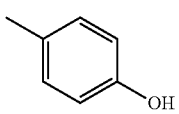
(4)
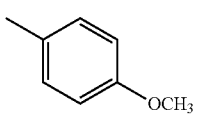
(7)
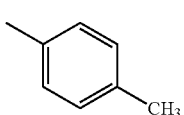
(13)
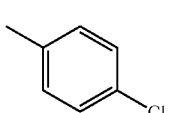
(15)
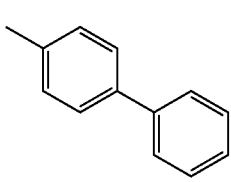
(B) Bicyclic ring
(1)
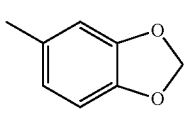
(6)
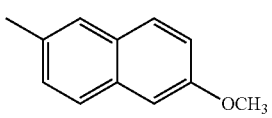
(10)
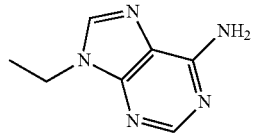
(9)
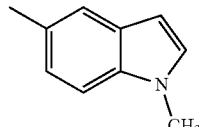
(5)
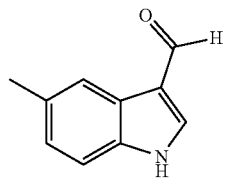
(12)
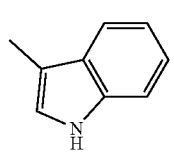
(11)
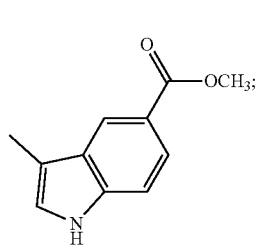
or
(d) a compound having the formula:
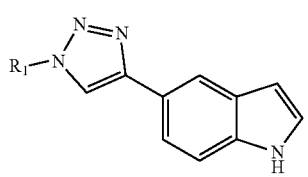
wherein R1 is independently selected from any of the following moieties:
R1 =
(1)
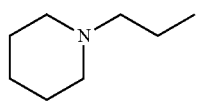
(2)
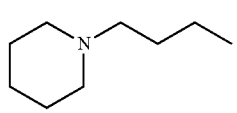

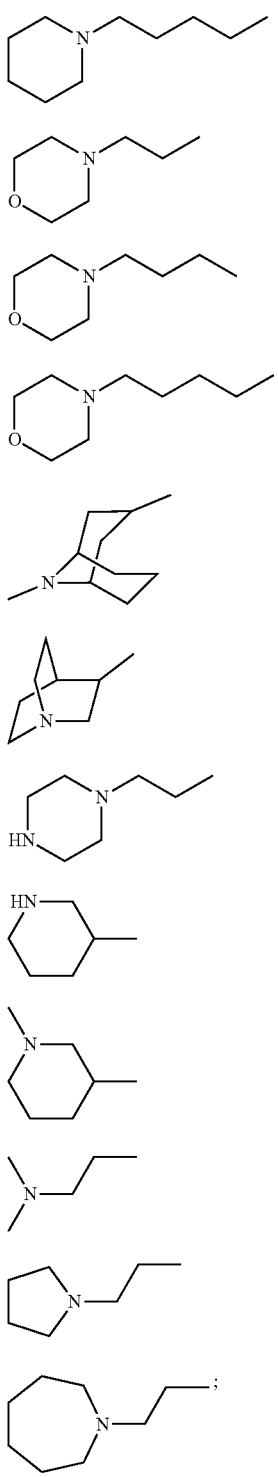

(e) a 5-((quinuclid-3-yl)-1H-1,2,3-triazol-4-yl)-1H-indole ("IND8"), a 3-(4-hydroxyphenyl-1,2,3-triazol-1-yl) quinuclidine ("QND8"), a 5-(1-(2-(Piperidin-1-yl)ethyl)-1H-1,2,3-triazol-4-yl)-1H-indole, or (f) a compound having the formula:

IND1 or (g) an equivalent, a stereoisomer, an analog, a pharmaceutically acceptable salt or a bioisostere of any of (a) to (f).

In alternative embodiments, provided are formulations comprising a compound or composition provided herein, wherein optionally the formulation is a solid, liquid, gel, hydrogel, aerosol, powder, lyophilized or emulsion formulation.

In alternative embodiments, provided are pharmaceutical compositions comprising a compound or composition provided herein, wherein optionally the pharmaceutical composition is formulated for enteral or parenteral administration, and optionally the compound is formulated for administration in vivo; or for enteral or parenteral administration, or as a tablet, pill, capsule, gel, geltab, liquid, lotion, aerosol or implant, and optionally the compound is formulated as a particle, a liposome, a nanoparticle or a nanolipoparticle.

In alternative embodiments, provided are: a kit, a pump, a device, a subcutaneous infusion device, a continuous subcutaneous infusion device, an infusion pen, a needles, a reservoir, an ampoules, a vial, a syringe, a cartridge, a pen, a disposable pen or jet injector, a prefilled pen or a syringe or a cartridge, a cartridge or a disposable pen or jet injector, or a two chambered or multi-chambered pump, comprising a compound provided herein, or a formulation provided herein, or a pharmaceutical composition provided herein.

In alternative embodiments, provided are methods for:
(a) treating, ameliorating, preventing or reversing:
a Central Nervous System (CNS) disorder involving an acetylcholine-mediated response;
a memory loss resulting from an acetylcholine mediated response;
an addiction, optionally, a nicotine addiction;
a developmental or an aging process, optionally schizophrenia, autism, a congenital seizure disorder;
a disorder or condition where presynaptic nicotinic modulation of neurotransmitter homeostasis is aberrant;
a dementia, Alzheimer's Disease, or Parkinson's disease; or,
(b) assisting in tobacco cessation or withdrawing from a nicotine addiction;
comprising:
administering to a patient or an individual in need thereof, a compound as provided herein, or a formulation as provided, or a pharmaceutical composition as provided herein, wherein optionally the compound or formulation is administered enterally or parenterally, wherein optionally the compound or formulation is administered orally, parenterally, by inhalation spray, nasally, topically, intrathecally, intrathecally, intracerebrally, epidurally, intracranially or rectally, or administering the compound, the formulation, or the pharmaceutical composition, using a kit, a pump, a device, a subcutaneous infusion device, a continuous subcutaneous infusion device, a pen, an infusion pen, a needles, a reservoir, an ampoules, a vial, a syringe, a cartridge, a disposable pen or jet injector, a prefilled pen or a syringe or a cartridge, or a two chambered or multi-chambered pump, as provided herein.

In alternative embodiments, methods provided herein further comprise administering a 5-((quinuclid-3-yl)-1H-1,2,3-triazol-4-yl)-1H-indole (IND8) or a 3-(4-hydroxyphenyl-1,2,3-triazol-1-yl) quinuclidine (QND8), or combination, optionally formulated with or administered together with compounds and compositions as provided herein, or a compound used to practice methods as provided herein, or a formulation as provided herein, or a pharmaceutical composition as provided herein.

In alternative embodiments, provided herein are uses of a compound as provided herein, or a formulation as provided herein, or a pharmaceutical composition as provided herein, in the manufacture of a medicament, and optionally the use is for:

(a) treating, ameliorating, preventing or reversing:
a Central Nervous System (CNS) disorder involving an acetylcholine-mediated response;
a memory loss resulting from an acetylcholine mediated response;
an addiction, optionally, a nicotine addiction;
a developmental or an aging process, optionally schizophrenia, autism, a congenital seizure disorder;
a disorder or condition where presynaptic nicotinic modulation of neurotransmitter homeostasis is aberrant;
a dementia, Alzheimer's Disease, or Parkinson's disease; or,
(b) assisting in tobacco cessation or withdrawing from a nicotine addiction.

In alternative embodiments, provided herein are compounds, formulas, products of manufacture or compositions for use:

as a medicament,
and optionally the medicament is used for:
(a) treating, ameliorating, preventing or reversing:
a Central Nervous System (CNS) disorder involving an acetylcholine-mediated response;
a memory loss resulting from an acetylcholine mediated response;
an addiction, optionally, a nicotine addiction;
a developmental or an aging process, optionally schizophrenia, autism, a congenital seizure disorder;
a disorder or condition where presynaptic nicotinic modulation of neurotransmitter homeostasis is aberrant;
a dementia, Alzheimer's Disease, or Parkinson's disease; or,
(b) assisting in tobacco cessation or withdrawing from a nicotine addiction; and
the compound, formula, product of manufacture or composition comprises a compound as provided herein, or a formulation as provided herein, or a pharmaceutical composition as provided herein.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of embodiments as provided herein and are not meant to limit the scope of the invention as encompassed by the claims.

FIG. 2A illustrates an acetylcholine (ACh) agonist pharmacophore, FIG. 2B illustrates a nicotine agonist pharmacophore, and FIG. 2C illustrates the exemplary compound (TTIn-1) with a pharmacophoric map, as further described in Example 1, below.

FIG. 4A and FIG. 4B graphically illustrate data showing α7-nAChR agonist dose-response curves of: FIG. 4A, the exemplary compounds IND1, IND2, IND3, IND4, IND5, IND6, IND7 and IND8; and, FIG. 4B, the exemplary compounds IND1, IND8, IND9, IND10, IND11, IND12, IND13 and IND14, as further described in Example 1, below.

FIG. 5A and FIG. 5B graphically illustrate data showing α7-nAChR agonist dose-response curves of mono- and di-substituted of phenyl ring for: FIG. 5A, the exemplary compounds of the PPRD series (for comparison, including IND1): PPRD2, PPRD3, PPRD4, PPRD8, PPRD13, PPRD15; and, FIG. 5B, the exemplary compounds of the QND series (for comparison, including IND8): QND2, QND3, QND4, QND8, QND13 and QND15, as further described in Example 1, below.

FIG. 6A and FIG. 6B graphically illustrate data showing α7-nAChR agonist dose-response curves of indole modification, other bicyclic rings, and nitrogen-rich ring for: FIG. 5A, the exemplary compounds of the PPRD series (for comparison, including IND1): PPRD1, PPRD5 and PPRD9; and, FIG. 6B, the exemplary compounds of the QND series (for comparison, including IND8): QND5, QND6, QND9, QND10, QND11 and QND12, as further described in Example 1, below.

as illustrated in FIG. 8, IND7 poorly bound to α4β2-nAChRs and showed non-competitive antagonism with low potency profiles ($K_A$=22.16$^{NC}$ μM); and as illustrated in FIG. 9, IND8 showed higher affinity binding to α4β2-nAChRs and did not elicit agonist or antagonist properties in assaying cation permeability of the intact cells, as further described in Example 1, below.

FIG. 10A IND9, FIG. 10B IND10 and FIG. 10C IND12 are mix-competitive antagonist, whereas FIG. 10D IND14 showed competitive antagonism, as further described in Example 1, below.

FIG. 11A PPRD8, FIG. 11C PPRD12, FIG. 11D PPRD14, and FIG. 11E PPRD15 are competitive antagonist, and FIG. 11B PPRD9 is a mixed (competitive, non-competitive) antagonist, as further described in Example 1, below.

(FIG. 13A) QND6, (FIG. 13C) QND9, and (FIG. 13E) QND13 are mix-competitive antagonist, whereas (FIG. 13B) QND8, (FIG. 13D) QND11, and (FIG. 13F) QND15 showed competitive antagonism, as further described in Example 1, below.

(FIG. 15A) QND4, which is mix-competitive antagonist, and (FIG. 15B) QND11, which is a non-competitive antagonist, as further described in Example 1, below.

FIG. 32 illustrates Table 1 of Example 1, which shows: Dissociation Constants for Ligand Binding, $K_d$, Activation parameters $EC_{50}$, and functional antagonism, $K_A$ values of indole series (IND1-14) and the lead compound TTIn-1 from the intact cell binding assay ($K_d$) and FRET assay using LGIC-CNiFERs $EC_{50}$ and $K_A$, as further described in Example 1, below.

Like reference symbols in the various drawings indicate like elements.

Figure 1:
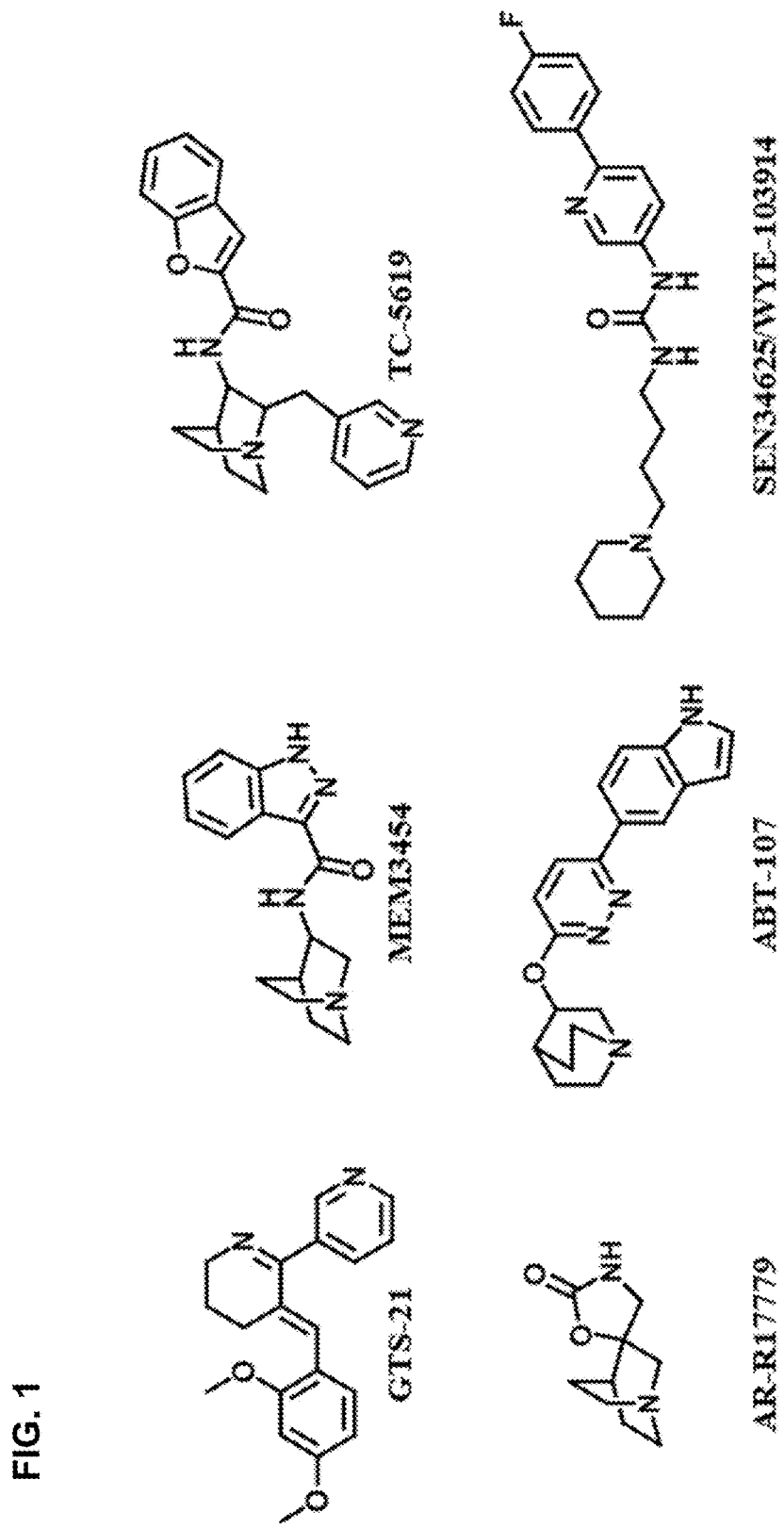
FIG. 1 illustrates alpha7 nicotine acetylcholine receptor, or α7-nAChR, agonist prototypes, as further described in Example 1, below.

Reference will now be made in detail to various exemplary embodiments as provided herein, examples of which are illustrated in the accompanying drawings. The following detailed description is provided to give the reader a better understanding of certain details of aspects and embodiments as provided herein, and should not be interpreted as a limitation on the scope of the invention.

DETAILED DESCRIPTION

Provided are selective agonists having a high affinity for the alpha7 nicotine acetylcholine receptor (α7 nAChR), and methods for making (synthesizing) and using them. In alternative embodiments, provided are a genus—an extensive series of—substituted anti 1,2,3-triazoles compounds with high affinity, and selective binding, for the alpha7 nicotine acetylcholine receptor (α7 nAChR), as exemplified by 5-(1-(2-(Piperidin-1-yl)ethyl)-1H-1,2,3-triazol-4-yl)-1H-indole ("IND1"). In alternative embodiments, exemplary compounds, such as IND1, are linked through a 1,2,3 triazole, either syn or anti.

The design of compounds as provided herein was based on a freeze-frame, click chemistry to generate the leads, refinements of structure and assay for selectivity, involving α7 versus other subtypes of human nAChR and 5HT$_3$ receptors, and then high resolution X-ray crystallography to ascertain the molecular and atomic determinants of selectivity. Hence design and refinements employed different chemical and physical methods.

Concomitant stimulation of nicotinic receptors subtypes other than α7 nicotinic receptors is in many, but not all, cases likely to produce unwanted side effects; thus, lead compounds were carried through a series of assays for receptor occupation agonist antagonist responses to ascertain selectivity. In other cases agonist activity with related ligand-gated ion channels, $5HT_{3A}$ may produce synergistic therapeutic benefit. Hence, we examined binding selectivity. Since binding poses may well govern selectivity, our studies also encompassed ascertaining the binding poses of the ligands themselves and their congeners.

In alternative embodiments, provided are methods for making the 1,2,3 triazole linked compounds provided herein, such as IND1, which are based on a reaction between aliphatic azide and alkyne building blocks to form triazoles. Since this reaction goes to completion and can actually be carried out on the very recognition or active site of the drug target, a receptor protein, lead compounds can be generated in situ. With a lead in hand, congeneric structures are generated in microarrays using small quantities of building blocks with specific catalysts to form a variety of syn- or anti-1,2,3 triazoles in submilligram quantities for assay. The formed syn- and anti-triazoles have several attributes in terms of serving as a non-ionized dipole and hydrogen bond acceptor that orients at the subunit interfaces of the pentameric receptor. Only the leads emerging from this sequence of steps need to be synthesized on a larger scale by metal catalysts in the absence of a target template for analysis of efficacy, toxicity, pharmacokinetics and tissue disposition.

Also provided are compounds 5-((quinuclid-3-yl)-1H-1, 2,3-triazol-4-yl)-1H-indole (IND8) and 3-(4-hydroxyphenyl-1,2,3-triazol-1-yl) quinuclidine (QND8), which show moderate to high selectivity for the α7 nAChR over other nicotinic receptors and the 5-HT$_3$ class of pentameric ligand-gated ion channels. They are synthesized with ionization equilibria profiles to cross the blood-brain barrier and are likely to have oral activity. The behavioral studies in three separate tests show IND8 and QND8 can partially restore cognition and memory performance of scopolamine-induced amnesic mice.

In alternative embodiments, provided are applications, or methods of using, compounds as provided herein as pharmaceuticals or therapeutics for, e.g., Central Nervous System (CNS) disorders of any acetylcholine mediated response, e.g., memory loss resulting from acetylcholine mediated responses or addictions such as nicotine addiction; and development and the aging process, for example, including uses in the developmental arena: schizophrenia, autism, certain congenital seizure disorders and other rarer conditions where presynaptic nicotinic modulation of neurotransmitter homeostasis is aberrant; and, including uses in the aging arena: dementias of the Alzheimer type, Parkinson's disease. For example, nicotine addiction can be treated (e.g., assist in tobacco cessation) using compounds as provided herein with reduced side effects.

In alternative embodiments, provided are methods for making and identifying lead compounds from 1,2,3-triazoles generated first from in situ freeze-frame click-chemistry using the acetylcholine binding protein as template. Structures were then refined by Cu$^{++}$ catalyzed generation of the anti-triazoles. In vitro receptor binding and cell-based activation studies show selectivity for these compounds as alpha-7 (α7) agonists over alpha-4b2 (α4β2) antagonism and 5HT$_3$ antagonism. K$_d$ values are in the 10-30 nM range. Behavioral studies in three separate tests show IND8 and QND8 can partially restore cognition and memory performance after scopolamine treatment and in time dependent natural memory loss.

In alternative embodiments, provided are substituted anti 1,2,3-triazole compounds and methods of using them, e.g., as exemplified by IND8 and QND8, which show dissociation constant s and EC50 activation constants for the alpha-7 (☐☐) nicotinic receptor that extend to the 10's of nanomolar concentrations. An extensive in vitro and cellular structure-activity analysis was conducted to guide further analysis. Depending on the structure, exemplary compounds as provided herein show moderate to high selectivity for the alpha7 nAChR receptor over other nicotinic receptors and the 5-HT$_3$ class of pentameric ligand-gated ion channels. The behavioral studies in mice of show in three separate tests partial restoration of cognition and memory performance after scopolamine treatment and in time dependent natural memory loss.

In alternative embodiments, compounds as provided herein as exemplified by IND1 have properties comprising:
 a. Low dissociation constants (high affinity) for the alpha-7 nAChR;
 b. Parallel potencies as agonists on alpha-7 receptors in intact cells;
 c. Selectivity for the alpha-7 nAchR over other human nicotinic receptors and serotonin (5HT$_3$) receptors;
 d. Ionization profile to cross the blood-brain barrier;
 e. Oral activity;
 f. Correlation between receptor occupation, responses and cognitive improvement and memory function in mice;
 g. Blockade of alpha-7 receptor responses by the alpha-7 antagonist methyllycaconitine that correlates with the blockade of cognition improvement.

Structurally, nAChRs are members of Cys-loop ligand-gated ion channel (LGIC) superfamily, which are composed of five transmembrane spanning subunits, assembled surrounding a centrosymmetric ion pore.[9] There are at least 12 distinct neuronal subunits (α2-α10 and β2-β4) characterized in mammalian and avian systems.[9,10] The structure of these pentameric receptors is divided into three domains: the N-terminal extracellular, transmembrane, and intracellular domains. Assembly of nAChRs is specific for certain subunit partnerships, and can be categorized in two major assemblies: hetero-pentameric and homo-pentameric. Differences in subunit combinations and localization lead to their functional and pharmacological variances.[9,11,12] The orthosteric ligand binding pocket is located at the interface between a principal (alpha) and a complementary subunit in the extracellular domain.[9,13] The α7-nAChR is unique in being homomeric with identical binding sites formed between its principal, C loop containing face and the opposing face of the neighbor.

Bioisosteres of Compounds

In alternative embodiments, provided are bioisosteres of compounds of compounds and compositions as provided herein, or a compound used to practice methods as provided herein. In alternative embodiments, bioisosteres as provided herein are compounds comprising one or more substituent and/or group replacements with a substituent and/or group having substantially similar physical or chemical properties which produce substantially similar biological properties to a compound as provided herein or a stereoisomer, racemate or isomer thereof. In one embodiment, the purpose of exchanging one bioisostere for another is to enhance the desired biological or physical properties of a compound without making significant changes in chemical structures.

For example, in one embodiment, bioisosteres of compounds and compositions as provided herein, or a compound used to practice methods as provided herein, are made by replacing one or more hydrogen atom(s) with one or more fluorine atom(s), e.g., at a site of metabolic oxidation; this may prevent metabolism (catabolism) from taking place. Because the fluorine atom is only slightly larger than the hydrogen atom the overall topology of the molecule is not significantly affected, leaving the desired biological activity unaffected. However, with a blocked pathway for metabolism, the molecule may have a longer half-life or be less toxic, and the like.

Products of Manufacture, Kits

Also provided are products of manufacture and kits for practicing the methods as provided herein. In alternative embodiments, provided are products of manufacture and kits comprising all the components needed to practice a method as provided herein.

Provided are kits comprising compositions and/or instructions for practicing methods as provided herein. In alternative embodiments, provided are kits comprising: a composition used to practice a method as provided herein, optionally comprising instructions for use thereof.

In alternative embodiments, provided are pumps, devices, subcutaneous infusion devices, continuous subcutaneous infusion device, pens, infusion pens, needles, reservoirs, ampoules, vials, syringes, cartridges, disposable pen or jet injectors, prefilled pens or syringes or cartridges, cartridge or disposable pen or jet injectors, two chambered or multi-chambered pumps, syringes, cartridges or pens or jet injectors comprising a composition or a formulation as provided herein. In alternative embodiments, the injector is an auto-injector, e.g., a SMARTJECT® autoinjector (Janssen Research and Development LLC); or a MOLLY®, or DAI®, or DAI-RNS® autoinjector (SHL Group, Deerfield Beach, Fla.). In alternative embodiments, the injector is a hypodermic or a piston syringe.

Formulations and Pharmaceutical Compositions

In alternative embodiments, provided are compounds and compositions, including formulations and pharmaceutical compositions, for use in in vivo, in vitro or ex vivo methods for treating, ameliorating, preventing, or reversing, e.g., Central Nervous System (CNS) disorders of any acetylcholine mediated response, e.g., memory loss resulting from acetylcholine mediated responses or addictions such as nicotine addiction; and development and the aging process, for example, including uses in the developmental arena: schizophrenia, autism, certain congenital seizure disorders and other rarer conditions where presynaptic nicotinic modulation of neurotransmitter homeostasis is aberrant; and, including uses in the aging arena: dementias of the Alzheimer type, Parkinson's disease. For example, nicotine addiction can be treated (e.g., assist in tobacco cessation) using compounds as provided herein with reduced side effects.

In alternative embodiments, the pharmaceutical compositions as provided herein can be administered parenterally, topically, orally or by local administration, such as by aerosol or transdermally. In alternative embodiments, pharmaceutical compositions can be prepared in various forms, such as granules, tablets, pills, capsules, suspensions, taken orally, suppositories and salves, lotions and the like. Pharmaceutical formulations as provided herein may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, geltabs, on patches, in implants, etc. In practicing embodiments as provided herein, the pharmaceutical compounds can be delivered by transdermally, by a topical route, formulated as applicator sticks, solutions, suspensions, emulsions, gels, creams, ointments, pastes, jellies, paints, powders, and aerosols. Oral carriers can be elixirs, syrups, capsules, tablets, pills, geltabs and the like.

In alternative embodiment, compounds and compositions as provided herein, or a compound used to practice methods as provided herein, are delivered orally, e.g., as pharmaceutical formulations for oral administration, and can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

In alternative embodiments, liquid carriers are used to manufacture or formulate compounds as provided herein, or a composition used to practice the methods as provided herein, including carriers for preparing solutions, suspensions, emulsions, syrups, elixirs and pressurized compounds. The active ingredient (e.g., a composition as provided herein) can be dissolved or suspended in a pharmaceutically acceptable liquid carrier such as water, an organic solvent, a mixture of both or pharmaceutically acceptable oils or fats. The liquid carrier can comprise other suitable pharmaceutical additives such as solubilizers, emulsifiers, buffers, preservatives, sweeteners, flavoring agents, suspending agents, thickening agents, colors, viscosity regulators, stabilizers or osmo-regulators.

In alternative embodiments, solid carriers are used to manufacture or formulate compounds as provided herein, or a composition used to practice the methods as provided herein, including solid carriers comprising substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

In alternative embodiments, concentrations of therapeutically active compound in a formulation can be from between about 0.1% to about 100% by weight.

In alternative embodiments, therapeutic formulations are prepared by any method well known in the art, e.g., as described by Brunton et al., eds., Goodman and Gilman's: The Pharmacological Bases of Therapeutics, 12th ed., McGraw-Hill, 2011; Remington: The Science and Practice of Pharmacy, Mack Publishing Co., 20th ed., 2000; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

In alternative embodiments, therapeutic formulations are delivered by any effective means appropriated for a particular treatment. For example, depending on the specific antitumor agent to be administered, the suitable means include oral, rectal, vaginal, nasal, pulmonary administration, or parenteral (including subcutaneous, intramuscular, intravenous and intradermal) infusion into the bloodstream. For parenteral administration, antitumor agents as provided herein may be formulated in a variety of ways. Aqueous solutions of the modulators can be encapsulated in polymeric beads, liposomes, nanoparticles or other injectable depot formulations known to those of skill in the art. In alternative embodiments, compounds and compositions as provided herein, or a compound used to practice methods as provided herein, are administered encapsulated in liposomes (see below). In alternative embodiments, depending upon solubility, compositions are present both in an aqueous layer and in a lipidic layer, e.g., a liposomic suspension. In alternative embodiments, a hydrophobic layer comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton Pa. ("Remington's"). For example, in alternative embodiments, compounds and compositions as provided herein, or a compound used to practice methods as provided herein, are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers used to practice embodiments as provided herein can be in forms such as tablets, pills, powders, capsules, liquids, gels, syrups, slurries, suspensions, etc., suitable for in vivo, in vitro or ex vivo applications.

In practicing embodiments as provided herein, the compounds (e.g., formulations) as provided herein can comprise a solution of compositions disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice embodiments as provided herein are sterile and can be manufactured to be generally free of undesirable matter. In one embodiment, these solutions and formulations are sterilized by conventional, well known sterilization techniques.

The solutions and formulations used to practice methods as provided herein can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compounds and compositions as provided herein, or a compound used to practice methods as provided herein, can be delivered by the use of liposomes. In alternative embodiments, by using liposomes, particularly where the liposome surface carries ligands specific for target cells or organs, or are otherwise preferentially directed to a specific tissue or organ type, one can focus the delivery of the active agent into a target cells in an in vivo, in vitro or ex vivo application.

The compounds and compositions as provided herein, or a compound used to practice methods as provided herein, can be directly administered, e.g., under sterile conditions, to an individual (e.g., a patient) to be treated. The modulators can be administered alone or as the active ingredient of a pharmaceutical composition. Compositions and formulations as provided herein can be combined with or used in association with other therapeutic agents. For example, an individual may be treated concurrently with conventional therapeutic agents.

Nanoparticles, Nanolipoparticles and Liposomes

Provided are nanoparticles, nanolipoparticles, vesicles and liposomal membranes comprising compounds and compositions used to practice the methods and embodiments as provided herein. Provided are multilayered liposomes comprising compounds used to practice embodiments as provided herein, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice embodiments as provided herein.

Liposomes can be made using any method, e.g., as described in Park, et al., U.S. Pat. Pub. No. 20070042031, including method of producing a liposome by encapsulating an active agent (e.g., compounds and compositions as provided herein, or a compound used to practice methods as provided herein), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice embodiments as provided herein comprise a substituted ammonium and/or polyanions, e.g., for targeting delivery of a compound as provided herein, or a compound used to practice methods as provided herein, to a desired cell type or organ, e.g., brain, as described e.g., in U.S. Pat. Pub. No. 20070110798.

Provided are nanoparticles comprising compounds as provided herein, e.g., used to practice methods as provided herein in the form of active agent-containing nanoparticles (e.g., a secondary nanoparticle), as described, e.g., in U.S. Pat. Pub. No. 20070077286. In one embodiment, provided are nanoparticles comprising a fat-soluble active agent used to practice embodiments as provided herein, or a fat-solubilized water-soluble active agent to act with a bivalent or trivalent metal salt.

In one embodiment, solid lipid suspensions can be used to formulate and to deliver compositions used to practice embodiments as provided herein to mammalian cells in vivo, in vitro or ex vivo, as described, e.g., in U.S. Pat. Pub. No. 20050136121.

Delivery Vehicles

In alternative embodiments, any delivery vehicle can be used to practice the methods as provided herein, e.g., to deliver compounds and compositions as provided herein, or a compound used to practice methods as provided herein, to mammalian cells, e.g., neural cells, or brain cells, in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate compounds and compositions as provided herein, or a compound used to practice embodiments as provided herein, e.g. as described, e.g., in U.S. Pat. Pub. No. 20040151766.

In one embodiment, compounds and compositions as provided herein, or a compound used to practice methods as provided herein, can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to polyphosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

Dosaging

The pharmaceutical compositions and formulations as provided herein can be administered for prophylactic and/or therapeutic treatments. In therapeutic applications, compositions are administered to a subject, e.g., a human in need thereof, in an amount sufficient to cure, alleviate or partially arrest the clinical manifestations of the agent and/or its complications (a "therapeutically effective amount").

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods as provided herein are correct and appropriate.

The invention will be further described with reference to the following examples; however, it is to be understood that the invention is not limited to such examples.

EXAMPLES

Example 1: Effectiveness of Exemplary Compositions as Selective α7 Nicotinic Acetylcholine Receptor (nAChR) Agonists This example demonstrates the effectiveness of exemplary compositions as provided herein as selective α7 nicotinic acetylcholine receptor (nAChR) agonists. In alternative embodiments, provided are methods and uses for these compounds.

Several α7-nAChR agonists have been developed for clinical trial: namely GTS-21,[14,15] MEM3454,[16] TC-5619,[17] AR-R17779,[18] ABT-107,[19] and SEN34625/WYE-103914[20] (FIG. 1). For α7-nAChR agonist design, all primary pharmacophoric features of α7-nAChR agonists[18,21], a cationic center, a H-bond acceptor, and a hydrophobic moiety were modified.[9,17,22] Despite comprehensive studies, limitations in the development of α7-nAChR agonists encompassing selectivity, stability, and toxicity, remain.[17,23]

The 1,2,3-triazole based molecules from copper catalyzed azide-alkyne cycloaddition (CuAAC) or click chemistry have been reported to stimulate α7-nAChRs as agonists and antagonize α4β2-nAChRs and 5HT$_{3A}$ receptors.[24,25] The triazole ring serves as an uncharged H-bond acceptor and stable linker between the cationic center and the hydrophobic ring[24,26]. FIG. 1 illustrates α7-nAChR agonist prototypes.

In this study, the cationic center and hydrophobic indole of the triazole based lead compound, TTIn-1, were modified to improve the selectivity and potency profiles to α7-nAChRs. Simple tertiary amines that can cross the blood brain barrier (BBB) and are able to protonate in brain were chosen to serve as the cationic center in the α7-nAChR pharmacophore. The carbon chain between the cationic center and the H-bond acceptor or triazole was varied to determine an optimum length to maintain both a cation-π interaction from the basic amine and a H-bond formation between triazole and amino acid residues in binding pockets of α7-nAChRs. The role of functional group in a hydrophobic region, where the uncharged pyridine of nicotine or epibatidine resides, was studied as well. Receptor binding and functional assays of synthesized compounds were carried out by radioligand binding and fluorescence resonance energy transfer (FRET) assays, respectively.

Results and Discussion

A) Design Strategies

Figure 2C:
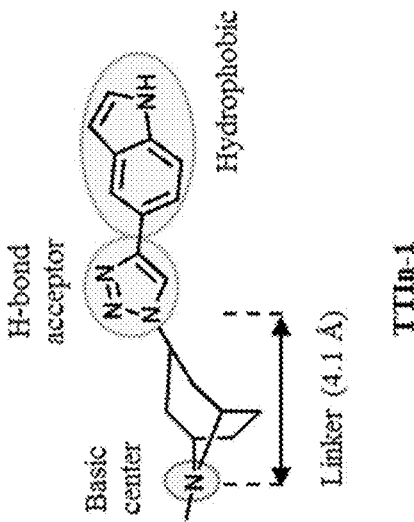
FIG. 2A, FIG. 2B and FIG. 2C illustrate α7-nAChR agonist pharmacophores.
Figure 2B:
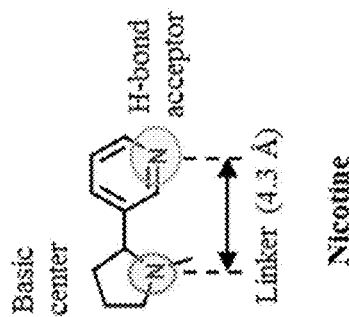
Figure 2A:
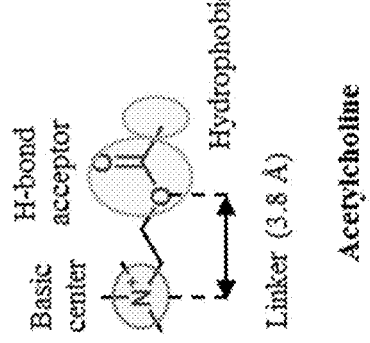

FIG. 2 illustrates α7-nAChR agonist pharmacophore. (A) acetylcholine (ACh), (B) nicotine, and (C) lead compound (TTIn-1) with pharmacophoric map.

The exemplary (the "lead") compound TTIn-1 (illustrated in FIG. 2) from a tropane derivative library was modified, where the components of α7-nAChR pharmacophore encompassed: (i) the basic center with its linker ($R_1$ of IND series) and (ii) hydrophobic aromatics ($R_2$ of PPRD and QND series); lead modification strategies were presented in FIG. 3.

Figure 3:
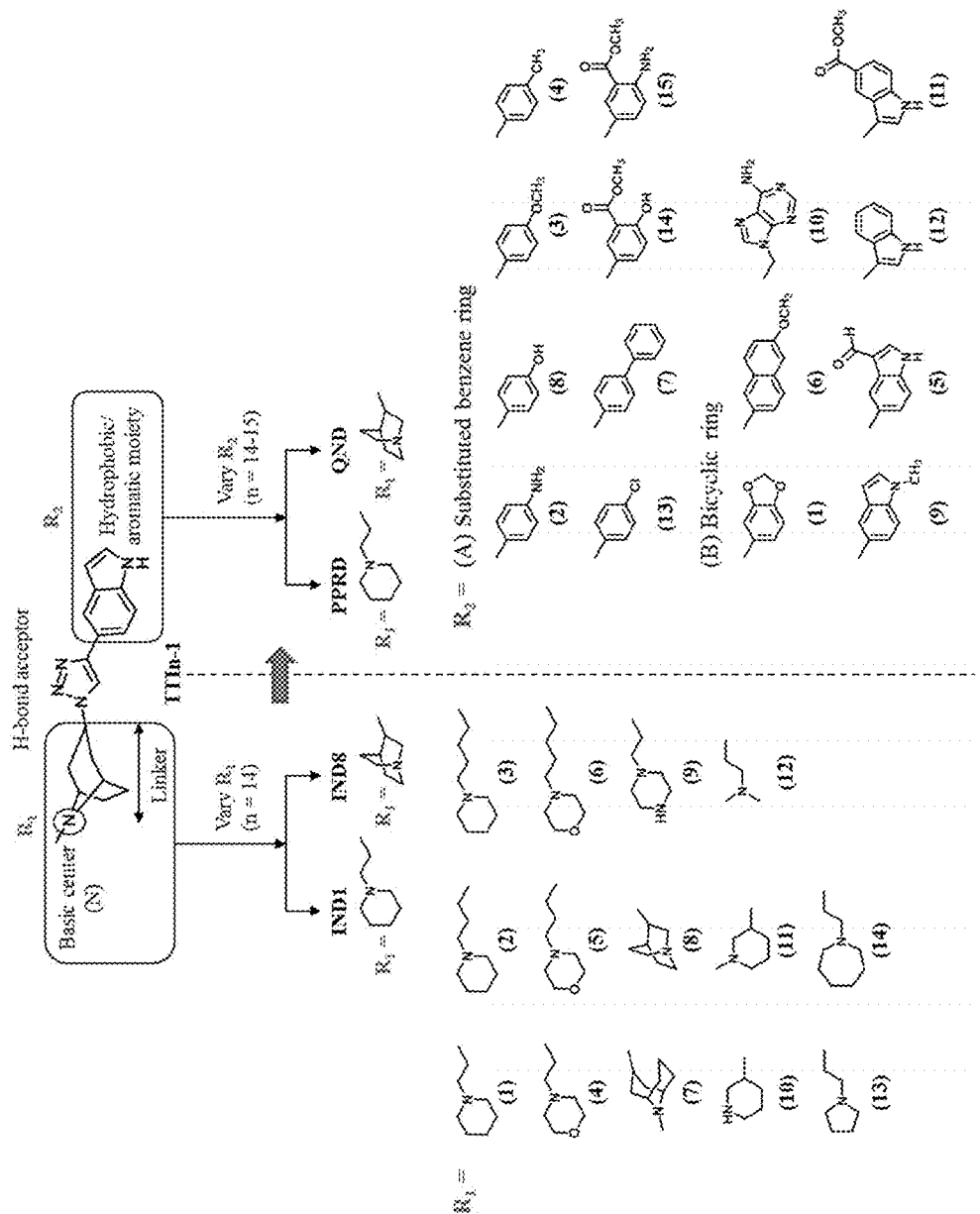
FIG. 3 illustrates modification strategies of the exemplary (the "lead") compound TTIn-1 (illustrated in FIG. 2 and at the top of FIG. 3): exemplary alternative embodiments of $R_1$ of the IND series (compounds provided herein having a basic center); and, exemplary alternative embodiments of $R_2$ of the PPRD and QND series (compounds provided herein having hydrophobic aromatics, including substituted benzene rings and bicyclic rings), as further described in Example 1, below.

In the first set of 14 compounds (IND1-14), the basic center in tropane ring was a prime focus. The tropane of TTIn-1 was replaced with different structures of amine fragments: (i) simple alicyclic ring (IND1-6, 9) i.e. piperidine, morpholine, and piperazine, (ii) fused alicyclic ring (IND7-8), (iii) semi-rigid analogs of 2 carbon linker (IND10-11), (iv) freely flexible aliphatic amine (IND12), and (v) reduced and enlarged alicyclic ring (IND13-14). Modifications were made to investigate the role of the distance between basic nitrogen and triazole ring, the flexibility or spatial configuration, and the steric hindrance in the binding affinity and potency. Simple monocyclic amines with lower $pK_a$ values in the range of 6.93-9.66 were chosen to replace the tropane ring of TTIn-1 ($pK_a$ 9.67) for pharmacokinetic advantage. At physiological pH, only 0.5% of tropane remains unprotonated for facile penetration across BBB. Once the compound crosses the blood-brain barrier, it establishes an ionization equilibrium consistent with extracellular pH values in the CNS. The pharmacologically active form requires protonation of the basic amine to enable hydrogen bond formation with the backbone carbonyl oxygen of a conserved Trp on the principal face of the nAChR. Therefore, the $pK_a$ should accommodate both blood-brain penetration (pharmacokinetics) and receptor binding of the protonated species (pharmacodynamics). The azabicyclo [3.3.1]nonane ring (IND7) imparts additional steric and hydrophobic contributions through additional carbon atoms in bicyclic ring. The quinuclidine ring (IND8), which was reported to be a selective α7-nAChR agonist,[27] was chosen to compare with the tertiary tropane in TTIn-1 as well. The length between basic nitrogen atom and triazole ring of the designed compounds was in range of 2-4 carbon length (3.7-6.4 Å). The varied distance was based on the 2 carbon atoms in acetylcholine structure (3.8 Å, FIG. 2A) and 4 carbon atoms between the piperidine nitrogen and urea moiety (H-bond acceptor) of SEN34625/WYE-103914[20] (6.4 Å, FIG. 1). For IND9-14, the number of carbon atoms between the basic amine and triazole ring was fixed at two, but the spatial orientation was varied by semi-rigid analog approach. The effect of additional basic nitrogen (IND9) and the flexibility of the basic center (IND10-12) with 2 methylene linkers were studied. The pyrrolidine (IND13) and azepane (IND14) were chosen to represent the ring size reduction and expansion, respectively. FIG. 3 illustrates optimization of the lead compound, TTIn-1.

In the second set, the hydrophobic $R_2$ in two series (PPRD and QND series) of twenty nine compounds was separated into 2 categories, (i) simple benzene ring with mono- and di-substitution and (ii) bicyclic systems: indole and substituted indole, naphthalene and adenine rings. The $R_1$ of compounds in PPRD and QND series were the piperidine of IND1 and the quinuclidine of IND8, respectively as IND1 and IND8 showed good binding affinity to α7-nAChR ($K_d$<0.17 µM). The hydrophobic benzene ring was substituted with H-bond donor (PPRD and QND2, 8), H-bond acceptor (PPRD and QND3), carbon atom (PPRD and QND4), halogen atom (PPRD and QND13), or aromatic moiety (PPRD and QND7) to verify the important role of H-bond interaction. The methyl ester (PPRD and QND14-15) was included to study the effect from added heteroatom. The indole ring was modified in terms of substitution (PPRD and QND 5, 9, 11-12), and changed to other bicyclic rings (1,3-benzodioxole in PPRD and QND1, and 2-methoxynaphthalene in PPRD and QND6). The hydrophilic nitrogen-rich adenine ring (PPRD and QND10) was also added to confirm the essential role of hydrophobic group in the pharmacophoric model.

Figure 17:
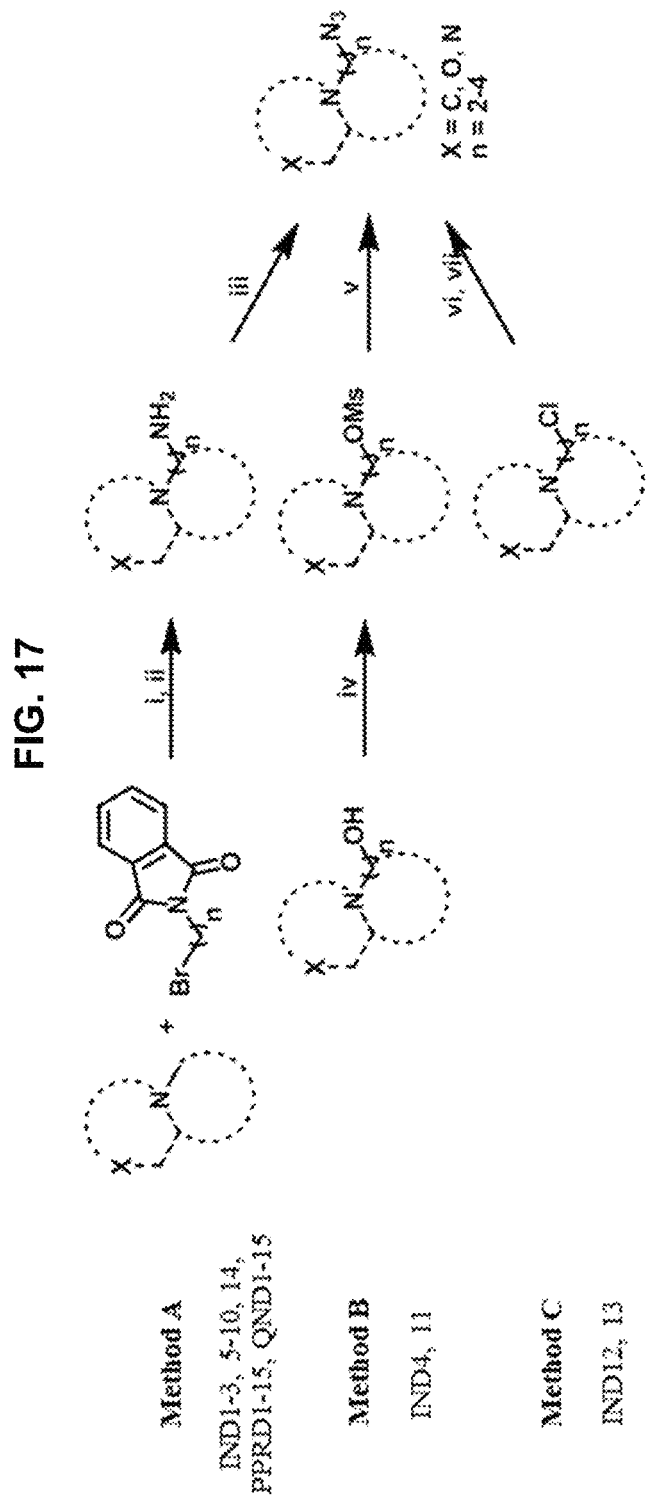
FIG. 17 schematically illustrates how azide building blocks were prepared using three different methods: the diazo transfer reaction of amine using freshly prepared trifluoromethanesulfonyl azide ($TfN_3$) (method A), and the nucleophilic substitution of a leaving group with sodium azide (method B and C), as further described in Example 1, below.

B) Synthesis
Scheme 1 (See FIG. 17).

Synthesis of azide building block: Reagents and conditions: (i) $Et_3N$, EtOH, reflux, overnight; (ii) $H_2N-NH_2$, reflux 45 min; (iii) freshly prepared $TfN_3$ in toluene, $K_2CO_3$, $CuSO_4 \cdot 5H_2O$, $H_2O$, $CH_3OH$, RT, overnight; (iv) MsCl, $Et_3N$, $CH_2Cl_2$, 0° C. to RT, 4 h; (v) $NaN_3$, MeCN, reflux, 6 h; (vi) $NaN_3$, $H_2O$, reflux, overnight; (vii) NaOH, $Et_2O$, 0° C., 30 min.

The general synthesis of the designed compounds started with the synthesis of azide and alkyne building blocks followed by the copper catalyzed azide-alkyne cycloaddition (CuAAC) reaction or click chemistry,[24] yielding the final compounds. The azide building blocks were prepared from three different methods: the diazo transfer reaction of amine using freshly prepared trifluoromethanesulfonyl azide ($TfN_3$) (method A), and the nucleophilic substitution of a leaving group with sodium azide (method B and C) as shown in Scheme 1. Azide building blocks of IND1-3, 5-10, 14, PPRD1-15 and QND1-15 were prepared by method A, whereas IND4, 11 were prepared by method B and IND12-13 by method C. Then, the azide building blocks were reacted with the terminal alkynes that are commercially available or were prepared in house by the Sonogashira cross-coupling reaction[28] or nucleophilic substitution (Scheme 2) via click chemistry as shown in Scheme 3 to yield 1,2,3-triazole based indoles with 20-95% yield.

Figure 18A:
FIG. 18 schematically illustrates Scheme 2, the synthesis of terminal alkyne: Reagents and conditions: Step (i) TMS-C≡CH, CuI, $PdCl_2(PPh_3)_2$, DMF, RT, overnight; Step (ii) TBAF in THF or $K_2CO_3$ in $CH_3OH$, room temperature (RT), 1 hour (h), as further described in Example 1, below.
Figure 18B:
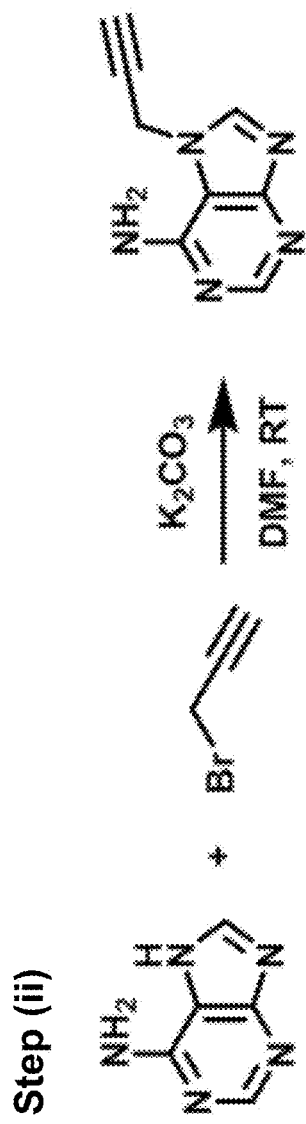

Scheme 2 (See FIG. 18).

Synthesis of terminal alkyne: Reagents and conditions: Step (i) TMS-C≡CH, CuI, $PdCl_2(PPh_3)_2$, DMF, RT, overnight; Step (ii) TBAF in THF or $K_2CO_3$ in $CH_3OH$, RT, 1 h.

Figure 19:
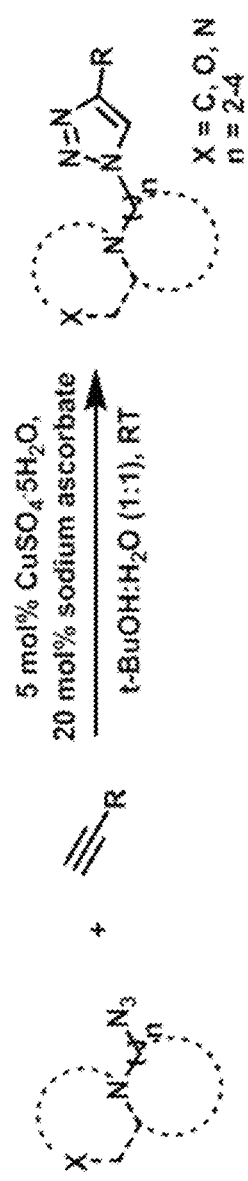
FIG. 19 schematically illustrates Scheme 3, synthesis of anti-1,2,3-triazole containing molecules, as further described in Example 1, below.

Scheme 3 (See FIG. 19).

Synthesis of anti-1,2,3-triazole containing molecules, the exemplary PNU-282987, IND8 and QND8.

C) Biological Evaluation

All synthesized compounds were screened for the binding potential with cell based neurotransmitter fluorescent engineered reporters (CNiFERs) expressed α7-nAChRs, α4β2-nAChRs, and $5HT_{3A}$ receptors. The whole cell binding assay was performed by competitive radioligand binding assay (RBA) using [³H]-(±)-epibatidine for α7- and α4β2-nAChRs and [³H]-granisetron for $5HT_{3A}$ receptors. The α7/$5HT_{3A}$ chimera receptor, having an α7-nAChR extracellular domain and $5HT_{3A}$ transmembrane and cytoplasmic domains, was used instead of α7-nAChRs because the signal-to-noise ratio of α7-nAChRs from method optimization was significantly lower compared with the α7/$5HT_{3A}$ chimeric receptors. Besides the enhanced sensitivity, the chimeric receptors produced robust and reproducible results (data not shown). Compounds at 10 µM concentration that dissociated [³H]-(±)-epibatidine or [³H]-granisetron binding to LGIC-CNiFERs more than 50% were further determined over a range of concentrations for $K_d$ values. Otherwise their $K_d$ value was listed as >10 µM.

Compounds were functionally screened as agonists and antagonists, for selectivity and potency using FRET assay of LGIC-CNiFERs transfected cells expressing α7-nAChRs, α4β2-nAChRs, and $5HT_{3A}$ receptors.[29] All LGIC-CNiFERs for functional characterization are the same as those used for the competitive RBA with the exception that α7-nAChRs were used instead of chimera receptors. Initially, the agonist properties of tested compounds were assessed directly. Then, antagonism was subsequently evaluated by adding the standard agonists, (±)-epibatidine for α7- and α4β2-nAChRs and 5-hydroxytryptamine (5-HT) for $5HT_{3A}$ receptors. All α7-nAChR functional assays were performed in the presence of PNU-120596, an α7-nAChR positive allosteric modulator (PAM), to increase signal and delay the sensitization state of α7-nAChRs enabling the measurement of more prolonged FRET signals.[29] Compounds having agonist responses of ≥0.20 were determined for $EC_{50}$, and compounds having inhibition fraction of ≥0.50 were determined for $K_A$.[25] $EC_{50}$>13.3 µM and $K_A$>10 µM which are a screening concentration for agonist and antagonist, respectively were reported compounds not taken for further in the screening of receptor occupation and responses.

1) Effect of Variation in Basic Amine (IND Series)

1.1) Effect of Basic Amine Center on Binding Affinity ($K_d$)

Eleven compounds from the set (IND1-3, 6-8, 10-14) passed the initial screening for α7-nAChRs binding. Only one compound (IND8) binds to α4β2-nAChRs and eight compounds (IND1-2, 7-8, 10-12, 14) are able to interact with $5HT_{3A}$ receptors. $K_d$ values are shown in Table 1 (as illustrated in FIG. 32).

Table 1 (as illustrated in FIG. 32) shows: Dissociation Constants for Ligand Binding, $K_d$, Activation parameters $EC_{50}$, and functional antagonism, $K_A$ values of indole series (IND1-14) and the lead compound TTIn-1 from the intact cell binding assay ($K_d$) and FRET assay using LGIC-CNiFERs $EC_{50}$ and $K_A$. The following formula is used to illustrate the compounds from Table 1, where the R group is defined in Table 1.

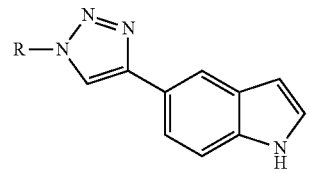

Data were analyzed from at least three independent experiments with each experiment containing at least duplicate samples. Values are reported as means±standard deviation (SD). The $K_d$>10 µM, $EC_{50}$>10 µM, and $K_A$>10 µM were indicated in the compounds that did not pass the initial screening for binding affinity and functional characterization. *partial agonist; $^C$competitive antagonist; $^{NC}$non-competitive antagonist. Values are calculated as described in methods.

The $K_d$ values with α7-nAChRs indicate that four compounds (IND1, 8, 10, 14) exhibit enhanced affinity for the α7-nAChRs ($K_d$=0.12-2.98 µM) better than lead compound, TTIn-1 ($K_d$=4.20 µM). For the simple alicyclic ring, the greater binding affinity of IND1 (3.8 Å linker length, $K_d$=0.34 M) than for IND2 (length 5.1 Å, $K_d$=7.20 µM) and IND3 (length 6.4 Å, $K_d$=13.76 µM) reveals that the increase in length of the linker reduces the binding affinity to α7-nAChRs. This flexible linker and the folding structure impart steric hindrance and make the indole ring interactions with amino acid residues in the hydrophobic region leading to the lower affinity. Besides linker elongation, the additional heteroatom (IND4-6, 9) in the simple alicyclic ring dramatically reduces the binding affinity to α7-nAChRs. The reasons for lack of binding ability of IND4-5 and 9 are (i) the greater hydrophilicity of morpholine and piperazine moieties impedes access to the aromatic nest in the binding pocket. An exception is IND6 whose log P increases from additional carbon atom together with flexibility optimizing distance, (ii) the steric hindrance of the additional heteroatom (oxygen atom in IND4, 5 and nitrogen atom in IND9), (iii) the low p$K_a$ of IND4, 5 leads to a lower fraction protonated forms (25% and 54%, respectively) to form a cation-π interaction, or (iv) the secondary amine of IND9 is protonated at pH 7.4 resulting in inappropriate distance (6.7 Å) to maintain both cation-π and hydrogen bond interactions with amino acid residues in the binding pocket. Both of the fused alicyclic rings in this study (IND7, 8) can interact with α7-nAChRs. The binding affinity of IND7 ($K_d$=4.52 µM) having one additional carbon atom from TTIn-1 did not affect the α7-nAChR binding affinity due to the restricted fused ring. Although, the physiochemical properties, p$K_a$ and log P, of IND7 and IND8 are almost the same, the binding affinity to α7-nAChRs of IND8 ($K_d$=0.12 µM) was better. This might come from the optimal distance to maintain cation-π and hydrogen bond interactions of IND8 (3.7 Å). For the semi-rigid analog, IND10 ($K_d$=2.98 µM), a secondary amine, was found to bind to the α7-nAChRs better than lead compound and IND11 which is a tertiary amine ($K_d$=5.07 µM), the less steric hindrance and higher p$K_a$ may contribute to the good affinity of IND10. Freely flexible aliphatic amine and ring size alteration affecting to the lipophilicity also have an impact on the binding affinity. The lower lipophilicity of IND12 (log P=2.17, $K_d$=7.68 µM) and IND13 containing five-membered ring (log P=2.58, $K_d$=4.84 µM) apparently caused the decrease in binding comparing to the more lipophilic IND14 containing seven-membered ring (log P=3.47, $K_d$=1.05 µM) with higher lipophilicity has better binding affinity than lead compound. The higher lipophilicity accelerated access to the aromatic cage in the binding pocket leading to the higher binding affinity.

The cation selective channels in the pentameric ligand gated ion channel family, in addition to the multiple subtypes of nicotinic receptors, include the 5HT$_{3A}$ receptors, so we have included this receptor and the most abundant nAChR subtype α4β2 in our analysis[23]. Almost all compounds that are able to interact with α7-nAChRs also bind to 5HT$_{3A}$ receptors, but there is far less of a cross-over to the α4β2-nAChRs where only IND8 showed an interaction. This is surprising since α7 and cα4β2-nAChRs obviously share similar agonist selectivity.[30]

1.1) Effect of basic amine center on functional activity (agonist and antagonist) The functional screening of this first compound set (IND1-14) to LGIC receptors indicates that twelve compounds (IND1-3, 6-14) are α7-nAChR agonists and ten compounds are selective α7-nAChR agonists. There is only one compound (IND7) showed weak antagonistic properties to α4β2-nAChRs. One compound (IND8) showed agonistic properties to 5HT$_{3A}$ receptors but seven fold lower than its α7-nAChR agonistic effect. Four compounds (IND9-10, 12, 14) are 5HT$_{3A}$ receptor antagonists. The $EC_{50}$ of agonists and $K_A$ values of antagonists are shown in Table 1.

Figure 4A:
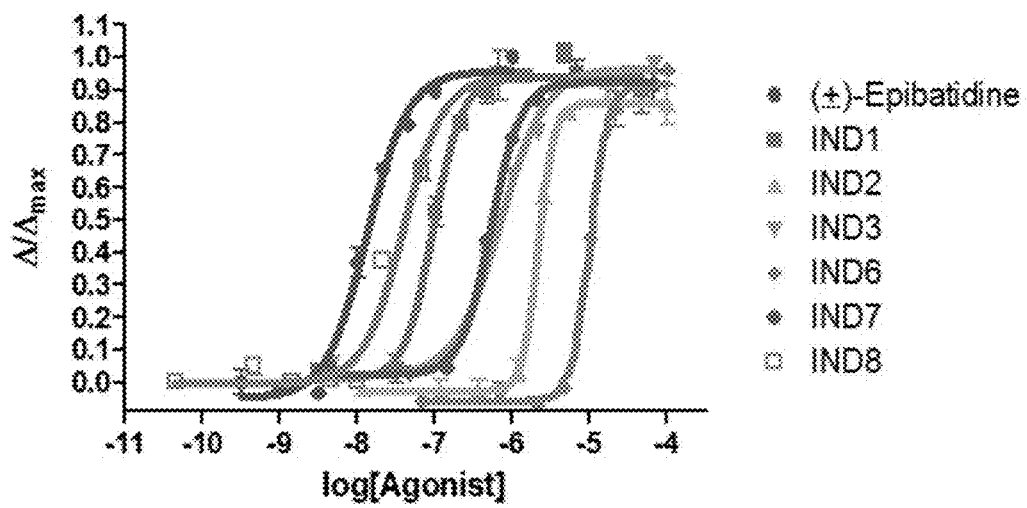
Figure 4B:
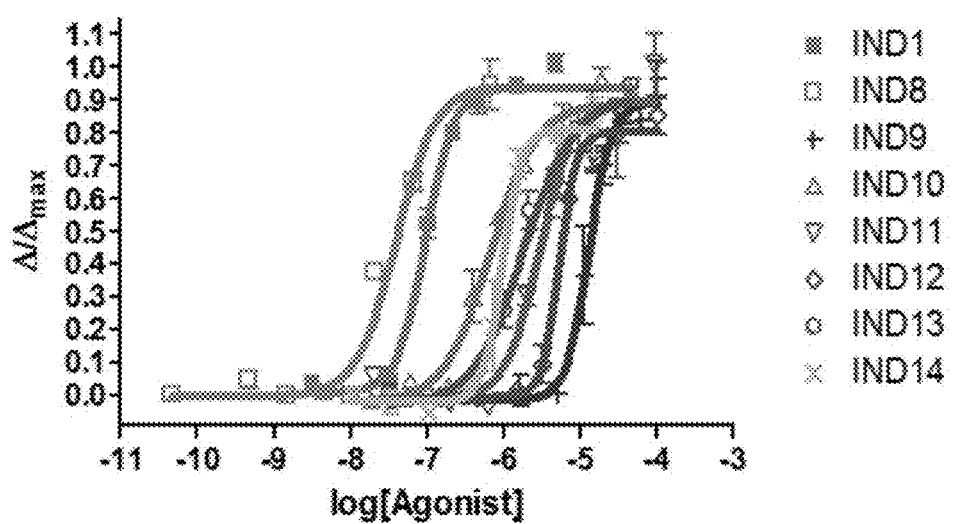

The α7-nAChR agonist potency is in agreement with the binding affinity. IND1-6 bearing monocyclic amine are selective to α7-nAChRs. Only IND1 is more potent than TTIn-1, $EC_{50}$ values of 0.17 µM vs 0.57 µM, respectively. The higher potency profile of IND1 came from the protonated piperidine (p$K_a$ 9.13) with an optimal length (3.8 Å) which accommodate H-bond in the binding pocket of α7-nAChRs. The increase of methylene linker in simple monocyclic ring generally caused the decrease in the potency profile except for IND3 ($EC_{50}$=0.91 µM) and IND6 ($EC_{50}$=12.20 µM), which the carbon chain (6.4 Å) can fold to interact with amino acid residues in the binding pocket contributing to the agonistic activity. In contrast to weak to moderate binding $K_d$ values of IND3 ($K_d$=13.8 µM, log P=3.60) and IND2 ($K_d$=7.2 µM, log P=3.08), the $EC_{50}$ values are 0.91 and 2.2 µM, respectively. The α7-nAChR potency of molecules containing additional heteroatom (IND4-6, 9) and fused alicyclic ring (IND7-8) are in accordance to the binding $K_d$ values. IND8 is the most potent α7-nAChR agonist ($EC_{50}$=0.03 µM). Moreover, the α7-nAChR agonistic activities of other six semirigid analogs (IND9-14) that the number of carbon atom linker between basic amine and triazole ring was fixed at two carbon atom with the distance of 3.8 Å are in agreement with the binding affinity. IND10 a, secondary amine of fewer steric constraints, is more potent than the bulky tertiary amine IND11, $EC_{50}$ values of 0.66 µM and 3.3 µM, respectively. Agonist potencies are also decreased in compounds with free rotatable aliphatic chain (IND12, $EC_{50}$=5.74 µM) and ring size modification (IND13-14, $EC_{50}$=2.17 and 0.78 µM, respectively). This indicates that not only the length but the flexibility and steric influences govern the potency of α7-nAChR agonist. The α7-nAChR dose-response curves of IND1-14 are shown in FIG. 4, that illustrate data showing α7-nAChR agonist dose-response curves of (A) IND1-8 and (B) IND9-14. The α7-nAChR functional assays were done in the presence of 10 µM PNU-120596. FRET ratios were normalized to the maximum response by 100 nM (±)-epibatidine. The family of curves are all step showing Hill coefficients ~2, but because of the limited concentration points and rapid responses, we have not analyzed Hill coefficients for this sample number.

Figure 8:
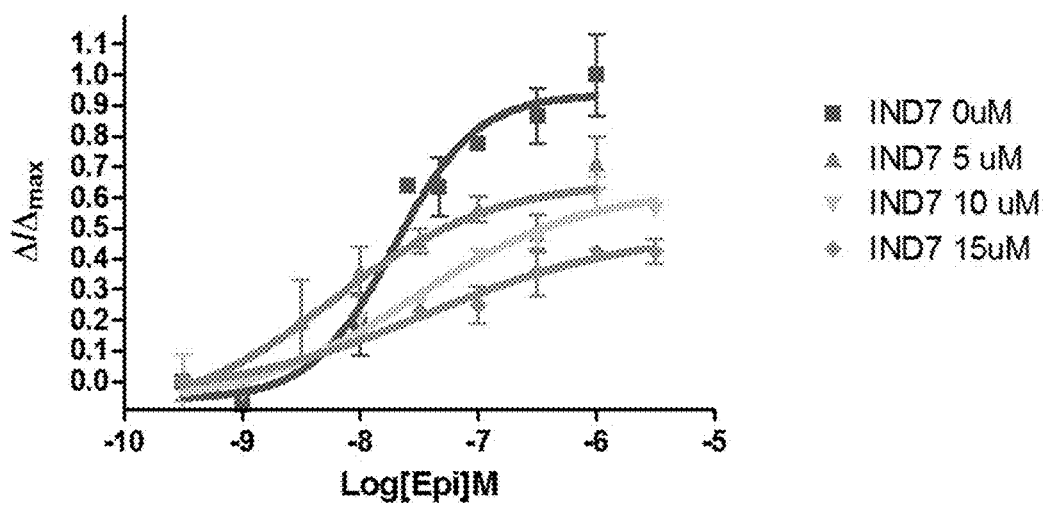
FIG. 8 and FIG. 9 graphically illustrate data showing: for α4β2-nAChRs, only for IND7 (FIG. 8) and IND8 (FIG. 9) did the functional results did not correlate with those from binding assay, similar to TTIn-1.
Figure 9:
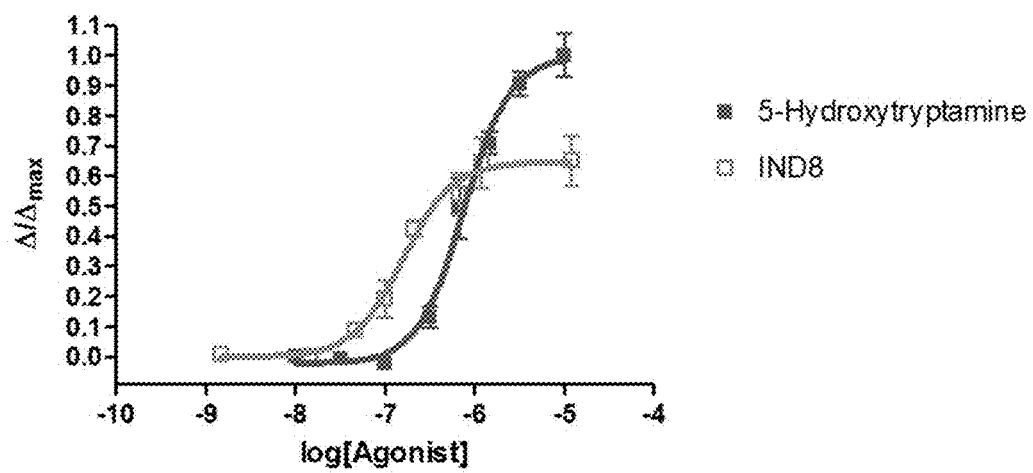
Figure 10A:
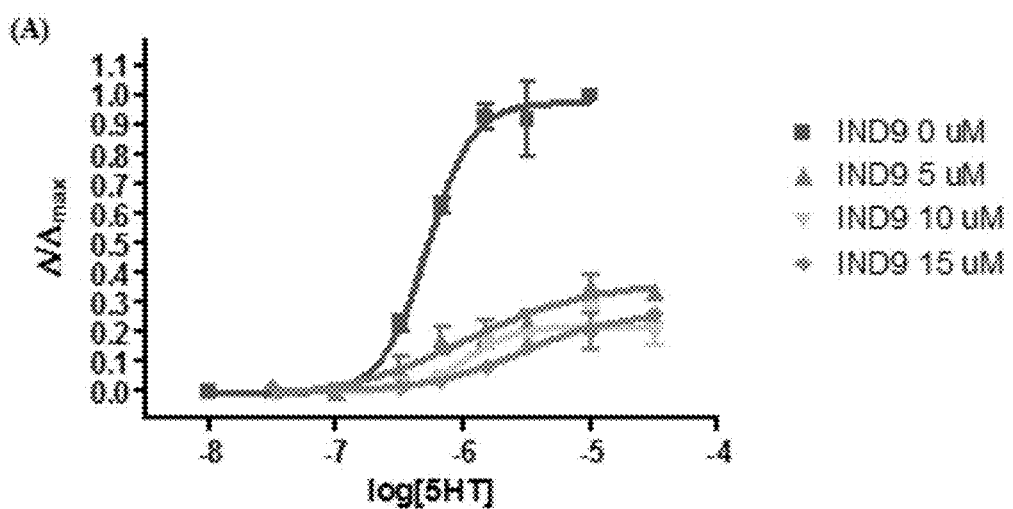
FIG. 10A, FIG. 10B, FIG. 10C and FIG. 10D graphically illustrate 5HT$_{3A}$ receptor agonist and antagonist dose-response curves showing the 5HT$_{3A}$ functional results of eight compounds from fourteen compounds did not correlate well with the results from binding affinity testing: IND1, IND2, and IND7 can bind to $5HT_{3A}$ receptors, but their agonist and antagonist responses were not observed; four compounds: IND9 (FIG. 10A), IND10 (FIG. 10B), IND12 (FIG. 10C), IND14 (FIG. 10D) demonstrated better $5HT_{3A}$ antagonism than TTIn-1; and one compound (IND8) is a $5HT_{3A}$ partial agonist ($EC_{50}=0.21$ μM)
Figure 10B:
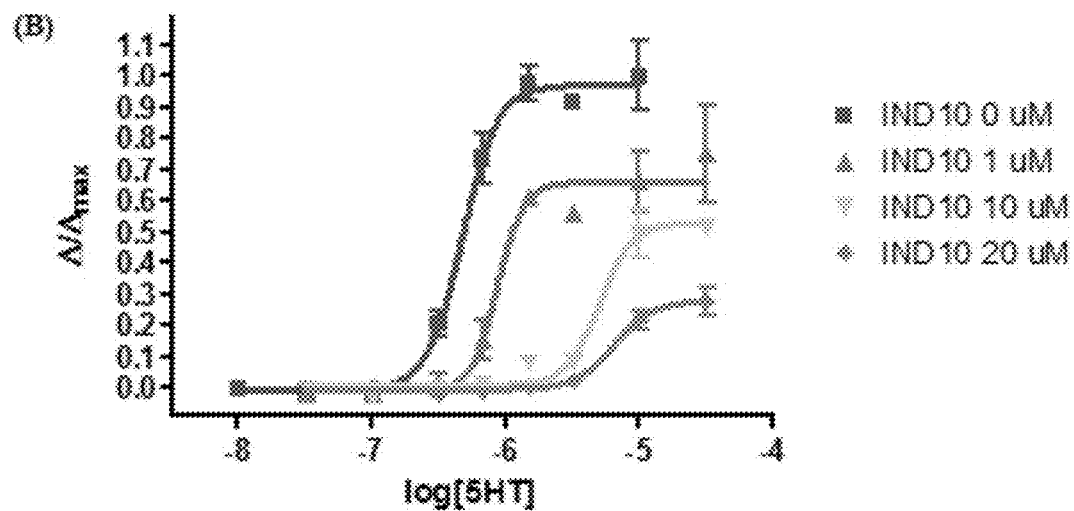
Figure 10C:
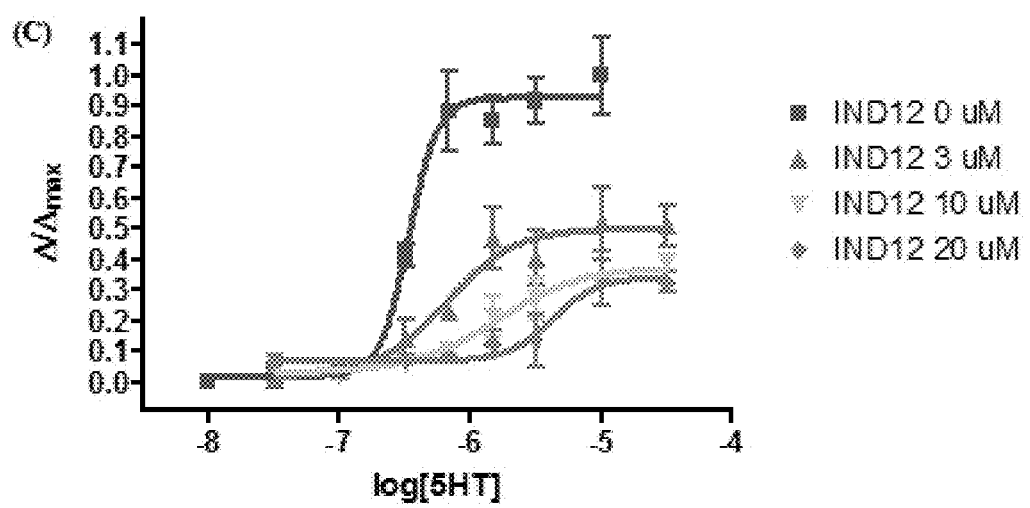
Figure 10D:
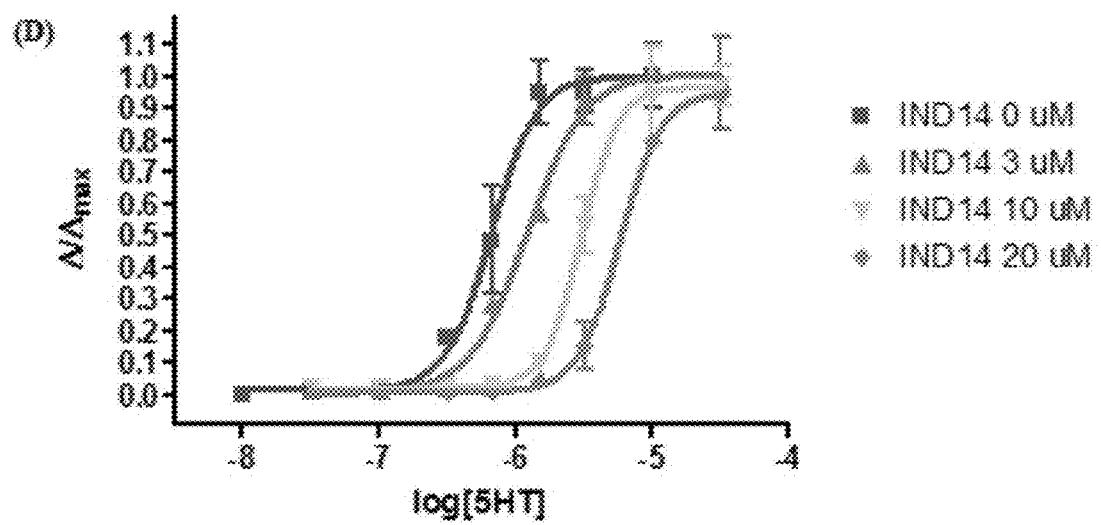
Figure 11A:
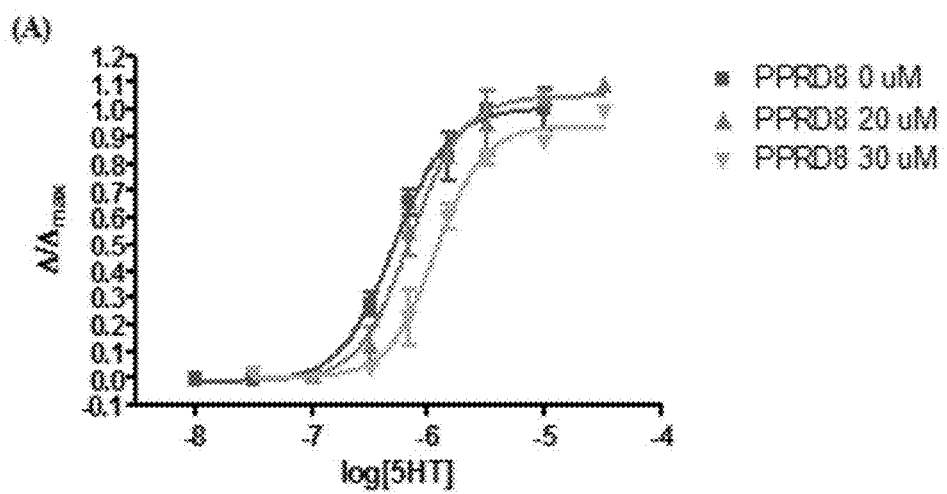
FIG. 11A, FIG. 11B, FIG. 11C, FIG. 11D and FIG. 11E graphically illustrate data showing that the potency of modified compounds in the exemplary PPRD series of compounds as provided herein are in agreement with their binding affinity: compounds containing H-bond donor as substituent (PPRD2 and PPRD8) have the highest agonist potency to α7-nAChRs with $EC_{50}$ values of 0.38 μM and 2.9 μM, respectively; additional substitution to form a methyl ester causes steric hindrance; therefore, the potency of PPRD14 ($EC_{50}>10$ μM) and PPRD15 ($EC_{50}=3.1$ μM) decreased compare to their corresponding mono-substitution compounds, PPRD8 and PPRD2 ($EC_{50}=2.9$ and 0.38 μM); PPRD3 with a methoxy substitution and PPRD13 with chloro substitution appeared to be partial agonists at α7-nAChRs with moderate potency ($EC_{50}=15$ and 17.8 μM, respectively). The α7-nAChR dose-response curves are shown in FIG. 5A; three compounds from this modified series also show competitive antagonism properties to $5HT_{3A}$ receptors i.e. PPRD8, PPRD14, and PPRD15 ($K_d=39$, 1.44, and 6.0 μM, respectively)
Figure 11B:
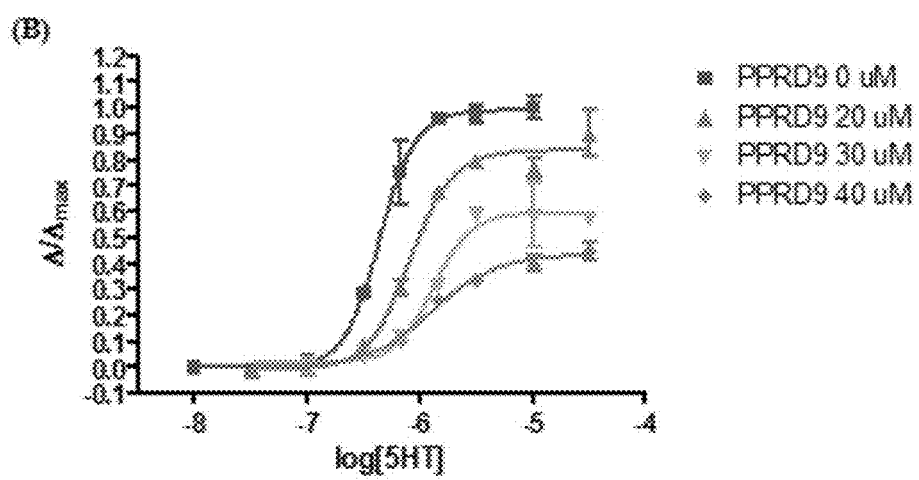
Figure 11C:
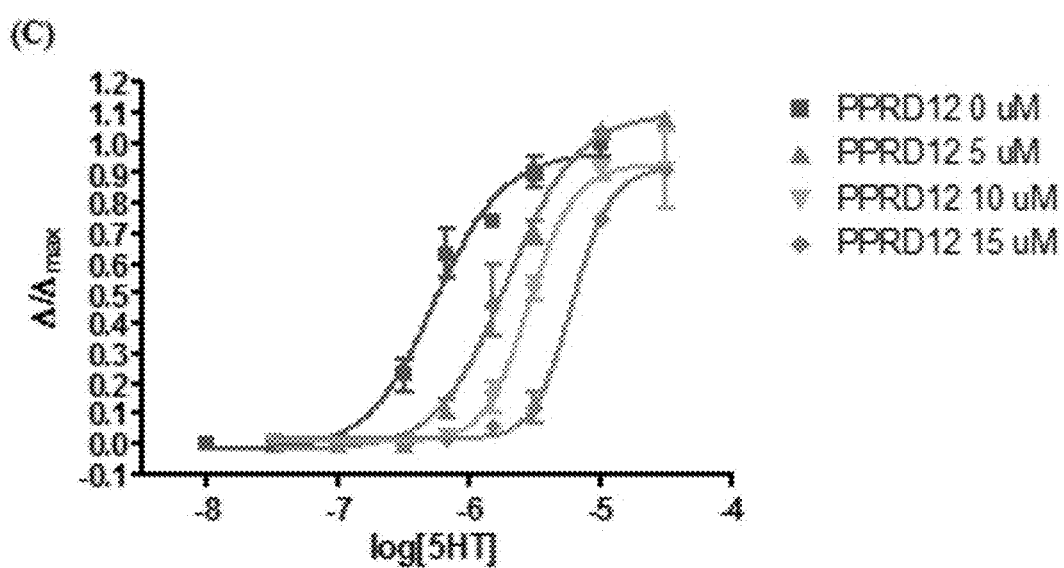
Figure 11D:
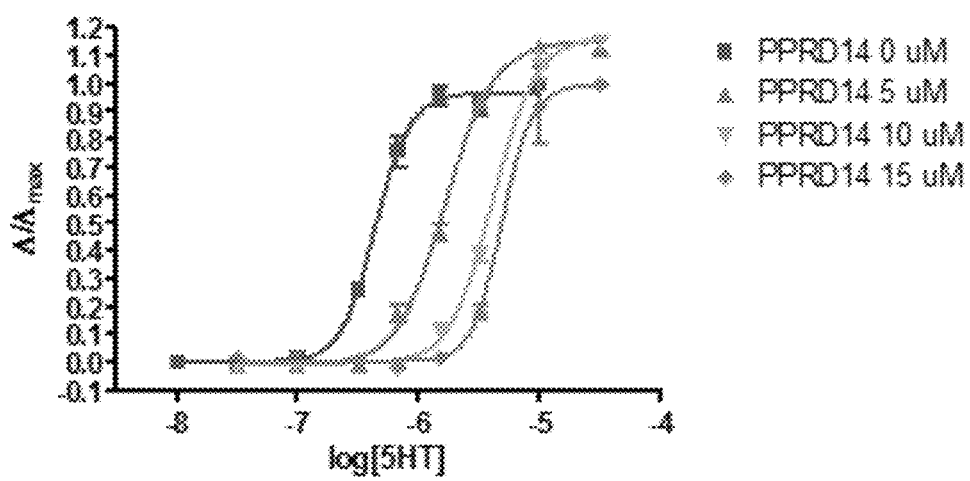
Figure 11E:
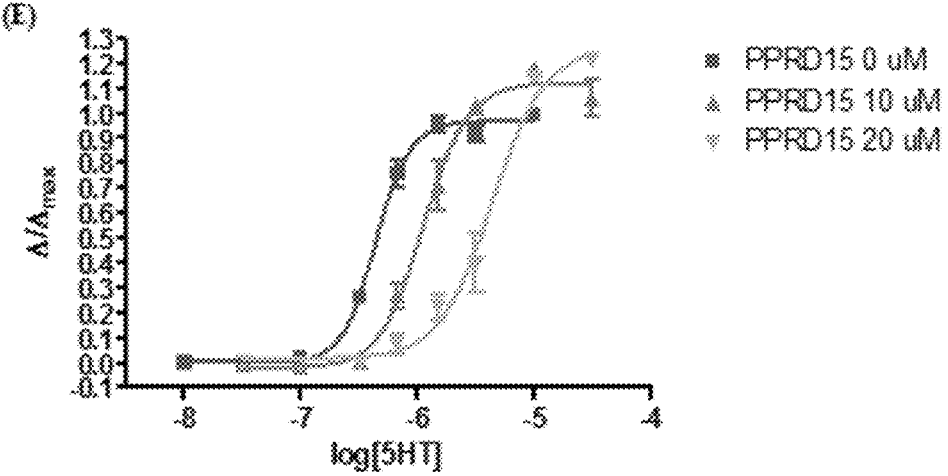
Figure 12A:
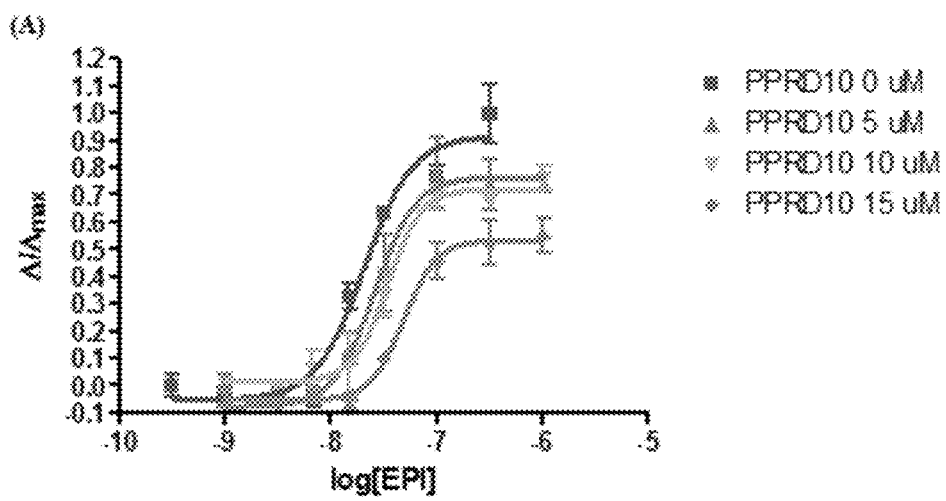
FIG. 12A, FIG. 12B, FIG. 12C and FIG. 12D graphically illustrate data showing α7-nAChR antagonist of the exemplary PPRD10 (FIG. 12A), PPRD11 (FIG. 12B), PPRD12 (FIG. 12C) and QND7 (FIG. 12D): the steric hindrance from additional methyl ester substituent in QND15 decreased α7-nAChR agonist potency ($EC_{50}=1.34$ μM) while the more bulky biphenyl group turned QND7 into a weak α7-nAChR antagonist (FIG. 12D), and a change in position of the H-bond donor by reversing the indole turned PPRD11 (FIG. 12B) and PPRD12 (FIG. 12C) into weak and non-selective α7-nAChR antagonists, as further described in Example 1, below.
Figure 12B:
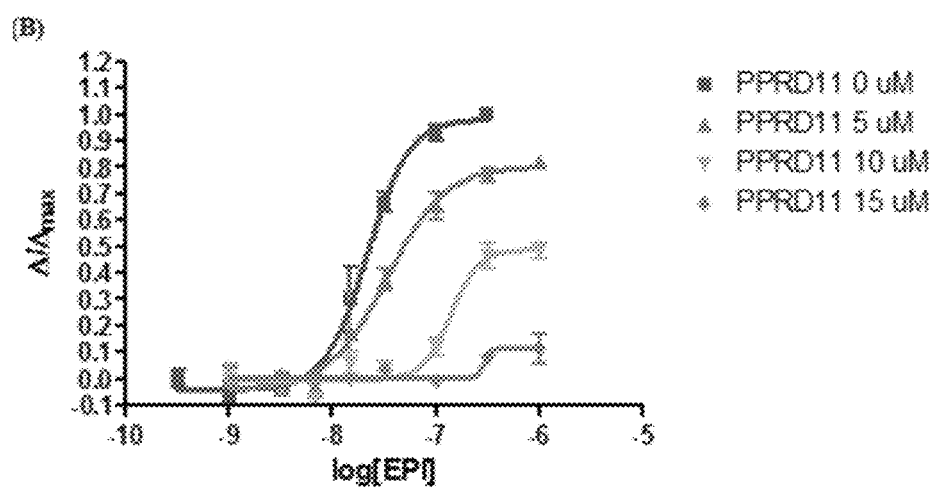
Figure 12C:
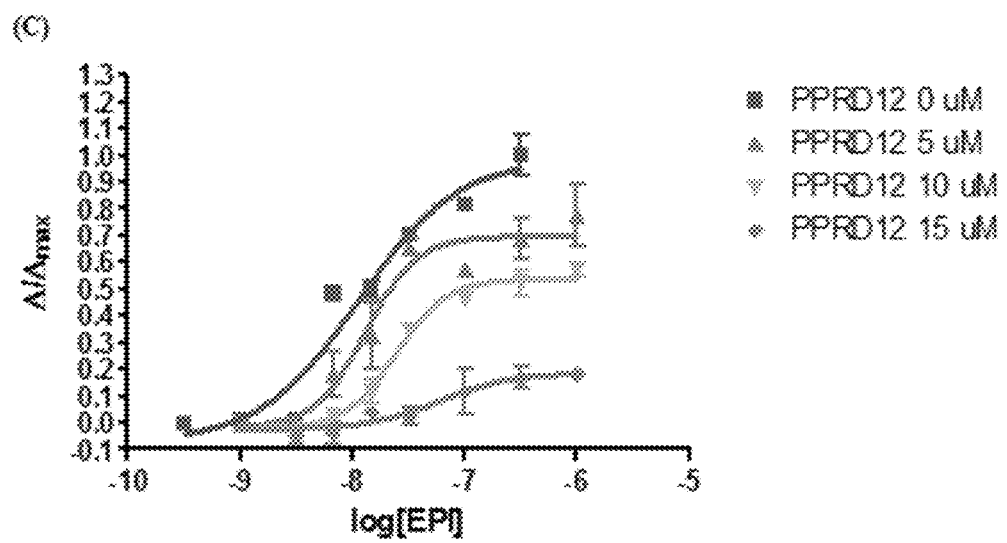
Figure 12D:
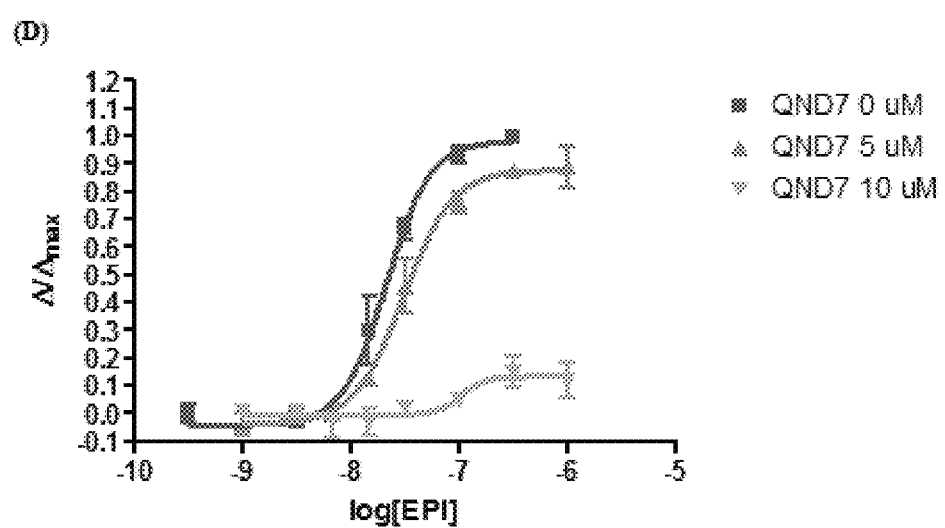
Figure 13A:
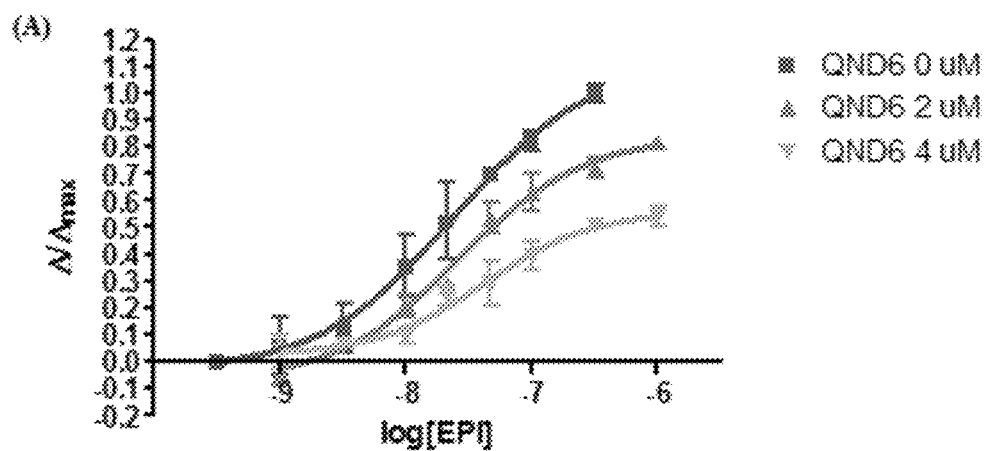
FIG. 13A, FIG. 13B, FIG. 13C, FIG. 13D, FIG. 13E and FIG. 13F graphically illustrate data showing α4β2 nAChR antagonist dose-response curves of the exemplary QND series compounds as provided herein.
Figure 13B:
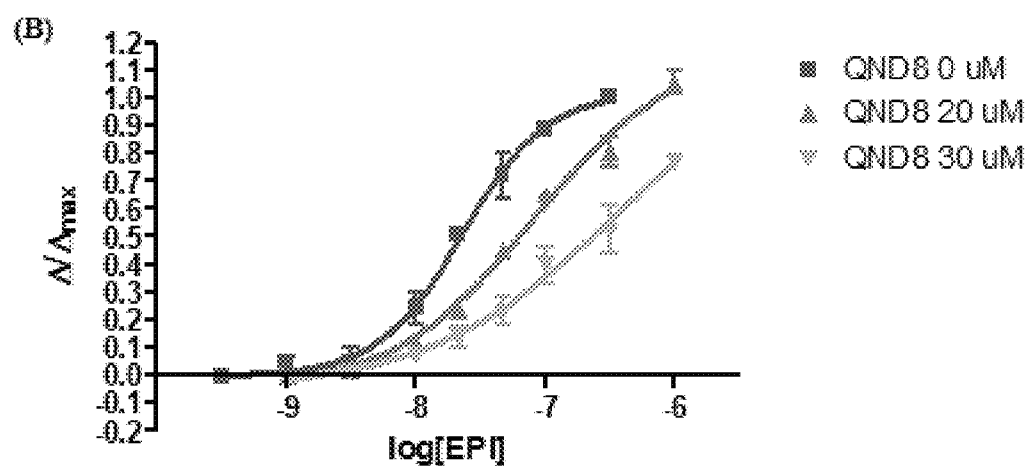
Figure 13C:
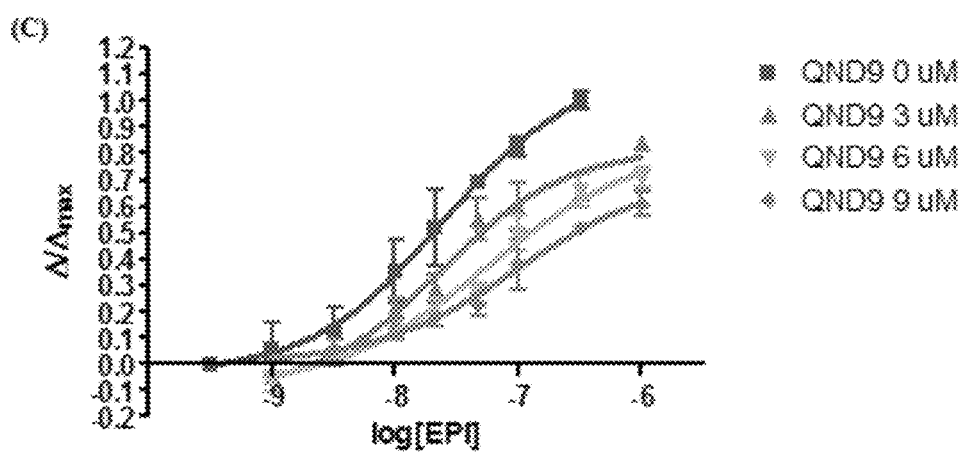
Figure 13D:
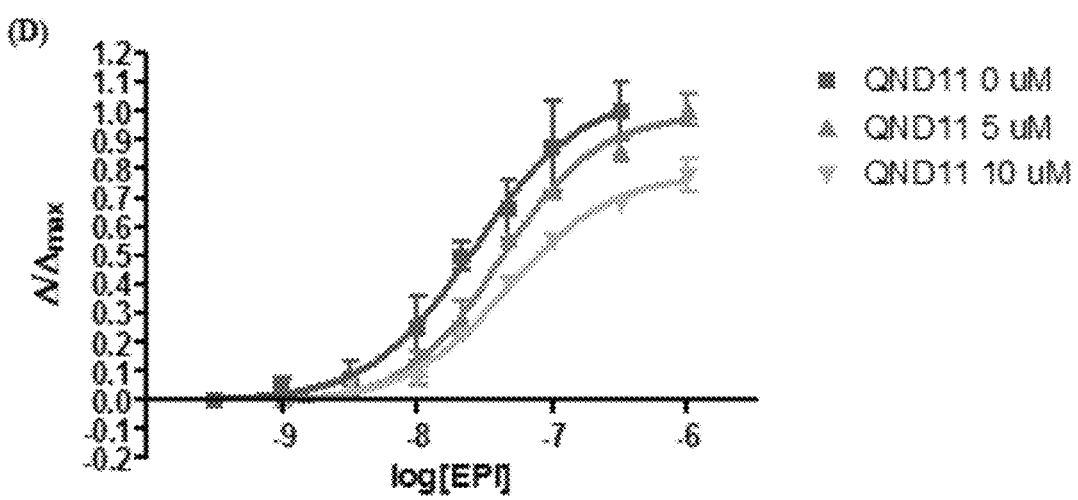
Figure 13E:
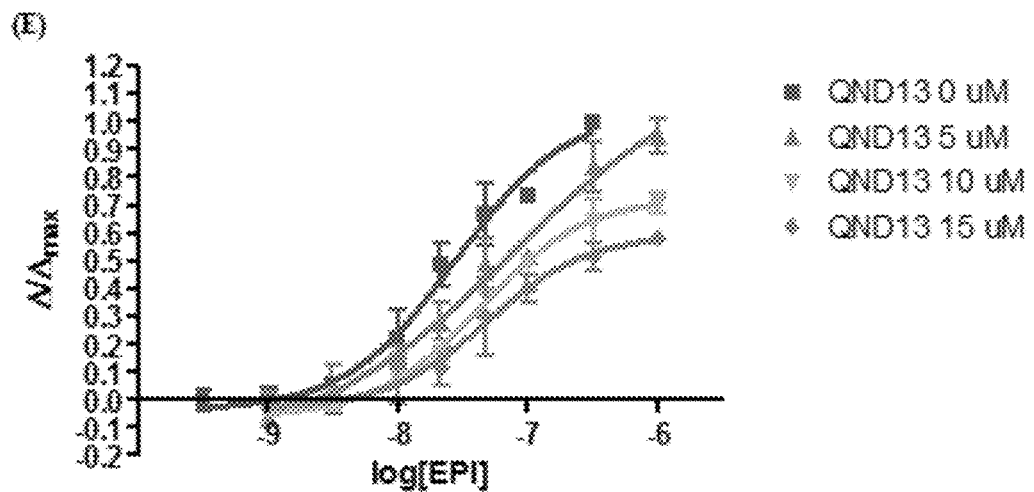
Figure 13F:
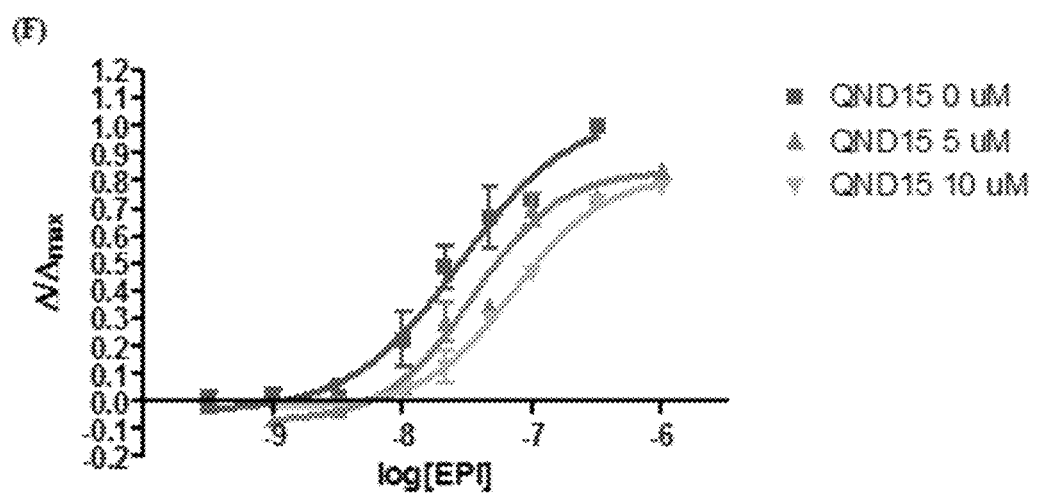

FIG. 8 and FIG. 9 graphically illustrate data showing: for α4β2-nAChRs, only for IND7 (FIG. 8) and IND8 (FIG. 9) the functional results did not correlate with those from binding assay, similar to TTIn-1. As illustrated in FIG. 8, IND7 poorly bound to α4β2-nAChRs and showed non-competitive antagonism with low potency profiles ($K_A$=22.16$^{NC}$ µM). In contrast, illustrated in FIG. 9, IND8 showed higher affinity binding to α4β2-nAChRs and did not elicit agonist or antagonist properties in assaying cation permeability of the intact cells.

The 5HT$_{3A}$ functional results of eight compounds from fourteen compounds did not correlate well with the results from binding affinity testing. Some compounds i.e. IND1, IND2, and IND7 can bind to 5HT$_{3A}$ receptors, but their agonist and antagonist responses were not observed. Four compounds (IND9-10, 12, 14) demonstrated better 5HT$_{3A}$ antagonism than TTIn-1 and interestingly, one compound (IND8) turns to be 5HT$_{3A}$ partial agonist (EC$_{50}$=0.21 µM). The 5HT$_{3A}$ receptor agonist and antagonist dose-response curves are shown in FIG. 10.

The significant improvement of selectivity and potency profiles of IND1 and IND8 over the lead compound indicates that the 3.7-3.8 Å is the optimal distance between the basic nitrogen atom and the triazole ring for the α7-nAChR agonist activity. IND1, a six-membered monocyclic ring with a 2 methylene linker, is the most potent α7-nAChR agonist (EC$_{50}$=0.17 µM) and highly selective for that receptor subtype over the α4β2-nAChR, and 5HT$_{3A}$ receptor. IND8, a bicyclic amine, is the most potent compound in the series (EC$_{50}$=0.03 µM), but with a diminished degree of selectivity. Therefore, the piperidine and quinuclidine rings from IND1 and IND8 representing mono- and bicyclic rings were selected as the cation center (R$_1$) for further modification of the hydrophobic R$_2$ in the second compound set, PPRD and QND series, respectively.

2) Variation in Hydrophobic Indole Substitution of the Triazole (PPRD and QND Series)

2.1) Effect on Binding Affinity (K$_d$)

Figure 33:
FIG. 33 illustrates Table 2 of Example 1, which shows the $K_d$ values of compounds in PPRD and QND series from whole cell binding assay using LGIC-CNiFERs; from the screening results of the second compound set, nine compounds from PPRD series and twelve compounds from QND series passed the initial screening for the binding to α7-nAChRs; $K_d$ values of all compounds which passed the initial screening with Cys-loop ligand-gated ion channel (LGIC) receptors, as further described in Example 1, below.

From the screening results of the second compound set, nine compounds from PPRD series and twelve compounds from QND series passed the initial screening for the binding to α7-nAChRs. All compounds exhibited α7-nAChR selectivity over α4β2-nAChRs, except QND6 and 9 that associate well with cα4β2-nAChRs. Only two compounds in PPRD series, but eleven from QND series interact with 5HT$_{3A}$ receptors. The modified compounds from QND series have higher affinity than the corresponding compounds in PPRD series for both c 7-nAChRs and 5HT$_{3A}$ receptors. K$_d$ values of all compounds which passed the initial screening with LGIC receptors are shown in Table 2 (FIG. 33), where: K$_d$>10 µM was indicated in the compounds that did not pass the initial screen. K$_d$ of TTIn-1 is 4.2 µM for α7-nAChRs, >10 µM for α4β2-nAChRs, and 6.0 µM for 5HT$_{3A}$ receptors. For Table 2 (FIG. 33), R1 and R2 are:

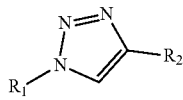

(i) Simple Benzene Ring with Mono- and Di-Substitution

The binding affinity to α7-nAChRs of compounds which one substituent on benzene ring is a H-bond donor appeared to be greater than those bearing a H-bond acceptor or heteroatom. The K$_d$ values of PPRD2 bearing amino group and PPRD8 bearing hydroxyl group which are H-bond donors were less than 7.35 µM. The explanation from this result is that the —NH$_2$ and —OH are bioisostere of the —NH of indole. However, the binding affinity of PPRD2 and 8 are not as good as IND1. This might come from the lower hydrophobicity (log P) of PPRD2 and 8 together with less electron cloud over benzene ring comparing to indole ring to stabilize the hydrophobic interaction in the binding pocket. The compound having biphenyl group (PPRD7) cannot bind to all tested LGIC receptors because the steric biphenyl moiety cannot be accommodated in the binding pocket. A decrease of binding affinity from steric hindrance is also observed in compounds bearing benzene ring with two substituents, PPRD14 (K$_d$>10 µM) and PPRD15 (K$_d$=4.4 µM) comparing to PPRD8 and 2, their corresponding compounds with mono-substitution. The modified compounds in PPRD and QND series were generally selective for α7-nAChRs.

For QND series with R$_1$ of IND8, the binding affinity for α7-nAChRs of six compounds where the indole was replaced by simple benzene ring with mono- and di-substitution are higher than that of TTIn-1. The K$_d$ value of QND8 which the mono-substituent on benzene ring is hydroxyl group acting as H-bond donor as —NH of indole was found to be the lowest (0.08 µM) and better than IND8. The lowest K$_d$ values of QND8 supported the essential role of H-bond donor in the binding mode of α7-nAChRs. Other mono-substituents on benzene ring i.e. QND2 bearing amino group, QND3 bearing methoxy group, QND4 bearing methyl group, and QND13 bearing chloro group have enhanced binding affinities for α7-nAChRs between 0.20-0.36 µM. The switch of indole to biphenyl group (QND7) reduces the binding to all tested receptors as seen in the in PPRD series. Addition of second substituent (—COOCH$_3$) to the structure, giving QND15 (K$_d$=3.61 µM) whose affinity for α7-nAChRs is 10-fold lower than its corresponding QND2. The lower affinity might come from the ester group that causes steric hindrance or the inappropriate distance to interact with amino acid residues in the hydrophobic region. Most compounds in QND series that bind to α7-nAChRs show binding to 5HT$_{3A}$ receptors with K$_d$ in the range of 0.05-2.3 µM. The ester extension of QND15 increases the binding affinity to 5HT$_{3A}$ receptor (K$_d$=0.04 µM). The nAChR affinity is higher than QND2, its corresponding structure (K$_d$=1.21 µM) and equivalent to IND8 (K$_d$=0.05 µM).

(ii) Bicyclic Amine Systems

The binding affinity to all tested LGIC receptors of compounds in PPRD series that contain steric bicyclic systems i.e. indole modification, 1,3-benzodioxole, 2-methoxynaphthalene, and adenine apparently decreased when comparing with IND1. Methylation of indole ring in PPRD9 decreases the binding affinity to α7-nAChRs (K$_d$=12.14 µM). This result supports the notion that the —NH of indole ring acts as H-bond donor in the binding pocket. Addition of carbonyl group in the indole ring causes steric hindrance in the binding pocket leading to the lower affinity of PPRD5 (K$_d$=3.27 µM) than IND1. Changing the —NH indole orientation in the structures of PPRD11 and PPRD12 resulted in a reduction of binding affinity to α7-nAChRs. This might come from unflavored position of indole —NH to afford the interaction with amino acid residues in the binding pocket. Bicyclic substitutions increase α7-nAChRs selectivity except for PPRD12 that can interact with 5HT$_{3A}$ receptor (K$_d$=2.55 µM).

For the QND series, the affinity to α7-nAChRs of all compounds in this series is lower than IND8 except for QND1 (K$_d$=0.16 µM) whose binding affinity is similar to IND8 (K$_d$=0.12 µM). Again, methylation of indole ring and changing the position of the —NH indole orientation led to a lower binding affinity as seen by 15-fold and 9-fold increases of K$_d$ of QND9 (K$_d$=1.88 µM) and QND12 (K$_d$=0.92 µM), respectively when compared to IND8. Steric hindrance caused by methyl ester substitution on an indole ring (QND5, 11) or methoxy substitution on a naphthalene ring (QND6) reduces the affinity to α7-nAChRs from $K_d$ of 0.1 μM level to higher than 2 μM. Only two compounds, QND6 and 9, showed similar affinities for α4β2-nAChRs as IND8. All modified compounds bind to $5HT_{3A}$ receptors except for QND6. QND1 and QND12 ($K_d$=0.02-0.05 μM) showed increased affinity for $5HT_{3A}$ receptors as IND8. The orientation of indole influences $5HT_{3A}$ receptor binding affinity as observed by the lower $K_d$ for PPRD12 ($K_d$=2.6 μM) and QND12 ($K_d$=0.02 μM), when compared with IND1 ($K_d$=5.52 μM) and IND8 ($K_d$=0.05 μM), respectively.

The nitrogen-rich adenine at $R_2$ in PPRD and QND10 repelled the side chains from aromatic nest when are also electron rich. They show minimal association with the aromatic side chains.

are α7-nAChR agonists, whereas three compounds (PPRD10-12) turn out to be α7-nAChR antagonists. The modified compounds have lower α7-agonist potencies than IND1. The $EC_{50}$ and $K_A$ values of PPRD series are shown in Table 3. Two compounds (PPRD9, 11) acted as α4β2-nAChR antagonists and five compounds (PPRD8-9, 12, 14-15) are $5HT_{3A}$ receptor antagonists. The PPRD7 containing steric biphenyl moiety did not pass the functional screening to all Cys-loop ligand-gated ion channel (LGIC) receptors. For QND series, the $EC_{50}$ and $K_A$ values are shown in Table 4. Thirteen compounds (QND1-6, 8-13, 15) showed agonistic properties except for QND7 that showed antagonistic properties to α7-nAChRs. Six compounds (QND6, 8-9, 11, 13, 15) are α4β2-nAChR antagonists. Nine

TABLE 3

The $EC_{50}$ and $K_A$ values of PPRD series.

| Compound | Agonist $EC_{50} \pm SD$ (μM) | | Antagonist $K_A \pm SD$ (μM) | | |
|---|---|---|---|---|---|
| | α7 | $5HT_{3A}$ | α7 | α4β2 | $5HT_{3A}$ |
| IND1 | 0.17 ± 0.05 | >10 | — | >10 | >10 |
| PPRD1 | 7.4 ± 0.7 | >10 | — | >10 | >10 |
| PPRD2 | 0.38 ± 0.08 | >10 | — | >10 | >10 |
| PPRD3 | 15.0 ± 0.1* | >10 | — | >10 | >10 |
| PPRD4 | 3.1 ± 0.8 | >10 | — | >10 | >10 |
| PPRD5 | 1.05 ± 0.17 | >10 | — | >10 | >10 |
| PPRD6 | >10 | >10 | — | >10 | >10 |
| PPRD7 | >10 | >10 | — | >10 | >10 |
| PPRD8 | 2.9 ± 0.7 | — | — | >10 | 39.0 ± 2.1[C] |
| PPRD9 | 12.9 ± 4.6* | — | — | 10.5 ± 3.1[C], 25.5 ± 12.8[NC] | 15.1 ± 4.0[C], 56.0 ± 31.0[NC] |
| PPRD10 | >10 | >10 | 11.6 ± 3.5[C], 18.9 ± 9.4[NC] | >10 | >10 |
| PPRD11 | — | >10 | 6.6 ± 2.2[C], 6.6 ± 1.7[NC] | 6.5 ± 1.7[C] | >10 |
| PPRD12 | — | — | 4.5 ± 1.5[C], 11.3 ± 4.5[NC] | >10 | 2.1 ± 0.3[C] |
| PPRD13 | 17.6 ± 4.6* | >10 | — | >10 | >10 |
| PPRD14 | >10.0 | — | >10 | >10 | 1.4 ± 0.1[C] |
| PPRD15 | 3.1 ± 0.2 | — | — | >10 | 6.0 ± 1.5[C] |

Data were averaged from at least three independent experiments. All values are reported as means ± SD. $EC_{50}$ and $K_A$ > 10 μM were indicated in the compounds that did not pass the initial screen.
*Partial agonist;
[C]competitive antagonist;
[NC]non-competitive antagonist.
Values are calculated as described in methods.

2.1) Effect of the Hydrophobic Moiety on Agonist and Antagonist Activity.

The results from functional screening with LGIC receptors revealed that nine compounds (PPRD1-5, 8-9, 13, 15) compounds (QND1-3, 5, 8-9, 12-13, 15) are $5HT_{3A}$ receptor agonists, whereas two compounds (QND4, 11) are antagonists. The compounds in QND series have higher α7-nAChR agonist potencies than PPRD series.

TABLE 4

The $EC_{50}$ and $K_A$ values of QND series.

| Compound | Agonist $EC_{50} \pm SD$ (μM) | | Antagonist $K_A \pm SD$ (μM) | | |
|---|---|---|---|---|---|
| | α7 | $5HT_{3A}$ | α7 | α4β2 | $5HT_{3A}$ |
| IND8 | 0.03 ± 0.01 | 0.21 ± 0.08* | — | >10 | — |
| QND1 | 0.12 ± 0.04 | 0.30 ± 0.04* | — | >10 | — |
| QND2 | 0.05 ± 0.02 | 1.63 ± 0.29* | — | >10 | — |
| QND3 | 0.10 ± 0.03 | 5.7 ± 1.7* | — | >10 | — |
| QND4 | 0.20 ± 0.08 | — | — | >10 | 0.50 ± 0.27[C], 0.53 ± 0.18[NC] |
| QND5 | 0.27 ± 0.00 | 0.16 ± 0.04* | — | >10 | — |
| QND6 | 22 ± 6* | >10 | — | 7.0 ± 4.5[C], 6.2 ± 0.4[NC] | >10 |

TABLE 4-continued

The $EC_{50}$ and $K_A$ values of QND series.

| Compound | Agonist $EC_{50} \pm$ SD (μM) | | Antagonist $K_A \pm$ SD (μM) | | |
|---|---|---|---|---|---|
| | α7 | $5HT_{3A}$ | α7 | α4β2 | $5HT_{3A}$ |
| QND7 | — | >10 | $6.7 \pm 2.5^C$, $26 \pm 10^{NC}$ | >10 | >10 |
| QND8 | 0.04 ± 0.01 | 0.90 ± 0.09* | — | $6.2 \pm 1.7^C$ | — |
| QND9 | 1.00 ± 0.04 | 1.38 ± 0.52 | — | $5.2 \pm 1.2^C$, $6.5 \pm 0.2^{NC}$ | — |
| QND10 | 30 ± 7.5* | >10 | — | >10 | >10 |
| QND11 | 1.61 ± 0.36 | — | — | $9.3 \pm 4.3^C$, $37 \pm 22^{NC}$ | $0.08 \pm 0.01^{NC}$ |
| QND12 | 0.45 ± 0.14 | 0.34 ± 0.13* | — | >10 | — |
| QND13 | 1.01 ± 0.33 | 4.9 ± 1.2 | — | $11.2 \pm 2.6^C$, $23 \pm 6^{NC}$ | — |
| QND15 | 1.34 ± 0.01 | 0.26 ± 0.03* | — | $11.6 \pm 1.0^C$ | — |

Data were averaged from at least three independent experiments. All values are reported as means ± SD. $EC_{50}$ and $K_A$ > 10 μM were indicated in the compounds that did not pass the initial screening.
*indicates partial agonist;
$^C$indicates competitive antagonist;
$^{NC}$indicates non-competitive antagonist.
Values are calculated as described in methods.

(i) Mono- and Di-Substituted Phenyl

Figure 5A:
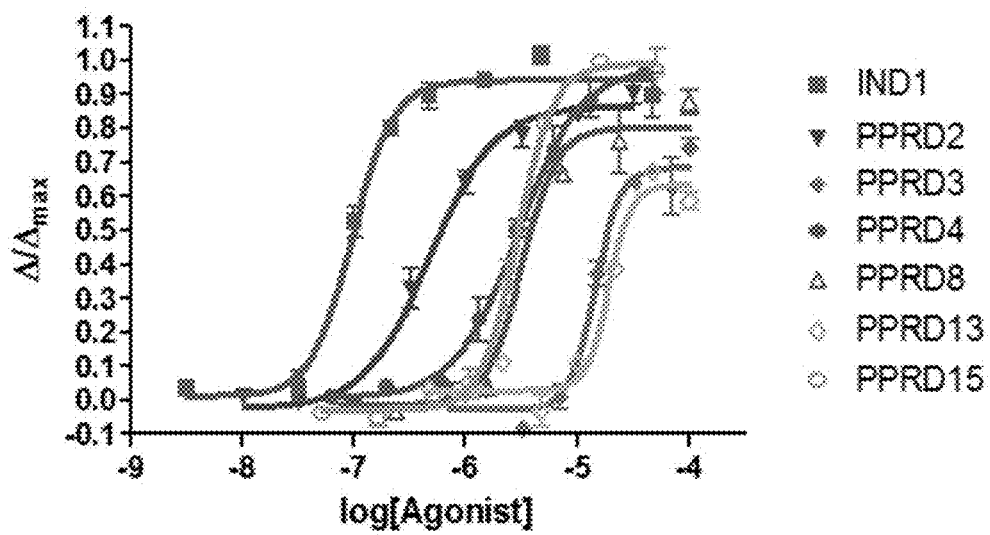

The potency of modified compounds in PPRD series are in agreement with their binding affinity. Compounds containing H-bond donor as substituent (PPRD2 and PPRD8) have the highest agonist potency to α7-nAChRs with $EC_{50}$ values of 0.38 μM and 2.9 μM, respectively. Additional substitution to form a methyl ester causes steric hindrance; therefore, the potency of PPRD14 ($EC_{50}$>10 μM) and PPRD15 ($EC_{50}$=3.1 μM) decreased compare to their corresponding mono-substitution compounds, PPRD8 and PPRD2 ($EC_{50}$=2.9 and 0.38 μM). PPRD3 with a methoxy substitution and PPRD13 with chloro substitution appeared to be partial agonists at α7-nAChRs with moderate potency ($EC_{50}$=15 and 17.8 μM, respectively). The α7-nAChR dose-response curves are shown in FIG. 5A. Three compounds from this modified series also show competitive antagonism properties to $5HT_{3A}$ receptors i.e. PPRD8, PPRD14, and PPRD15 ($K_A$=39, 1.44, and 6.0 μM, respectively), see FIG. 11.

FIG. 5. α7-nAChR agonist dose-response curves of mono- and di-substituted of phenyl ring for (A) PPRD and (B) QND series. The assays were performed in the presence of 10 μM PNU-120596. FRET ratios were normalized to the maximum response by 100 nM (±)-epibatidine.

Figure 5B:
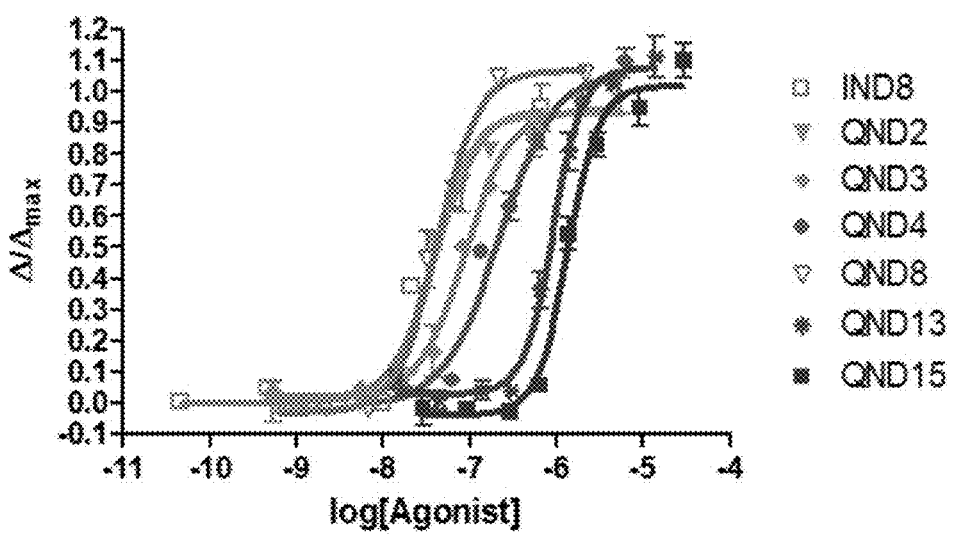

The α7-nAChR dose-response curves of compounds in QND series are shown in FIG. 5B. For QND series, the rank order of α7-agonistic potency for the phenyl ring compounds in follows the order binding affinity ranking. The potency of QND8 ($EC_{50}$=0.04 μM) and QND2 ($EC_{50}$=0.05 μM) is comparable to IND8 ($EC_{50}$=0.03 μM) which underscores the importance of a H-bond donor in the hydrophobic region for α7-nAChRs. QND3 ($EC_{50}$=0.10 μM) with oxygen atom of methoxy substituent that can act as H-bond acceptor has higher potency than compounds having methyl substituent (QND4, $EC_{50}$=0.20 μM) or chloro substituent (QND13, $EC_{50}$=1.01 μM).

The steric hindrance from additional methyl ester substituent in QND15 decreased α7-nAChR agonist potency ($EC_{50}$=1.34 μM) while the more bulky biphenyl group turned QND7 into a weak α7-nAChR antagonist (FIG. 12).

Three compounds (QND8, 13, 15) from this series showed moderate to low antagonist potencies for α4β2-nAChRs (FIG. 13).

Figure 14:
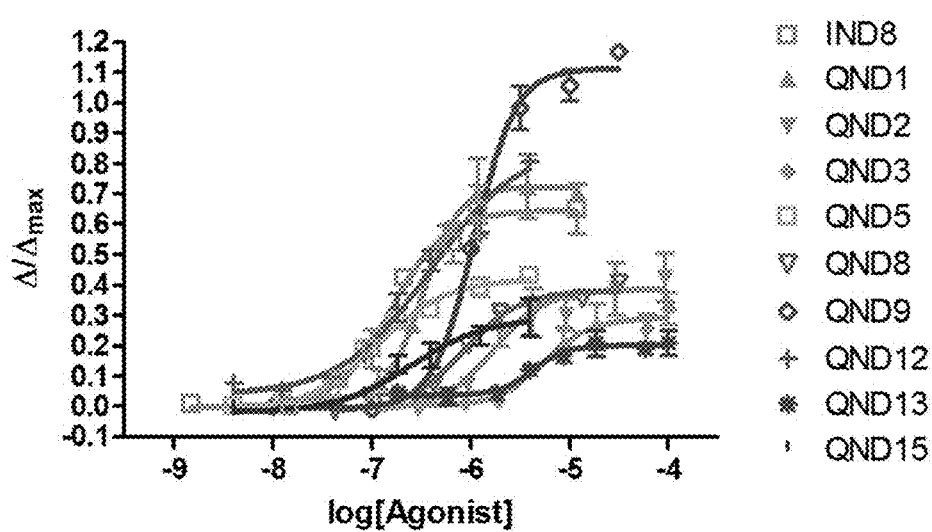
FIG. 14 graphically illustrates $5HT_{3A}$ receptor agonist characterization of the exemplary QND series of compounds as provided herein including the exemplary IND8, QND1, QND2, QN3, QND5, QND8, QND9, QND12, QND13, and QND15; as further described in Example 1, below.
Figure 15A:
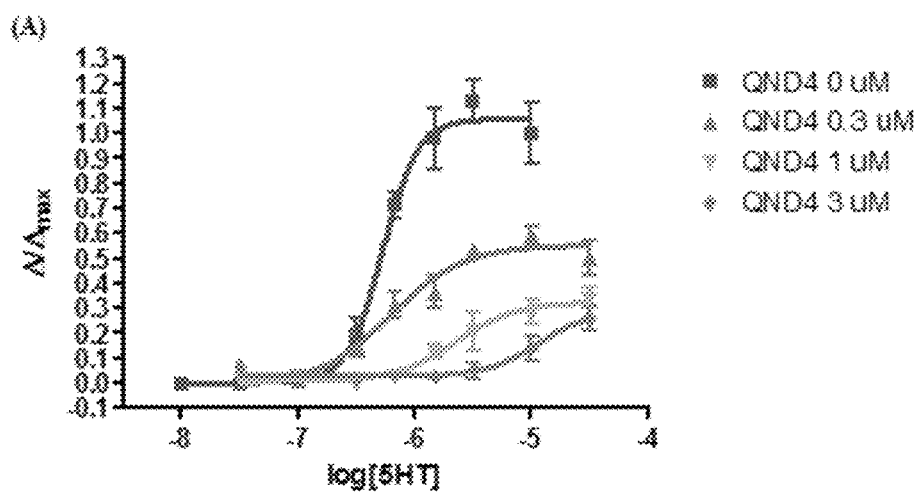
FIG. 15A and FIG. 15B graphically illustrate $5HT_{3A}$ receptor antagonist dose-response curves of the exemplary QND series of compounds as provided herein including the exemplary.
Figure 15B:
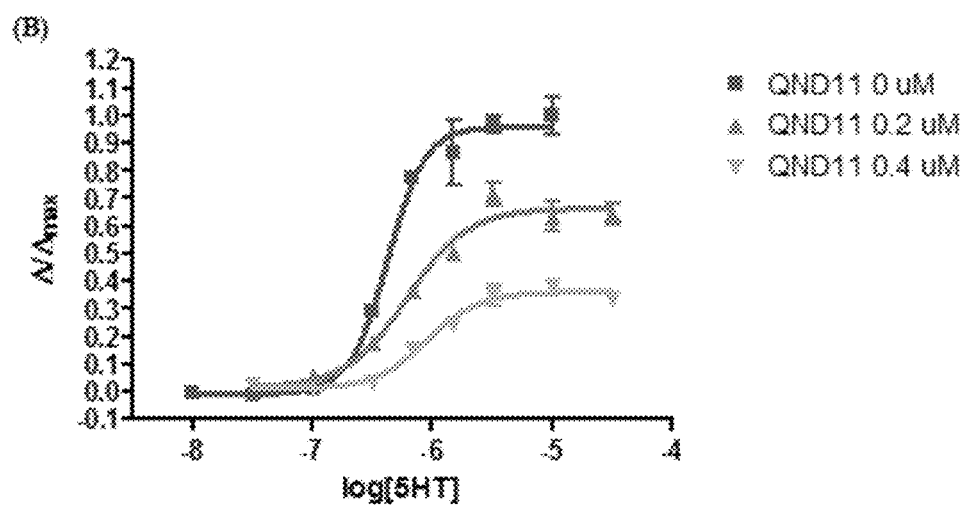

Interestingly, all compounds having heteroatom substitution at para-position (QND2, 3, 8, 13, 15) have $5HT_{3A}$ receptor agonist properties in contrary to the $5HT_{3A}$ antagonist properties of TTIn-1 and QND4 (FIG. 14 and FIG. 15). The heteroatom substitution at this position might play an important role in the interaction with amino acid residues in the binding pocket of $5HT_{3A}$ receptors.

(i) Bicyclic Amines

Figure 6A:
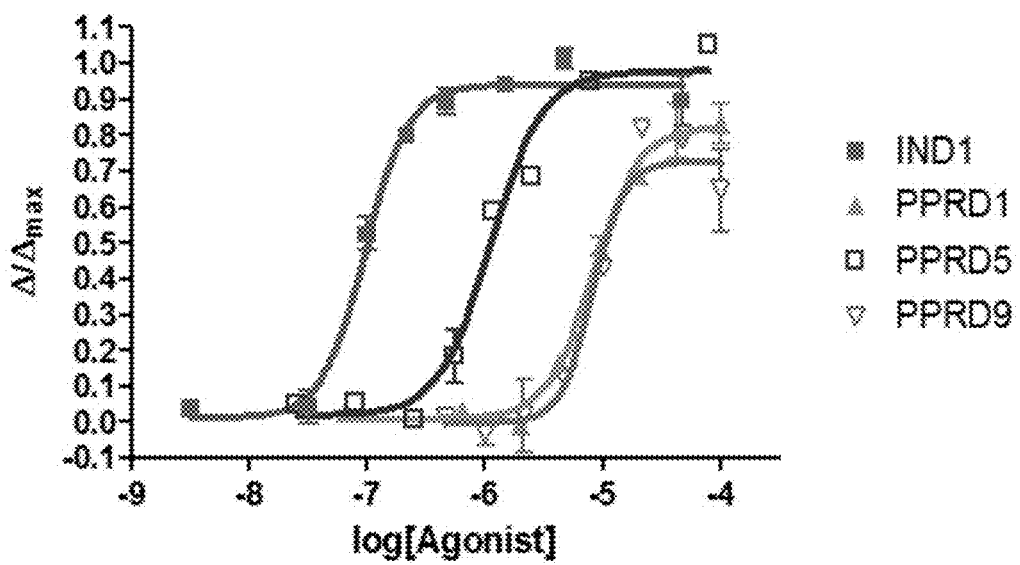
Figure 16A:
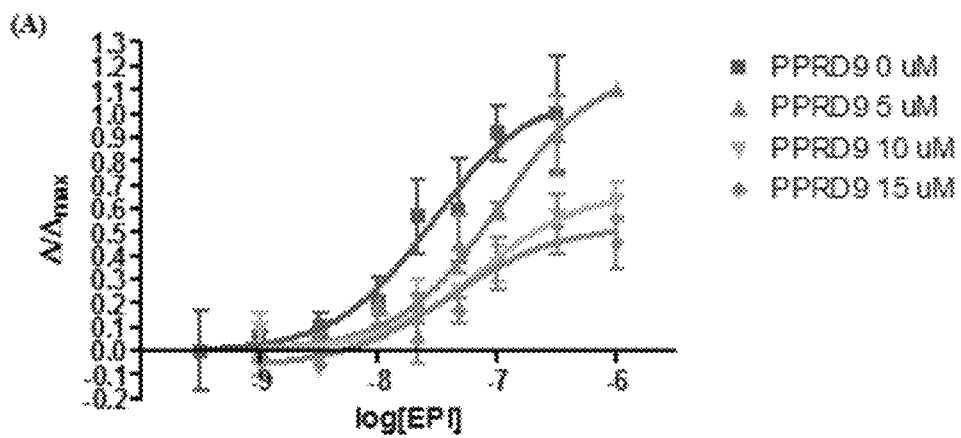
FIG. 16 graphically illustrates α4β2-nAChR antagonist dose-response curves of the exemplary PPRD series of compounds as provided herein including the exemplary (FIG. 16A) PPRD9, a mix-competitive antagonist, and (FIG. 16B) PPRD11, a competitive antagonist, as further described in Example 1, below.
Figure 16B:
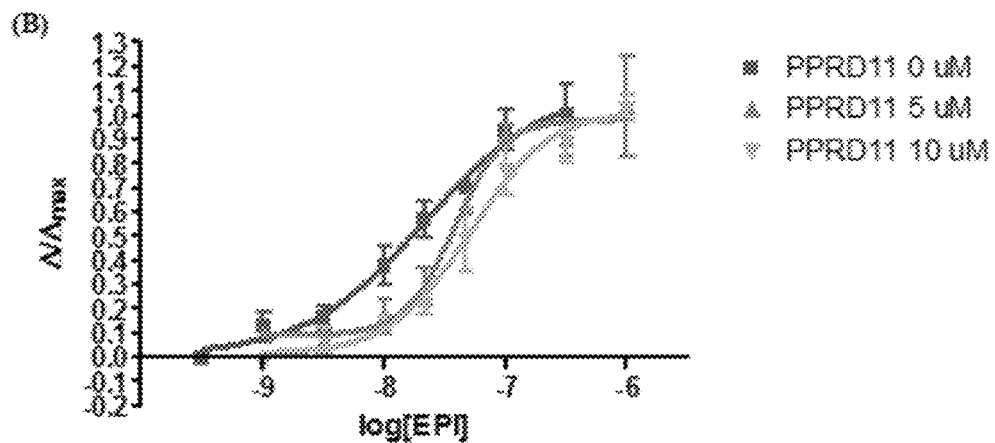

The functional properties of seven compounds that contain bicyclic amines are in agreement with the data from binding affinity analysis. Removal of H-bond donor by methylation of the —NH indole markedly reduced the agonist $EC_{50}$ of PPRD9 to 12.9 μM. PPRD9 also acts as α4β2-nAChR and $5HT_{3A}$ receptor antagonists (FIG. 16A, FIG. 16B and FIG. 11, respectively). Change in position of the H-bond donor by reversing the indole turned PPRD11 and PPRD12 into weak and non-selective α7-nAChR antagonists (FIG. 12). Moreover, PPRD11 also showed antagonist properties with α4β2-nAChR, whereas PPRD12 is $5HT_{3A}$ an antagonist (FIG. 16A, FIG. 16B and FIG. 11, respectively). For other ring systems, namely, benzodioxole and naphthalene in PPRD1 and PPRD6, the α7-nAChR agonist potency of PPRD1 was found to be low, whereas both agonist and antagonist potencies of PPRD6 were markedly reduced. The α7-nAChR dose-response curves are shown in FIG. 6A.

Figure 6B:
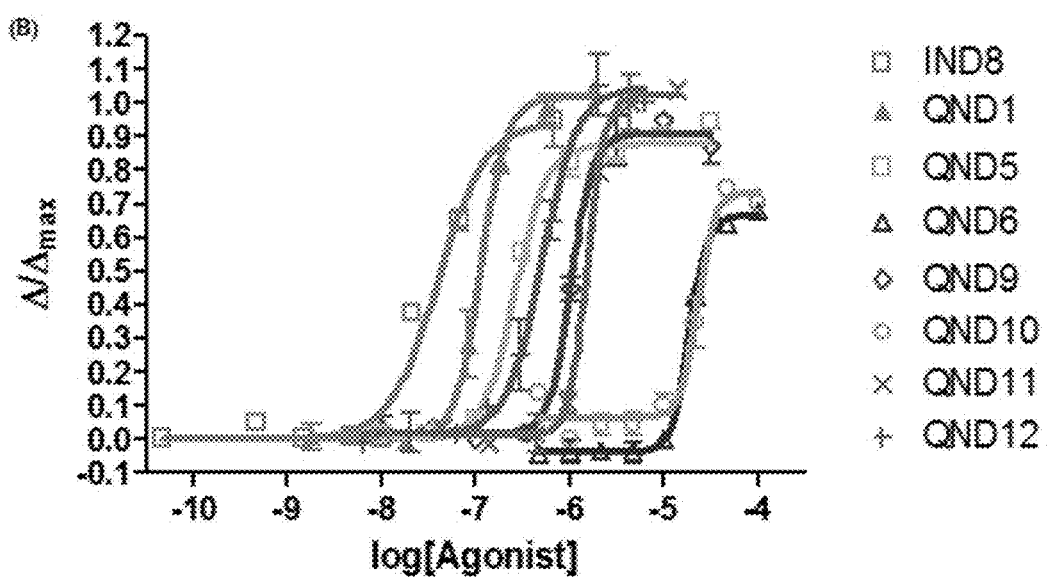

FIG. 6 shows α7-nAChR agonist dose-response curves of indole modification, other bicyclic rings, and nitrogen-rich ring for (A) PPRD and (B) QND series. The assays were performed in the presence of 10 μM PNU-120596. FRET ratios were normalized to the maximum response by 100 nM (±)-epibatidine.

The α7 agonist properties of compounds in QND series showed a common pattern with the PPRD series. The indole modification (QND5, 9, 11, 12) and other ring systems (QND1, 6) enhance neither the potency nor selectivity profiles for α7-nAChRs, when compared with IND8. Instead, QND6, 9, and 11 are α4β2-nAChR antagonists (FIG. 13). Compounds having heteroatom at para-position (QND1, 5, 9) and QND12 exhibited $5HT_{3A}$ agonist properties (FIG. 14) as discussed above, whereas QND11 is a $5HT_{3A}$ antagonist (Supplemental FIG. S8).

The replacement of indole with an electron-rich adenine ring altered PPRD10 to be α7-nAChR antagonist with moderate potency ($K_A=11.56^C$, $18.86^{NC}$ μM) (FIG. 12), whereas QND10 showed modest α7-agonist potency ($EC_{50}=29.53$ μM).

Figure 7:
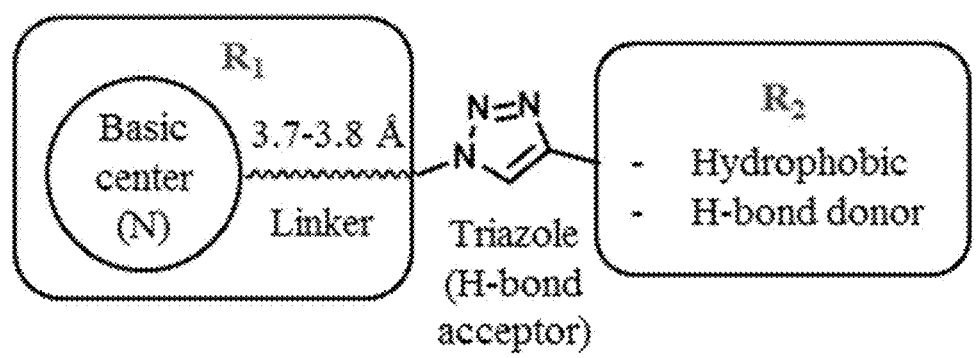
FIG. 7 illustrates the key pharmacophoric features of exemplary triazole derivatives needed to become selective α7-nAChR agonists, found by optimizing triazole derivatives via forty three compounds in three series provided herein (the exemplary IND, PPRD, and QND series); where the key features are: a basic center with 3.7-3.8 Å length of linker, a triazole ring as H-bond acceptor, and a hydrophobic group, optionally containing an H-bond donor, as further described in Example 1, below.

Among compounds in PPRD and QND series, all QND compounds have higher affinity and efficacy than the corresponding compounds in PPRD series. This might occur from the rigidity of quinuclidine ring which restricts the distance between the cationic center and the hydrogen bond acceptor in triazole to the optimal 3.7 Å distance, conferring key interactions in the binding pocket to achieve agonist properties. The hydrophobic $R_2$ is an important motif affecting to the selectivity and potency profile. The hydrophobic moiety that serves as a H-bond donor is the most suitable functional group for becoming potent α7-nAChR agonists. The information obtained from optimizing triazole derivatives via forty three compounds in three series provided herein (the exemplary IND, PPRD, and QND series) revealed that the basic center with 3.7-3.8 Å length of linker, the triazole ring as H-bond acceptor, and the hydrophobic group especially containing H-bond donor are the key pharmacophoric features of the triazole derivatives becoming selective α7-nAChR agonists, as illustrated in FIG. 7.

Conclusions

The α7-nAChR agonist properties of the compounds in the three series establishes that the triazole ring not only plays a role as the H-bond acceptor but, as a linker, provides an optimal distance and orientation for key interactions, cation-π, hydrogen bond and hydrophobic interactions in the binding pocket of α7-nAChR for α7-agonist action. A two carbon atom length of 3.7-3.8 Å between basic amine and triazole ring is the optimal distance to achieve agonists responses. Ring size and steric constraints of both basic center and hydrophobic motif also impact the selectivity and efficacy profile. IND1, which has piperidine as the basic amine with a 2 methylene linker to triazole, is a selective and potent α7-nAChR agonist in the series. The agonist potency is 3.5-fold higher than the lead compound and is highly selective for α7 over α4β2-nAChRs and the $5HT_{3A}$ receptors. IND8 with quinuclidine as the basic center is the most potent α7 agonist with a moderate selectivity profile, its α7 agonistic potency increases 20-fold from TTIn-1. When hydrophobic indole of IND1 and IND8 was modified in PPRD and QND series, no further improvement in affinity and efficacy profiles were found. Alteration of hydrophobic indole reduced the selectivity profile with antagonism on α4β2-nAChRs and $5HT_{3A}$ receptors. QND2 and QND8 are only 2 compounds having H-bond donor at the para-position of a simple aromatic ring that can maintain the 20-fold increase in α7-nAChR agonistic potency with a moderate selectivity profile.

Methods

1. General Experimental Detail

Chemical reagents are from Sigma-Aldrich, Oakwood, Alfa Aesar, Fluka, and Acros, whereas all solvents are from Fisher. All starting materials with at least 95% purity were used without further purification. The reactions were monitored by TLC and LC-MS (HP 1100 Series LC/MSD). The melting points of the final compounds were measured (Thomas Hoover Uni-melt) and the structures were elucidated by using FTIR (Thermo Scientific Nicolet iS5), NMR (Variance Mercury-300, Bruker AMX-400, Bruker DRX-500) and HRMS (Agilent ESI-TOF). The purity of final compounds was determined by chromatograms integration of the diode array UV acquired on an HP 1100 Series LC/MSD combining liquid chromatography with electron spray ionization (ESI) mass spectrometry. Analyses were conducted using a 30-100% MeCN/water containing 0.1% trifluoroacetic acid (TFA); all compounds were determined to be >95% purity. The physiochemical properties were predicted by MarvinSketch.

1.1 Azide Preparation

When starting with amines, the azide building blocks were prepared by method A, whereas method B and C were used for the molecules bearing good leaving groups. All azido compounds were confirmed by LC-MS and used in CuAAC without further purification (more than 90% purity).

Method A: Diazo Transfer Reaction[32] (IND1, 2, 3, 5, 6, 7, 8, 9, 10, 14, PPRD1-15, QND1-15)

The trifluoromethanesulfonyl azide ($TfN_3$) was prepared first by the reaction between trifluoromethanesulfonic anhydride and 5 equivalents of sodium azide in the mixture of water and toluene. The reaction mixture was stirred vigorously at room temperature for 2 h, and extracted with toluene to obtain $TfN_3$. Then the primary amine was reacted with 1.8 equivalents of freshly prepared $TfN_3$ in the mixture of $H_2O:CH_3OH$:toluene in the ratio of 3:6:5 at room temperature overnight to give the azido compound.

The methylene linker of some azide building blocks (IND3, 5, 14) was extended before azidation. Starting amine 1.3 equivalents was reacted with N-(2-bromoethyl)phthalimide, N-(3-bromopropyl)phthalimide, or N-(4-bromobutyl) phthalimide to vary the length of linker[33] using 2 equivalents of triethylamine ($Et_3N$) as catalyst. The reaction was refluxed overnight in EtOH. Then, the phthalimide group was de-protected by refluxing with hydrazine monohydrate for 45 min to give the primary amine.

Method B: Nucleophilic Substitution of Hydroxyl Group Containing Molecules[34] (IND4, 11)

The starting alcohol was mesylated first by 1.5 equivalents of methanesulfonyl chloride (MsCl) using 1.6 equivalents of $Et_3N$ as a basic catalyst. The reaction mixture was run in $CH_2Cl_2$ from 0° C. to room temperature for 4 h to get mesylated alcohol. After that, this mesylated alcohol was refluxed with 1.2 equivalents of sodium azide in MeCN for 6 h to obtain the azido compound.

Method C: Nucleophilic Substitution of Chloride Containing Molecules[35] (IND12, 13)

The starting material containing chloride as leaving group was refluxed overnight with 3 equivalents of sodium azide in water. After that, diethyl ether was added in the reaction mixture followed by 4 equivalents of NaOH. The reaction mixture was stirred in an iced bath for 30 min. Then, the reaction mixture was extracted with diethyl ether, dried over $MgSO_4$ anhydrous and concentrated in vacuo to obtain the azido compound.

1.2 Alkyne Preparation

The halogen containing molecule was reacted with 3 equivalents of ethynyltrimethylsilane having $PdCl_2(PPh_3)_2$ (0.03-0.05 equivalent), CuI (0.03-0.05 equivalent) as catalyst and $Et_3N$ as base in DMF at room temperature under $N_2$ atmosphere for 3 h to overnight via the Sonogashira reaction. After extraction with diethyl ether or EtOAc and purified by column chromatography, 1 M of TBAF in THF or $K_2CO_3$ in $CH_3OH$ was added to desilylation. The crude product was purified by column chromatography to give terminal alkyne products.

5-Ethynyl-1H-indole: The alkyne was prepared via method described above using 5-Iodoindole as starting reagent and purified by column chromatography (10% EtOAc in hexane) to yield intermediate compound (90.39%). $^1$H-NMR (300 MHz, $CDCl_3$) δ 8.19 (s, 1H), 7.82 (s, 1H), 7.35-7.27 (m, 2H), 7.22-7.17 (m, 1H), 6.55-6.50 (m, 1H), 0.28 (s, 9H); $^{13}$C-NMR (76 MHz, CDCl$_3$) δ 135.6, 127.7, 126.1, 125.3, 125.2, 114.3, 111.1, 107.1, 103.0, 91.3, 0.3. After desilylation and purification (10% EtOAc in hexane), 5-ethynyl-1H-indole as yellow solid was obtained (79.19%). $^{1}$H-NMR (500 MHz, CDCl$_3$) δ 8.20 (s, 1H), 7.85 (s, 1H), 7.38-7.29 (m, 2H), 7.24-7.19 (m, 1H), 6.55 (t, J=2.6 Hz, 1H), 3.02 (s, 1H); $^{13}$C-NMR (126 MHz, CDCl$_3$) δ 135.8, 127.8, 126.1, 125.5, 125.3, 113.3, 111.2, 103.0, 85.4, 74.8.

5-Ethynylbenzo[d][1,3]dioxole: The method as describe above was used to synthesize terminal alkynes. The yellow liquid intermediate was obtained after purification by column chromatography (hexane) (96.46%). $^{1}$H-NMR (500 MHz, CDCl$_3$) δ 7.00 (dd, J=8.0, 1.6 Hz, 1H), 6.91 (d, J=1.6 Hz, 1H), 6.74-6.71 (m, 1H), 5.95 (d, J=2.0 Hz, 2H), 0.25 (s, 9H); $^{13}$C-NMR (126 MHz, CDCl$_3$) δ 148.1, 147.4, 126.8, 116.5, 112.0, 108.4, 105.1, 101.4, 92.4, 0.1. After desilylation with K$_2$CO$_3$ in CH$_3$OH and purification by column chromatography (hexane), a light yellow liquid was obtained (88.46%). $^{1}$H-NMR (500 MHz, CDCl$_3$) δ 7.02 (dd, J=8.0, 1.6 Hz, 1H), 6.93 (d, J=1.6 Hz, 1H), 6.75 (d, J=8.0 Hz, 1H), 5.96 (s, 2H), 2.98 (s, 1H); $^{13}$C-NMR (126 MHz, CDCl$_3$) δ 148.4, 147.5, 127.0, 115.4, 112.1, 108.5, 101.4, 83.7, 75.7.

5-Ethynyl-1H-indole-3-carbaldehyde: The starting reagent, 5-iodoindole-3-carboxaldehyde was prepared. Dimethylformamide (0.3602 g, 4.93 mmol) was reacted with phosphorus oxychloride (0.1908 g, 1.24 mmol) at 0° C. for 30 min to produce an electrophilic iminium cation. After that 5-iodoindole (0.2978 g, 1.23 mmol) in DMF was added dropwise and stirred in an ice bath for 3 h. The reaction mixture was poured into ice-water, neutralized with 1N NaOH, and left it overnight. Then, it was extracted with CH$_2$Cl$_2$, dried with MgSO$_4$ anhydrous, and concentrated in vacuo before purification (50% EtOAc in hexane) to obtain orange solid (48.27%). After that the terminal alkyne product was prepared with the method described above and purified by column chromatography (20% EtOAc in hexane to EtOAc) to yield brown solid compound (38.21% over all steps). $^{1}$H-NMR (400 MHz, CD$_3$OD) δ 9.89 (s, 1H), 8.29 (s, 1H), 8.14 (s, 1H), 7.44 (d, J=8.4 Hz, 1H), 7.36 (d, J=8.5 Hz, 1H), 3.38 (s, 1H).

4-Ethynylphenol: The intermediate was synthesized by the method described above and purified by column chromatography (0-20% EtOAc in hexane) to obtain brown liquid. $^{1}$H-NMR (500 MHz, CDCl$_3$) δ 7.35 (d, J=8.3 Hz, 2H), 6.75 (d, J=8.3 Hz, 2H), 6.05 (s, 1H), 0.25 (s, 9H); $^{13}$C-NMR (126 MHz, CDCl$_3$) δ 156.0, 133.8, 115.5, 115.4, 105.5, 92.7, 0.17. After desilylation, the crude product was purified by column chromatography (0-20% EtOAc in hexane) to obtain a purple liquid (60.08% over all steps). $^{1}$H-NMR (400 MHz, CD$_3$OD) δ 7.30-7.25 (m, 2H), 6.75-6.70 (m, 2H), 3.25 (s, 1H); $^{13}$C-NMR (101 MHz, CD$_3$OD) δ 159.3, 134.5, 116.4, 114.5, 84.8, 76.3.

5-Ethynyl-1-methyl-1H-indole: To a solution of anhydrous K$_2$CO$_3$ (0.3110 g, 2.25 mmol), 5-iodoindole (0.5800 g, 2.39 mmol) and anhydrous DMF (4 mL) was added dimethyl carbonate (0.62 mL, 7.38 mmol). The reaction mixture was heated to 130° C. for 3.5 h. The reaction mixture was cooled on an ice bath followed by addition of cold water and extracted with diethyl ether. The crude material was purified by column chromatography (CH$_2$Cl$_2$). The product was isolated as a 1 to 1 mixture of the starting material (5-iodoindole) and 5-iodo-methylindole. The reaction mixture was then synthesized by method described above and purified by column chromatography (0-5% EtOAc in hexane) to give the intermediate product as a brown oil (24.84% over two steps). $^{1}$H-NMR (300 MHz, CD$_2$Cl$_2$) δ 7.73 (d, J=1.0 Hz, 1H), 7.28 (d, J=1.3 Hz, 2H), 7.11 (d, J=3.1 Hz, 1H), 6.45 (d, J=3.1 Hz, 1H), 3.78 (s, 3H), 0.25 (s, 9H). After desilylation and purified by column chromatography (0-10% EtOAc in hexane), the terminal alkyne as a light brown liquid was obtained (76.39%). TH-NMR (300 MHz, CD$_2$Cl$_2$) δ 7.80 (s, 1H), 7.34 (dd, J=8.5, 1.4 Hz, 1H), 7.28 (d, J=8.5 Hz, 1H), 7.11 (d, J=3.1 Hz, 1H), 6.48 (d, J=2.8 Hz, 1H), 3.76 (s, 3H), 3.06 (s, 1H); $^{13}$C-NMR (76 MHz, CD$_2$Cl$_2$) δ 137.1, 130.7, 128.8, 125.7, 125.7, 112.9, 109.9, 101.6, 85.8, 75.1, 33.3, 30.3.

9-(Prop-2-ynyl)-9H-purin-6-amine: A suspension of adenine (0.2050 g, 1.51 mmol) in anhydrous DMF (6 mL) was added K$_2$CO$_3$ (0.2140 g, 1.55 mmol) and propargyl bromide (0.4 mL, 3.64 mmol). The mixture was stirred at room temperature for overnight and concentrated under reduced pressure. The crude product was purified by column chromatography (0-10% CH$_3$OH in CH$_2$Cl$_2$). The product was isolated as a white solid (25.12%). $^{1}$H-NMR (300 MHz, DMSO-d$_6$) δ 8.19 (s, 1H), 8.16 (s, 1H), 7.28 (s, 2H), 5.02 (d, J=2.5 Hz, 2H), 3.47 (t, J=2.5 Hz, 1H).

Methyl 3-ethynyl-1H-indole-5-carboxylate: Indole-5-carboxylic acid (0.4834 g, 3.00 mmol) was iodinated with iodine (0.7710 g, 3.04 mmol) and KOH (0.4772 g, 8.50 mmol) in DMF at room temperature for 3 h. The reaction mixture was poured into 1 equivalent of sodium bisulfite in iced water, adjusted pH with 2N HCl to 3, and filtered via buchner funnel to obtain beige solid compound (82.42%). $^{1}$H-NMR (400 MHz, CD$_3$OD) δ 8.10 (dd, J=1.6, 0.6 Hz, 1H), 7.89-7.84 (m, 1H), 7.46 (s, 1H), 7.43 (dd, J=8.6, 0.7 Hz, 1H). Then, 3-Iodo-1H-indole-5-carboxylic acid (0.3009 g, 1.05 mmol) was esterified by reacting with methyl iodide (0.6840 g, 4.82 mmol) and NaHCO$_3$ (0.2835 g, 3.37 mmol) in DMF under N$_2$ atmosphere. The reaction was run at room temperature for 3 days. The water was added and extracted with EtOAc. The organic solvent was evaporated to yield orange to brown solid (100.06%).$^{1}$H-NMR (500 MHz, DMSO-d$_6$) δ 7.98-7.95 (m, 1H), 7.79 (dd, J=8.6, 1.6 Hz, 1H), 7.70 (d, J=2.4 Hz, 1H), 7.51 (d, J=8.5 Hz, 1H), 3.87 (s, 3H); $^{13}$C-NMR (126 MHz, DMSO-d$_6$) δ 166.9, 138.7, 131.7, 129.1, 123.0, 122.3, 121.4, 112.1, 57.6, 51.8. Then intermediate compound was prepared by method as described above and purified by column chromatography (0-20% EtOAc in hexane) to obtain terminal alkyne as a light brown solid (83.4%) and desilylation with 1 M of TBAF in THF. The crude product was purified by column chromatography (0-50% EtOAc in hexane) to obtain yellow to orange solid (86.40% over all steps). $^{1}$H-NMR (400 MHz, CD$_3$OD) δ 8.34 (dd, J=1.6, 0.7 Hz, 1H), 7.86 (dd, J=8.6, 1.6 Hz, 1H), 7.58 (s, 1H), 7.45 (dd, J=8.6, 0.7 Hz, 1H), 3.92 (s, 3H), 3.54 (s, 1H); $^{13}$C-NMR (101 MHz, CD$_3$OD) δ 169.7, 139.6, 132.1, 129.7, 124.7, 123.1, 123.1, 112.6, 99.5, 80.3, 77.7, 52.4.

3-Ethynyl-1H-indole: Indole (0.4681 g, 4.00 mmol) was iodinated by reacting with iodine (1.0183 g, 4.01 mmol) and KOH (0.5666 g, 10.10 mmol) in DMF at room temperature for 3 h. The reaction was stopped by pouring the reaction mixture into 1 equivalent of sodium metabisulfite in iced water and adjusted the pH to 3 by 2N HCl. Then, it was filtered via buchner funnel, washed with water and dried to get yellow to brown solid (91.12%). $^{1}$H-NMR (400 MHz, DMSO-d$_6$) δ 7.54 (d, J=2.5 Hz, 1H), 7.43-7.38 (m, 1H), 7.27 (ddt, J=7.8, 1.5, 0.7 Hz, 1H), 7.19-7.14 (m, 1H), 7.13-7.07 (m, 1H); $^{13}$C-NMR (126 MHz, CDCl$_3$) δ 135.7, 129.9, 128.5, 123.3, 121.1, 121.0, 111.4, 57.7. Then, the nitrogen atom in indole was protected with BOC protecting group by reacting with BOC anhydride (0.8750 g, 4.01 mmol), Et$_3$N (1.1050 g, 10.92 mmol), and DMAP (0.0452 g, 0.37 mmol) in $CH_2Cl_2$ at room temperature for 1 h. The reaction mixture was extracted with 5% sodium metabisulfite and dried over $MgSO_4$ anhydrous before purification by column chromatography (5% EtOAc in hexane) to obtain yellow solid (92.11%). The Sonogashira reaction as described above was performed and purified by column chromatography (5% EtOAc in hexane) to obtain brown liquid (96.77%). $^1$H-NMR (500 MHz, $CDCl_3$) δ 8.13 (d, J=8.0 Hz, 1H), 7.78 (s, 1H), 7.67 (d, J=7.7 Hz, 1H), 7.35 (t, J=7.5 Hz, 1H), 7.30 (t, J=7.2 Hz, 1H), 1.66 (s, 9H), 0.29 (s, 9H); $^{13}$C-NMR (126 MHz, DMSO-$d_6$) δ 149.2, 134.7, 130.7, 129.6, 125.3, 123.3, 120.3, 115.3, 103.6, 98.3, 96.9, 84.4, 28.3, 0.2. The BOC was deprotected by adding MeCN and water in 1 to 1 ratio into the intermediate compound (0.2419 g, 0.77 mmol) and activated with microwave generator at 100° C. for 1 h. Then, it was extracted with $CH_2Cl_2$ and purified by column chromatography (10% EtOAc in hexane) to obtain yellow liquid (72.86%). Then, it was desilylated by $K_2CO_3$ (0.1526 g, 1.10 mmol) in $CH_3OH$ for 2 h. The solvent was evaporated and the crude product was added $CH_2Cl_2$ and water. The pH was adjusted to 3 by 2N HCl and extracted with $CH_2Cl_2$ before purification by column chromatography (10% EtOAc in hexane to EtOAc) to give a pale yellow solid compound (41.70%). $^1$H-NMR (500 MHz, $CD_3OD$) δ 7.59 (d, J=8.0 Hz, 1H), 7.46 (s, 1H), 7.38 (d, J=8.1 Hz, 1H), 7.18-7.13 (m, 1H), 7.12-7.07 (m, 1H), 3.42 (s, 1H).

Methyl 5-ethynyl-2-hydroxybenzoate: 2-Hydroxy-5-iodobenzoic acid (0.5476 g, 2.07 mmol) was refluxed overnight in $CH_3OH$ with 0.5 mL of conc. $H_2SO_4$ to esterify the carboxylic group. The solvent was evaporated. Then, EtOAc was added, and it was extracted with saturated $NaHCO_3$, water, and brine solution. After that it was purified with column chromatography (5% EtOAc in hexane) to yield white solid (89.91%). $^1$H-NMR (500 MHz, $CDCl_3$) δ 10.73-10.70 (m, 1H), 8.14-8.12 (m, 1H), 7.71-7.67 (m, 1H), 6.79-6.75 (m, 1H), 3.95 (s, 3H); $^{13}$C-NMR (126 MHz, $CDCl_3$) δ 169.5, 161.4, 144.2, 138.4, 120.1, 114.7, 80.2, 52.7. The Sonogashira reaction was performed and product purified by column chromatography (10% EtOAc in hexane) to obtain a light brown solid (99.26%). $^1$H-NMR (500 MHz, $CDCl_3$) δ 10.89 (s, 1H), 7.98 (d, J=2.1 Hz, 1H), 7.53 (dd, J=8.6, 2.2 Hz, 1H), 6.91 (d, J=8.6 Hz, 1H), 3.95 (s, 3H), 0.26-0.22 (m, 9H); $^{13}$C-NMR (126 MHz, $CDCl_3$) δ 170.1, 161.7, 139.1, 134.0, 118.0, 114.4, 112.5, 104.1, 93.1, 52.6, 0.1. Then, it was desilylated before purification by column chromatography (5% EtOAc in hexane) to obtain a pale yellow solid (74.46%). $^1$H-NMR (500 MHz, $CDCl_3$) δ 10.92-10.89 (m, 1H), 8.00 (d, J=2.1 Hz, 1H), 7.55 (dd, J=8.6, 2.1 Hz, 1H), 6.96-6.92 (m, 1H), 3.96 (s, 3H), 2.99 (s, 1H); $^{13}$C-NMR (126 MHz, $CDCl_3$) δ 198.2, 171.2, 166.4, 136.6, 132.6, 130.2, 118.9, 113.5, 53.3, 26.3.

Methyl 2-amino-5-ethynylbenzoate: 2-Amino-5-iodobenzoic acid (0.6616 g, 2.52 mmol) was refluxed overnight in $CH_3OH$ with TMSCl (1.3689 g, 12.60 mmol) to esterify the carboxylic group. The solvent was evaporated. After that EtOAc was added, and it was extracted with saturated $NaHCO_3$, water, and brine solution. After that it was purified with column chromatography (5% EtOAc in hexane) to yield yellow solid (39.29%). $^1$H-NMR (500 MHz, $CDCl_3$) δ 8.14 (d, J=2.2 Hz, 1H), 7.47 (dd, J=8.7, 2.2 Hz, 1H), 6.46 (d, J=8.7 Hz, 1H), 3.86 (s, 3H); $^{13}$C-NMR (126 MHz, $CDCl_3$) δ 167.5, 149.9, 142.4, 139.6, 119.0, 113.0, 76.1, 51.9. The terminal alkyne was prepared by method described above and purified by column chromatography (5% EtOAc in hexane) to obtain yellow solid (84.78%). $^1$H-NMR (500 MHz, $CD_3OD$) δ 7.86 (d, J=2.0 Hz, 1H), 7.25 (dd, J=8.6, 2.1 Hz, 1H), 6.68 (d, J=8.6 Hz, 1H), 3.85 (s, 3H), 0.21-0.19 (m, 9H); $^{13}$C-NMR (126 MHz, $CDCl_3$) δ 168.1, 150.5, 137.4, 135.7, 116.7, 110.8, 110.5, 105.2, 91.6, 51.8, 0.2. Then, it was desilylated before purification by column chromatography (10% EtOAc in hexane) to obtain pale yellow solid (50.72%). $^1$H-NMR (500 MHz, $CD_3OD$) δ 7.89 (d, J=2.0 Hz, 1H), 7.28 (dd, J=8.6, 2.1 Hz, 1H), 6.72-6.66 (m, 1H), 3.84 (s, 3H), 3.22 (s, 1H); $^{13}$C-NMR (126 MHz, $CDCl_3$) δ 169.1, 152.9, 138.0, 136.2, 117.7, 110.6, 110.0, 84.5, 75.8, 52.0.

1.3 Copper Catalyzed Azide-Alkyne Cycloaddition (CuAAC)

The azide building blocks from method A, B or C was reacted with an alkyne building block (1:1) in a mixture of t-BuOH and water (1:1) using 5 mol % of $CuSO_4.5H_2O$ and 20 mol % of sodium ascorbate as catalyst. The reaction mixture was run at room temperature for 2.5-24 h and purified by column chromatography.

5-(1-(2-(Piperidin-1-yl)ethyl)-1H-1,2,3-triazol-4-yl)-1H-indole (IND1): 1-(2-Azidoethyl)piperidine (0.0641 g, 0.42 mmol) from method A was reacted with 5-ethynyl-1H-indole (0.0499 g, 0.35 mmol) in a 1 to 1 ratio of t-BuOH and water with $CuSO_4.5H_2O$ (0.0050 g, 0.02 mmol) and sodium ascorbate (0.0158 g, 0.08 mmol) as catalyst. The reaction was stirred at room temperature for 5 h. After that, the reaction mixture was extracted with $CH_2Cl_2$. The crude product was purified by column chromatography (EtOAc) to give a pale yellow solid compound (68.86%). FTIR (ATR) ($cm^{-1}$) 3318, 3148, 3083, 2924, 1480, 1469, 1452, 1438, 1346, 1225, 1121, 1054, 892, 795, 771, 745; $^1$H-NMR (500 MHz, DMSO-$d_6$) δ 8.41 (s, 1H), 8.00 (dd, J=1.6, 0.8 Hz, 1H), 7.58 (dd, J=8.4, 1.5 Hz, 1H), 7.44 (d, J=8.4 Hz, 1H), 7.36 (dd, J=2.9, 2.2 Hz, 1H), 6.50-6.44 (m, 1H), 4.48 (t, J=6.5 Hz, 2H), 2.76 (t, J=6.5 Hz, 2H), 2.47-2.34 (m, 4H), 1.48 (dt, J=10.8, 5.6 Hz, 4H), 1.42-1.33 (m, 2H); $^{13}$C-NMR (126 MHz, DMSO-$d_6$) δ 147.7, 135.6, 127.8, 126.0, 122.0, 120.3, 119.0, 116.7, 111.7, 101.4, 57.8, 53.8, 47.0, 25.5, 23.9; mp=148-149° C.; HRMS calculated ($C_{17}H_{21}N_5$, $MH^+$) 296.1871, found 296.1871.

5-(1-(3-(Piperidin-1-yl)propyl)-1H-1,2,3-triazol-4-yl)-1H-indole (IND2): The same method as IND1 was used. 1-(3-Azidopropyl)piperidine (0.0588 g, 0.35 mmol) from method A was reacted with 5-ethynyl-1H-indole (0.0506 g, 0.36 mmol). The crude product was purified by column chromatography (5% $Et_3N$ in EtOAc) to give a white solid compound (42.17%). FTIR (ATR) ($cm^{-1}$) 3331, 3130, 3099, 3080, 3034, 2923, 1614, 1556, 1433, 1358, 1345, 1211, 1114, 1070, 889, 804, 736; $^1$H-NMR (500 MHz, $CD_3OD$) δ 8.21 (s, 1H), 8.01 (dd, J=1.3, 0.4 Hz, 1H), 7.56 (dd, J=8.5, 1.5 Hz, 1H), 7.44 (d, J=8.5 Hz, 1H), 7.26 (d, J=3.1 Hz, 1H), 6.49 (d, J=3.1 Hz, 1H), 4.46 (t, J=6.9 Hz, 2H), 2.43 (br s, 4H), 2.38 (t, J=7.6 Hz, 2H), 2.15 (p, J=7.3 Hz, 2H), 1.60 (p, J=5.6 Hz, 4H), 1.46 (p, J=5.8 Hz, 2H); $^{13}$C-NMR (126 MHz, $CD_3OD$) 150.6, 137.7, 129.8, 126.6, 122.6, 121.3, 120.5, 118.6, 112.6, 102.8, 56.9, 55.5, 49.7, 28.2, 26.6, 25.2; mp=93-95° C.; HRMS calculated ($C_{18}H_{23}N_5$, $MH^+$) 310.2026, found 310.2037.

5-(1-(4-(Piperidin-1-yl)butyl)-1H-1,2,3-triazol-4-yl)-1H-indole (IND3): The same method as IND1 was used. 1-(4-Azidobutyl)piperidine (0.0647 g, 0.35 mmol) from method A was reacted with 5-ethynyl-1H-indole (0.0492 g, 0.35 mmol) for overnight. The crude compound was purified by column chromatography (8% $Et_3N$ in EtOAc) to obtain a white solid product (41.87%). FTIR (ATR) ($cm^{-1}$) 3320, 3114, 3080, 3026, 2933, 2916, 1559, 1469, 1436, 1417, 1352, 1307, 1110, 1064, 1045, 890, 859, 797, 778, 731; $^1$H-NMR (500 MHz, $CD_3OD$) δ 8.21 (s, 1H), 8.01 (dd, J=1.4, 0.6 Hz, 1H), 7.56 (dd, J=8.4, 1.4 Hz, 1H), 7.44 (d, J=8.5 Hz, 1H), 7.26 (d, J=3.1 Hz, 1H), 6.49 (d, J=3.0 Hz, 1H), 4.45 (t, J=7.0 Hz, 2H), 2.50-2.31 (m, 6H), 1.96 (p, J=7.3 Hz, 2H), 1.62-1.52 (m, 6H), 1.49-1.41 (m, 2H); $^{13}$C-NMR (126 MHz, CD$_3$OD) δ 150.7, 137.7, 129.8, 126.6, 122.6, 121.2, 120.5, 118.6, 112.6, 102.8, 59.6, 55.4, 51.2, 29.4, 26.4, 25.2, 24.3; mp=103-105° C.; HRMS calculated (C$_{19}$H$_{25}$N$_5$, MH$^+$) 324.2183, found 324.2187.

5-(1-(2-(Morpholin-4-yl)ethyl)-1H-1,2,3-triazol-4-yl)-1H-indole (IND4): The same method as IND1 was used. 4-(2-Azidoethyl)morpholine (0.0622 g, 0.40 mmol) from method B was reacted with 5-ethynyl-1H-indole (0.0457 g, 0.32 mmol) for 2.5 h. The crude compound was purified by column chromatography (EtOAc) to obtain a pale orange solid compound (57.86%). FTIR (ATR) (cm$^{-1}$) 3296, 3088, 2971, 2929, 2863, 2813, 1558, 1506, 1459, 1432, 1315, 1301, 1251, 1221, 1148, 1108, 1066, 1006, 861, 811, 764, 732; $^1$H-NMR (500 MHz, CD$_3$OD) δ 8.24 (s, 1H), 8.02-7.99 (m, 1H), 7.56 (dd, J=8.5, 1.5 Hz, 1H), 7.44 (d, J=8.4 Hz, 1H), 7.27 (d, J=3.1 Hz, 1H), 6.50 (d, J=3.1 Hz, 1H), 4.57 (t, J=6.3 Hz, 2H), 3.67 (t, J=4.6 Hz, 4H), 2.90 (t, J=6.4 Hz, 2H), 2.54 (t, J=4.3 Hz, 4H); $^{13}$C-NMR (126 MHz, CD$_3$OD) δ 150.5, 137.7, 129.8, 126.6, 122.7, 121.7, 120.6, 118.6, 112.6, 102.8, 67.9, 58.9, 54.6, 48.5; mp=170-172° C.; HRMS calculated (C$_{16}$H$_{29}$N$_5$O, MH$^+$) 298.1662, found 298.1663.

5-(1-(3-(Morpholin-4-yl)propyl)-1H-1,2,3-triazol-4-yl)-1H-indole (IND5): The same method as IND1 was used. 4-(3-Azidopropyl)morpholine (0.0519 g, 0.30 mmol) from method A was reacted with 5-ethynyl-1H-indole (0.0490 g, 0.35 mmol) for overnight using the same method as IND1. The crude compound was purified by column chromatography (10% CH$_3$OH in EtOAc) to obtain a pale brown solid compound (49.40%). FTIR (ATR) (cm$^{-1}$) 3264, 3121, 3097, 2964, 2908, 2858, 2806, 1558, 1457, 1441, 1425, 1319, 1288, 1273, 1212, 1108, 1071, 1020, 889, 853, 809, 766, 725; $^1$H-NMR (500 MHz, DMSO-d$_6$) δ 8.45 (s, 1H), 8.02-7.99 (m, 1H), 7.58 (dd, J=8.4, 1.6 Hz, 1H), 7.44 (d, J=8.4 Hz, 1H), 7.36 (t, J=2.7 Hz, 1H), 6.49-6.44 (m, 1H), 4.41 (t, J=7.1 Hz, 2H), 3.57 (t, J=4.6 Hz, 4H), 2.34 (br s, 4H), 2.30 (t, J=6.9 Hz, 2H), 2.04 (p, J=6.9 Hz, 2H); $^{13}$C-NMR (101 MHz, DMSO-d$_6$) δ 147.8, 135.6, 127.9, 126.0, 121.9, 120.1, 119.0, 116.7, 111.7, 101.4, 66.2, 54.9, 53.2, 47.7, 26.7; mp=188-189° C.; HRMS calculated (C$_{17}$H$_{21}$N$_5$O, MH$^+$) 312.1819, found 312.1813.

5-(1-(4-(Morpholin-4-yl)butyl)-1H-1,2,3-triazol-4-yl)-1H-indole (IND6): The same method as IND1 was used. 4-(4-Azidobutyl)morpholine (0.0725 g, 0.39 mmol) from method A and 5-ethynyl-1H-indole (0.0487 g, 0.34 mmol) was reacted for 2.5 h. The reaction mixture was filtered and washed with water, CH$_2$Cl$_2$, and EtOAc to obtain a pale yellow solid compound (29.57%). FTIR (ATR) (cm$^{-1}$) 3279, 3099, 3073, 2961, 2890, 2858, 2824, 1559, 1471, 1435, 1415, 1351, 1306, 1256, 1116, 1069, 901, 872, 805, 779, 737; $^1$H-NMR (500 MHz, DMSO-d$_6$) δ 8.45 (s, 1H), 8.01 (s, 1H), 7.59 (dd, J=8.5, 1.2 Hz, 1H), 7.44 (d, J=8.4 Hz, 1H), 7.36 (t, J=2.6 Hz, 1H), 6.46 (t, J=2.2 Hz, 1H), 4.39 (t, J=7.0 Hz, 2H), 3.55 (t, J=4.3 Hz, 4H), 2.41-2.21 (m, 6H), 1.89 (p, J=7.6 Hz, 2H), 1.44 (p, J=7.3 Hz, 2H); $^{13}$C-NMR (126 MHz, DMSO-d$_6$) δ 147.9, 135.6, 127.8, 126.0, 121.9, 119.9, 119.0, 116.7, 111.7, 101.4, 66.1, 57.4, 53.2, 49.3, 27.6, 22.8; mp=157-158° C.; HRMS calculated (C$_{15}$H$_{23}$N$_5$O, MH$^+$) 326.1975, found 326.1985.

5-(1-((1R,5S)-9-Methyl-9-azabicyclo[3.3.1]nonan-3-yl)-1H-1,2,3-triazol-4-yl)-1H-indole (IND7): The same method as IND1 was used. 3-Azido-9-methyl-9-azabicyclo[3.3.1]nonane (0.0643 g, 0.36 mmol) from method A was reacted with 5-ethynyl-1H-indole (0.0453 g, 0.32 mmol) for overnight. Then, the reaction mixture was filtered and washed with water, CH$_2$Cl$_2$, and EtOAc to obtain a pale yellow solid compound (64.67%). FTIR (ATR) (cm$^{-1}$) 3190, 3158, 2935, 2903, 2891, 1555, 1436, 1372, 1343, 1217, 1142, 1127, 1114, 1071, 1025, 1012, 889, 766, 727, 710; $^1$H-NMR (500 MHz, CD$_3$OD) δ 8.31 (s, 1H), 8.02 (d, J=1.0 Hz, 1H), 7.58 (dd, J=8.4, 1.6 Hz, 1H), 7.44 (d, J=8.4 Hz, 1H), 7.26 (d, J=3.1 Hz, 1H), 6.49 (dd, J=3.1, 0.6 Hz, 1H), 5.48 (tt, J=12.6, 6.4 Hz, 1H), 3.09 (t, J=4.8 Hz, 2H), 2.63 (s, 3H), 2.62-2.55 (m, 2H), 2.20-2.07 (m, 4H), 2.02-1.89 (m, 1H), 1.78 (dd, J=14.5, 7.2 Hz, 1H), 1.72 (dd, J=14.4, 6.2 Hz, 2H); $^{13}$C-NMR (126 MHz, CD$_3$OD) δ 150.3, 137.7, 129.8, 126.6, 122.7, 120.6, 119.4, 118.6, 112.6, 102.8, 56.4, 54.6, 40.8, 33.4, 27.8, 20.7; mp=211-213° C.; HRMS calculated (C$_{19}$H$_{23}$N$_5$, MH$^+$) 322.2026, found 322.2026.

5-((Quinuclid-3-yl)-1H-1,2,3-triazol-4-yl)-1H-indole (IND8): The same method as IND1 was used. 3-Azidoquinuclidine (0.0442 g, 0.29 mmol) from method A was reacted with 5-ethynyl-1H-indole (0.0484 g, 0.34 mmol) for overnight. The crude product was purified by column chromatography (10% Et$_3$N and 10% CH$_3$OH in EtOAc) to give a white solid compound (28.05%). FTIR (ATR) (cm$^{-1}$) 3114, 3031, 2995, 2944, 2923, 2866, 1621, 1556, 1455, 1438, 1345, 1322, 1303, 1250, 1210, 1063, 1046, 982, 971, 907, 885, 791, 767, 737; $^1$H-NMR (500 MHz, DMSO-d$_6$) δ 8.60 (s, 1H), 8.05 (s, 1H), 7.63 (dd, J=8.5, 1.2 Hz, 1H), 7.44 (d, J=8.5 Hz, 1H), 7.36 (t, J=2.7 Hz, 1H), 6.47 (t, J=2.4 Hz, 1H), 4.77-4.71 (m, 1H), 3.48 (dd, J=14.1, 5.3 Hz, 1H), 3.42-3.36 (m, 1H), 3.04-2.96 (m, 1H), 2.82-2.73 (m, 3H), 2.22-2.17 (m, 1H), 1.79-1.67 (m, 2H), 1.51-1.34 (m, 2H); $^{13}$C-NMR (101 MHz, DMSO-d$_6$) δ 147.8, 135.6, 127.8, 126.0, 121.9, 119.6, 119.0, 116.8, 111.7, 101.3, 57.1, 51.8, 46.6, 46.4, 27.6, 25.2, 19.6; mp=238-240° C.; HRMS calculated (C$_{17}$H$_{19}$N$_5$, MH$^+$) 294.1713, found 294.1717.

5-(1-(2-(Piperazin-1-yl)ethyl)-1H-1,2,3-triazol-4-yl)-1H-indole (IND9): The same method as IND1 was used. 1-(2-Azidoethyl)piperazine (0.0717 g, 0.46 mmol) from method A was reacted with 5-ethynyl-1H-indole (0.0497 g, 0.35 mmol) for 2.5 h. The crude compound was purified by column chromatography (1% NH$_4$OH and 5% CH$_3$OH in CH$_2$Cl$_2$) to obtain a white solid product (20.89%). FTIR (ATR) (cm$^{-1}$) 3239, 3140, 3053, 3019, 2943, 2908, 2821, 1661, 1612, 1551, 1437, 1342, 1214, 1159, 1107, 872, 852, 798, 727; $^1$H-NMR (500 MHz, CD$_3$OD) δ 8.24 (s, 1H), 8.00 (dd, J=1.6, 0.6 Hz, 1H), 7.56 (dd, J=8.4, 1.6 Hz, 1H), 7.44 (dd, J=8.6, 0.84 Hz, 1H), 7.27 (d, J=3.1 Hz, 1H), 6.50 (dd, J=3.1, 0.8 Hz, 1H), 4.57 (t, J=6.4 Hz, 2H), 2.89 (t, J=6.4 Hz, 2H), 2.83 (t, J=4.9 Hz, 4H), 2.53 (br s, 4H); $^{13}$C-NMR (126 MHz, CD$_3$OD) δ 150.5, 137.7, 129.8, 126.6, 122.7, 121.7, 120.6, 118.6, 112.6, 102.8, 59.1, 54.7, 48.6, 46.3; mp=177-178° C.; HRMS calculated (C$_{16}$H$_{20}$N$_6$, MH$^+$) 297.1822, found 297.1826.

5-(1-(Piperidin-3-yl)-1H-1,2,3-triazol-4-yl)-1H-indole (IND10): The same method as IND1 was used. 3-Azidopiperidine (0.0458 g, 0.36 mmol) from method A and 5-ethynyl-1H-indole (0.0502 g, 0.36 mmol) was reacted for overnight and purified by column chromatography (10% CH$_3$OH in CH$_2$Cl$_2$) to obtain a white solid compound (23.39%). FTIR (ATR) (cm$^{-1}$) 3120, 3080, 3030, 2969, 2927, 2849, 1623, 1562, 1426, 1415, 1343, 1234, 1211, 1106, 1079, 1048, 883, 773, 735; $^1$H-NMR (500 MHz, CD$_3$OD) δ 8.29 (s, 1H), 8.01 (s, 1H), 7.57 (d, J=8.5 Hz, 1H), 7.44 (d, J=8.3 Hz, 1H), 7.27 (d, J=2.9 Hz, 1H), 6.49 (d, J=2.4 Hz, 1H), 4.58 (ddd, J=14.8, 10.8, 4.2 Hz, 1H), 3.37 (dd, J=12.8, 3.7 Hz, 1H), 3.09-2.99 (m, 2H), 2.73-2.63 (m, 1H), 2.33 (dd, J=12.3, 2.7 Hz, 1H), 2.11 (qd, J=12.1, 4.1 Hz, 1H), 1.94-1.85 (m, 1H), 1.77-1.65 (m, 1H); $^{13}$C-NMR (101 MHz, CD$_3$OD) δ 150.3, 137.7, 129.8, 126.6, 122.7, 120.6, 119.8, 118.7, 112.6, 102.8, 59.1, 52.1, 46.3, 32.2, 26.2; mp=166-168° C.; HRMS calculated (C$_{15}$H$_{17}$N$_5$, MH$^+$) 268.1557, found 268.1558.

5-(1-(1-Methylpiperidin-3-yl)-1H-1,2,3-triazol-4-yl)-1H-indole (IND11): The same method as IND1 was used. 3-Azido-1-methylpiperidine (0.0514 g, 0.37 mmol) from method B was reacted with 5-ethynyl-1H-indole (0.0482 g, 0.34 mmol) for 16 h and purified by column chromatography (5% CH$_3$OH in CH$_2$Cl$_2$) to obtain a white solid compound (58.92%). FTIR (ATR) (cm$^{-1}$) 3285, 3163, 3089, 2958, 2907, 2872, 2846, 2783, 1619, 1549, 1483, 1450, 1345, 1228, 1188, 1057, 891, 793, 767, 741; $^1$H-NMR (500 MHz, DMSO-d$_6$) δ 8.40 (s, 1H), 8.01 (d, J=0.7 Hz, 1H), 7.59 (dd, J=8.4, 1.6 Hz, 1H), 7.43 (d, J=8.5 Hz, 1H), 7.36 (t, J=2.7 Hz, 1H), 6.46 (d, J=2.2 Hz, 1H), 4.47 (dd, J=13.8, 4.4 Hz, 1H), 4.29 (dd, J=13.8, 6.4 Hz, 1H), 2.95 (dd, J=12.7, 5.3 Hz, 1H), 2.65 (tt, J=6.3, 5.8 Hz, 1H), 2.29 (s, 3H), 2.19 (td, J=9.1, 7.4 Hz, 1H), 1.85-1.75 (m, 1H), 1.67-1.49 (m, 3H); $^{13}$C-NMR (126 MHz, DMSO-d$_6$) δ 147.6, 135.6, 127.9, 126.0, 121.9, 120.8, 119.0, 116.7, 111.7, 101.4, 64.5, 56.8, 52.3, 40.6, 39.9, 28.23, 22.2; mp=170-172° C.; HRMS calculated (C$_{16}$H$_{19}$N$_5$, MH$^+$) 282.1713, found 282.1716.

5-(1-(2-(N,N-Dimethylamino)ethyl)-1H-1,2,3-triazol-4-yl)-1H-indole (IND12): The same method as IND1 was used. 2-Azidoethyldimethylamine (0.0395 g, 0.35 mmol) from method C was reacted with 5-ethynyl-1H-indole (0.0546 g, 0.39 mmol) for overnight and purified by column chromatography (5% CH$_3$OH in CH$_2$Cl$_2$) to obtain a pale yellow solid compound (84.66%). FTIR (ATR) (cm$^{-1}$) 3116, 3084, 3053, 2974, 2942, 2818, 2780, 1618, 1553, 1444, 1425, 1342, 1331, 1224, 1157, 1134, 1108, 1052, 1025, 881, 813, 763, 729; $^1$H-NMR (500 MHz, DMSO-d$_6$) δ 8.42 (s, 1H), 8.01 (s, 1H), 7.58 (dd, J=8.4, 1.6 Hz, 1H), 7.44 (d, J=8.4 Hz, 1H), 7.36 (d, J=2.7 Hz, 1H), 6.47 (ddd, J=2.8, 2.0, 0.8 Hz, 1H), 4.47 (t, J=6.4 Hz, 2H), 2.74 (t, J=6.3 Hz, 2H), 2.20 (s, 6H); $^{13}$C-NMR (126 MHz, DMSO-d$_6$) δ 147.7, 135.6, 127.9, 126.0, 121.9, 120.3, 119.0, 116.7, 111.7, 101.4, 58.3, 47.4, 45.0; mp=102-104° C.; HRMS calculated (C$_{14}$H$_{17}$N$_5$, MH$^+$) 256.1557, found 256.1564.

5-(1-(2-(Pyrrolidin-1-yl)ethyl)-1H-1,2,3-triazol-4-yl)-1H-indole (IND13): The same method as IND1 was used. 1-(2-Azidoethyl)pyrrolidine (0.0483 g, 0.34 mmol) from method C was reacted with 5-ethynyl-1H-indole (0.0489 g, 0.35 mmol) for overnight and purified by column chromatography (10% CH$_3$OH in EtOAc) to obtain a white solid compound (74.69%). FTIR (ATR) (cm$^{-1}$) 3304, 3152, 3080, 2968, 2924, 2775, 1618, 1547, 1479, 1448, 1432, 1347, 1333, 1230, 1137, 1056, 896, 793, 773, 745; $^1$H-NMR (400 MHz, DMSO-d$_6$) δ 8.45 (s, 1H), 8.09-7.96 (m, 1H), 7.59 (d, J=8.9 Hz, 1H), 7.44 (d, J=8.5 Hz, 1H), 7.37 (s, 1H), 6.47 (s, 1H), 4.49 (t, J=6.2 Hz, 2H), 3.32 (br s, 4H), 2.91 (t, J=6.4 Hz, 2H), 1.67 (br s, 4H); $^{13}$C-NMR (126 MHz, DMSO-d$_6$) δ 147.7, 135.6, 127.9, 126.0, 121.9, 120.3, 119.0, 116.7, 111.7, 101.3, 55.1, 53.4, 48.7, 23.1; mp=174.5-176° C.; HRMS calculated (C$_{16}$H$_{19}$N$_5$, MH$^+$) 282.1713, found 282.1715.

5-(1-(2-(Azepan-1-yl)ethyl)-1H-1,2,3-triazol-4-yl)-1H-indole (IND14): The same method as IND1 was used. 1-(2-Azidoethyl)azepane (0.0632 g, 0.38 mmol) from method A and 5-ethynyl-1H-indole (0.0521 g, 0.37 mmol) was reacted for overnight and purified by column chromatography (5% CH$_3$OH in EtOAc) to obtain a white solid compound (19.02%). FTIR (ATR) (cm$^{-1}$) 3287, 3142, 3087, 2923, 2817, 1621, 1547, 1480, 1447, 1432, 1341, 1327, 1226, 1124, 1057, 883, 787, 767, 735; $^1$H-NMR (500 MHz, CD$_3$OD) δ 8.24 (s, 1H), 8.00 (d, J=1.2 Hz, 1H), 7.56 (dd, J=8.4, 1.6 Hz, 1H), 7.44 (d, J=8.4 Hz, 1H), 7.26 (d, J=3.1 Hz, 1H), 6.49 (dd, J=3.1, 0.6 Hz, 1H), 4.53 (t, J=6.5 Hz, 2H), 3.07 (t, J=6.5 Hz, 2H), 2.78-2.72 (m, 4H), 1.70-1.57 (m, 8H); $^{13}$C-NMR (126 MHz, DMSO-d$_6$) δ 147.6, 135.6, 127.9, 126.0, 122.0, 120.3, 118.9, 116.6, 111.7, 101.3, 56.7, 54.5, 47.9, 28.0, 26.5; mp=128.5-129.5° C.; HRMS calculated (C$_{18}$H$_{23}$N$_5$, MH$^+$) 310.2026, found 310.2026.

1-(2-(4-(Benzo-1,3-dioxol-5-yl)-1,2,3-triazol-1-yl)ethyl)piperidine (PPRD1): The same method as IND1 was used. 1-(2-Azidoethyl)piperidine (0.024 g, 0.16 mmol) and 5-ethynyl-1,3-benzodioxole (0.038 g, 0.26 mmol) were reacted for overnight and purified by column chromatography (0-5% CH$_3$OH in CH$_2$Cl$_2$ with 1% Et$_3$N added) to give the product as a white powder (77.01%). FTIR (ATR) (cm$^{-1}$) 3135, 3107, 2995, 2929, 2853, 2791, 1607, 1563, 1487, 1461, 1374, 1235, 1214, 1192, 1120, 1106, 1038, 940, 881, 862, 811, 745; $^1$H-NMR (300 MHz, DMSO-d$_6$) δ 8.43 (s, 1H), 7.37 (d, J=1.5 Hz, 1H), 7.34 (dd, J=8.0, 1.6 Hz, 1H), 6.99 (d, J=8.0 Hz, 1H), 6.05 (s, 2H), 4.46 (t, J=6.5 Hz, 2H), 2.72 (t, J=6.5 Hz, 2H), 2.42-2.35 (m, 4H, H2), 1.46 (dt, J=10.6, 5.4 Hz, 4H), 1.41-1.32 (m, 2H); $^{13}$C-NMR (76 MHz, CDCl$_3$) δ 148.2, 147.5, 147.5, 125.2, 119.9, 119.4, 108.8, 106.5, 101.3, 58.4, 54.7, 48.0, 26.1, 24.3; mp=110-111° C.; HRMS calculated (C$_{16}$H$_{20}$N$_4$O$_2$, MH$^+$) 301.1659, found 301.1657.

1-(2-(4-Aminophenyl-1,2,3-triazol-1-yl)ethyl)piperidine (PPRD2): The same method as IND1 was used. 1-(2-Azidoethyl)piperidine (0.031 g, 0.20 mmol) and 4-ethynylaniline (0.022 g, 0.19 mmol) were reacted for overnight. The crude product was purified by column chromatography (0-1% CH$_3$OH in CH$_2$Cl$_2$ with 1% Et$_3$N added) followed by washing with diethyl ether with a few drops of CH$_3$OH added to remove traces of the azide. The product was isolated as a pale yellow powder (56.91%). FTIR (ATR) (cm$^{-1}$) 3326, 3207, 3030, 2941, 2909, 2811, 1628, 1500, 1466, 1425, 1365, 1350, 1299, 1210, 1178, 1049, 830, 791, 758; $^1$H-NMR (300 MHz, CD$_2$Cl$_2$) δ 7.82 (s, 1H), 7.59 (d, J=8.5 Hz, 2H), 6.73 (d, J=8.6 Hz, 2H), 4.45 (t, J=6.3 Hz, 2H), 3.83 (s, 2H), 2.77 (t, J=6.3 Hz, 2H), 2.50-2.41 (m, 4H), 1.58 (dt, J=11.0, 5.6 Hz, 4H), 1.44 (dt, J=11.3, 5.8 Hz, 2H); $^{13}$C-NMR (76 MHz, CD$_2$Cl$_2$) δ 148.1, 147.3, 127.2, 121.8, 119.6, 115.5, 58.9, 55.1, 48.3, 26.6, 24.8; mp=147-148° C.; HRMS calculated (C$_{15}$H$_{21}$N$_5$, MH$^+$) 272.1870, found 272.1869.

1-(2-(4-(4-Methoxyphenyl)-1,2,3-triazol-1-yl)ethyl)piperidine (PPRD3): The same method as IND1 was used. 1-(2-Azidoethyl)piperidine (0.025 g, 0.16 mmol) was reacted with 1-ethynyl-4-methoxybenzene (0.025 g, 0.19 mmol) for 44 h. The crude product was purified by column chromatography (0-1% CH$_3$OH in CH$_2$Cl$_2$ with 1% Et$_3$N added) followed by washing with diethyl ether with a few drops of CH$_3$OH added to removed traces of the azide. The product was isolated as a white powder (58.16%). FTIR (ATR) (cm$^{-1}$) 3123, 3103, 2932, 2850, 2803, 1613, 1559, 1499, 1456, 1441, 1241, 1175, 1021, 835, 805, 736; $^1$H-NMR (300 MHz, CD$_2$Cl$_2$) δ 7.89 (s, 1H), 7.75 (d, J=8.8 Hz, 2H), 6.69 (d, J=8.8 Hz, 2H), 4.47 (t, J=6.2 Hz, 2H), 3.83 (s, 3H), 2.79 (t, J=6.2 Hz, 2H), 2.46 (br s, 4H), 1.58 (dt, J=11.0, 5.5 Hz, 4H), 1.45 (dt, J=10.7, 5.7 Hz, 2H); $^{13}$C-NMR (76 MHz, CD$_2$Cl$_2$) δ 160.1, 147.6, 127.3, 124.3, 120.2, 114.7, 58.8, 55.8, 55.1, 48.3, 26.6, 24.8; mp=110-111° C.; HRMS calculated (C$_{16}$H$_{22}$N$_4$O, MH$^+$) 287.1866, found 287.1867.

1-(2-(4-Tolyl-1,2,3-triazol-1-yl)ethyl)piperidine (PPRD4): The same method as IND1 was used. 1-(2-Azidoethyl)piperidine (0.0476 g, 0.31 mmol) was reacted with 1-ethynyl-4-methylbenzene (0.0407 g, 0.35 mmol) for overnight and purified by column chromatography (20% hexane in EtOAc) to give pale orange solid compound (69.62%). FTIR (ATR) (cm$^{-1}$) 3131, 3108, 2922, 2851, 2804, 2782, 1559, 1499, 1438, 1214, 1108, 1039, 817, 743; $^1$H-NMR (500 MHz, CDCl$_3$) δ 7.90 (s, 1H), 7.72 (d, J=8.1 Hz, 2H), 7.23 (d, J=7.9 Hz, 2H), 4.52 (t, J=6.4 Hz, 2H), 2.84 (t, J=6.3 Hz, 2H), 2.48 (br s, 4H), 2.38 (s, 3H), 1.65-1.56 (m, 4H), 1.51-1.41 (m, 2H); $^{13}$C-NMR (126 MHz, CDCl$_3$) δ 147.8, 138.0, 129.6, 128.2, 125.8, 120.1, 58.4, 54.7, 47.9, 26.0, 24.2, 21.4; mp=113-114° C.; HRMS calculated (C$_{16}$H$_{22}$N$_4$, MH$^+$) 271.1917, found 271.1918.

5-((1-(2-Piperidin-1-yl)ethyl)-1,2,3-triazol-4-yl)-indole-3-carbaldehyde (PPRD5): The same method as IND1 was used. 1-(2-Azidoethyl)piperidine (0.023 g, 0.15 mmol) was reacted with 5-ethynyl-indole-3-carbaldehyde (0.028 g, 0.17 mmol) for 3 d and purified by column chromatography (0-2% CH$_3$OH in CH$_2$Cl$_2$ with 1% Et$_3$N added) followed by washing with diethyl ether with a few drops of CH$_3$OH added to removed traces of the azide. The product was isolated as a pale yellow powder (74.64%). FTIR (ATR) (cm$^{-1}$) 3228, 3205, 2927, 2798, 2848, 2753, 1631, 1520, 1429, 1384, 1238, 1119, 1095, 802, 787, 730, 678; $^1$H-NMR (300 MHz, DMSO-d$_6$) δ 12.21 (s, 1H), 9.95 (s, 1H), 8.56 (d, J=1.2 Hz, 1H), 8.54 (s, 1H), 8.32 (d, J=3.0 Hz, 1H), 7.75 (dd, J=8.5, 1.5 Hz, 1H), 7.57 (d, J=8.5 Hz, 1H), 4.49 (t, J=6.5 Hz, 2H), 2.77 (t, J=6.5 Hz, 2H), 2.45-2.35 (m, 4H), 1.46 (dd, J=9.1, 4.5 Hz, 4H), 1.41-1.31 (m, 2H); mp=155-158° C.; HRMS calculated (C$_{18}$H$_{21}$N$_5$O, MH$^+$) 324.1819, found 324.1821.

1-(2-(4-(6-Methoxynaphthalen-2-yl)-1H-1,2,3-triazol-1-yl)ethyl)piperidine (PPRD6): The same method as IND1 was used. 1-(2-Azidoethyl)piperidine (0.025 g, 0.16 mmol) was reacted with 2-ethynyl-6-methoxynaphthalene (0.034 g, 0.19 mmol) for overnight and purified by column chromatography (CH$_2$Cl$_2$ with 1% Et$_3$N added) followed by washing with diethyl ether with a few drops of CH$_3$OH added to removed traces of the azide. The product was isolated as a white powder (62.34%). FTIR (ATR) (cm$^{-1}$) 3119, 3070, 2931, 2847, 2795, 1610, 1449, 1257, 1215, 1164, 1123, 1022, 907, 889, 860, 815, 804; $^1$H-NMR (300 MHz, CD$_2$Cl$_2$) δ 8.25 (s, 1H), 8.06 (s, 1H), 7.91 (dd, J=8.5, 1.5 Hz, 1H), 7.81 (d, J=8.5 Hz, 2H), 7.20-7.14 (m, 2H), 4.49 (t, J=6.2 Hz, 2H), 3.92 (s, 3H), 2.80 (t, J=6.2 Hz, 2H), 2.47 (br s, 4H), 1.59 (dt, J=11.1, 5.6 Hz, 4H), 1.46 (dd, J=11.1, 5.8 Hz, 2H); $^{13}$C-NMR (76 MHz, CD$_2$Cl$_2$) δ 158.4, 147.9, 134.8, 130.1, 129.5, 127.8, 126.9, 124.9, 124.4, 120.9, 119.7, 106.3, 58.8, 55.8, 55.1, 48.4, 26.6, 24.8; mp=143.5-144.5° C.; HRMS calculated (C$_{20}$H$_{24}$N$_4$O, MH$^+$) 337.2023, found 337.2024.

1-(2-(4-(Biphenyl-4-yl)-1,2,3-triazol-1-yl)ethyl)piperidine (PPRD7): The same method as IND1 was used. 1-(2-Azidoethyl)piperidine (0.0552 g, 0.36 mmol) was reacted with 4-ethynylbiphenyl (0.0630 g, 0.35 mmol) for overnight. After that, the reaction mixture was purified by column chromatography (5% CH$_3$OH in CH$_2$Cl$_2$) to obtain white solid compound (26.04%). FTIR (ATR) (cm$^{-1}$) 3101, 3034, 2927, 2846, 2768, 1485, 1439, 1220, 1106, 1042, 842, 813, 762, 720, 634; $^1$H-NMR (500 MHz, CDCl$_3$) δ 8.01 (s, 1H), 7.91 (d, J=8.2 Hz, 2H), 7.67 (d, J=8.2 Hz, 2H), 7.64 (d, J=7.4 Hz, 2H), 7.46 (t, J=7.7 Hz, 2H), 7.36 (t, J=7.5 Hz, 1H), 4.58 (t, J=6.0 Hz, 2H), 2.95-2.84 (m, 2H), 2.52 (br s, 4H), 1.64 (dt, J=10.1, 5.6 Hz, 4H), 1.53-1.42 (m, 2H); $^{13}$C-NMR (126 MHz, DMSO-d$_6$) δ 147.5, 141.0, 140.8, 129.0, 127.7, 127.6, 127.1, 126.2, 120.6, 99.7, 58.3, 54.7, 47.8, 31.1, 25.9, 24.1; mp=162-163° C.; HRMS calculated (C$_{21}$H$_{24}$N$_4$, MH$^+$) 333.2074, found 333.2075.

1-(2-(4-Aminophenyl-1,2,3-triazol-1-yl)ethyl)piperidine (PPRD8): The same method as IND1 was used. 1-(2-Azidoethyl)piperidine (0.0535 g, 0.35 mmol) was reacted with 4-ethynylphenol (0.0385 g, 0.33 mmol) for overnight. After that, the reaction mixture was purified by column chromatography (5% CH$_3$OH in EtOAc) to obtain a white solid compound (38.87%). FTIR (ATR) (cm$^{-1}$) 3349, 3228, 3144, 2927, 2851, 2806, 1619, 1498, 1456, 1357, 1273, 1212, 836, 794; $^1$H-NMR (500 MHz, DMSO-d$_6$) δ 9.55 (s, 1H), 8.33 (s, 1H), 7.62 (d, t, J=8.5 Hz, 2H), 6.82 (d, J=8.6 Hz, 2H), 4.45 (t, J=6.5 Hz, 2H), 2.72 (t, J=6.5 Hz, 2H), 2.46-2.30 (m, 4H), 1.46 (dt, J=10.9, 5.4 Hz, 4H), 1.36 (dt, J=10.3, 5.4 Hz, 2H); $^{13}$C-NMR (126 MHz, DMSO-d$_6$) δ 157.1, 146.4, 126.5, 121.9, 120.2, 115.6, 57.8, 53.8, 47.1, 25.5, 23.9; mp=175.5-177° C.; HRMS calculated (C$_{15}$H$_{20}$N$_4$O, MH$^+$) 273.1710, found 273.1706.

1-(2-((1-Methyl-5-indolyl)-1,2,3-triazol-1-yl)ethyl)piperidine (PPRD9): The same method as IND1 was used. 1-(2-Azidoethyl)piperidine (0.022 g, 0.14 mmol) was reacted with 5-ethynyl-methylindole (0.039 g, 0.25 mmol) for overnight and purified by column chromatography (CH$_2$Cl$_2$ with 1% Et$_3$N added) followed by washing with diethyl ether with a few drops of CH$_3$OH added to remove traces of the azide. The product was isolated as a white powder (81.56%). FTIR (ATR) (cm$^{-1}$) 3080, 2931, 2806, 2775, 1509, 1479, 1437, 1247, 1216, 1156, 802, 726; $^1$H-NMR (300 MHz, CD$_2$Cl$_2$) δ 8.05 (d, J=1.2 Hz, 1H), 7.95 (s, 1H), 7.70 (dd, J=8.5, 1.5 Hz, 1H), 7.39 (d, J=8.5 Hz, 1H), 7.11 (d, J=3.1 Hz, 1H), 6.51 (d, J=3.0 Hz, 1H), 4.47 (t, J=6.3 Hz, 2H), 3.80 (s, 3H), 2.80 (t, J=6.3 Hz, 2H), 2.50-2.42 (m, 4H), 1.59 (dt, J=11.0, 5.6 Hz, 4H), 1.45 (dt, J=10.9, 5.7 Hz, 2H); $^{13}$C-NMR (76 MHz, CD$_2$Cl$_2$) δ 149.1, 137.1, 130.2, 129.3, 123.0, 120.1, 120.1, 118.3, 110.1, 101.6, 58.9, 55.1, 48.3, 33.4, 26.6, 24.8; mp=107-108° C.; HRMS calculated (C$_{18}$H$_{23}$N$_5$, MH$^+$) 310.2026, found 310.2025.

9-((1-(2-(Piperidin-1-yl)ethyl)-1,2,3-triazol-4-yl)methyl)-purin-6-amine (PPRD10): The same method as IND1 was used. 1-(2-Azidoethyl)piperidine (0.025 g, 0.16 mmol) and 9-(propargyl)adenine (0.029 g, 0.17 mmol) were reacted for 4 d. The crude product was purified by column chromatography (0-10% CH$_3$OH in CH$_2$Cl$_2$ with 1% Et$_3$N added) followed by washing with diethyl ether with a few drops of CH$_3$OH added to removed traces of the azide. The product was isolated as a pale yellow powder (30.15%). $^1$H-NMR (300 MHz, CD$_2$Cl$_2$) δ 8.32 (s, 1H), 7.95 (s, 1H), 7.85 (s, 1H), 5.90 (br s, 2H), 5.46 (s, 2H), 4.43 (t, J=6.1 Hz, 2H), 2.73 (t, J=6.1 Hz, 2H), 2.45-2.35 (m, 4H), 1.52 (dt, J=10.7, 5.4 Hz, 4H), 1.41 (dt, J=11.3, 5.5 Hz, 2H); mp=149-151° C.; HRMS calculated (C$_{15}$H$_{21}$N$_9$, MH$^+$) 328.1993, found 328.1992.

Methyl 3-(1-(2-(piperidin-1-yl)ethyl)-1H-1,2,3-triazol-4-yl)-1H-indole-5-carboxylate (PPRD11): The same method as IND1 was used. 1-(2-Azidoethyl)piperidine (0.0459 g, 0.30 mmol) was reacted with methyl 3-ethynyl-1H-indole-5-carboxylate (0.0654 g, 0.33 mmol) for overnight. After that, the reaction mixture was purified by column chromatography (5% CH$_3$OH in EtOAc) to obtain white solid compound (33.94%). FTIR (ATR) (cm$^{-1}$) 3232, 3110, 2931, 1696, 1619, 1429, 1254, 1232, 1209, 813, 745; $^1$H-NMR (500 MHz, CDCl$_3$) 9.68 (s, 1H), 8.61 (s, 1H), 8.05 (s, 1H), 7.92 (dd, J=8.6, 1.1 Hz, 1H), 7.76 (d, J=2.3 Hz, 1H), 7.43 (d, J=8.6 Hz, 1H), 4.54 (t, J=6.3 Hz, 2H), 3.92 (s, 3H), 2.85 (t, J=6.3 Hz, 2H), 2.59-2.43 (m, 4H), 1.68-1.57 (m, 4H), 1.46 (dt, J=12.2, 6.2 Hz, 2H); $^{13}$C-NMR (126 MHz, CDCl$_3$) δ 168.3, 142.1, 139.2, 124.9, 124.0, 123.8, 122.5, 122.4, 120.0, 111.6, 108.8, 58.4, 54.7, 52.0, 48.0, 26.1, 24.3; mp=162-163° C.; HRMS calculated ($C_{19}H_{23}N_5O_2$, MH$^+$) 354.1924, found 354.1930.

1-(2-(3-Indolyl-1,2,3-triazol-1-yl)ethyl)piperidine (PPRD12): The same method as IND1 was used. 1-(2-Azidoethyl)piperidine (0.0367 g, 0.24 mmol) was reacted with 3-ethynyl-1H-indole (0.0331 g, 0.23 mmol) for overnight. After that, the reaction mixture was concentrated and purified by column chromatography (5% $CH_3OH$ in EtOAc). After that the trace azide was washed out by using a few drops of $CH_3OH$ in diethyl ether to give white solid compound (42.16%). FTIR (ATR) (cm$^{-1}$) 3129, 3045, 2936, 2807, 1601, 1447, 1429, 1226, 1128, 914, 795; $^1$H-NMR (400 MHz, DMSO-d$_6$) δ 8.39 (s, 1H), 8.00 (d, J=7.8 Hz, 1H), 7.77 (d, J=2.5 Hz, 1H), 7.47-7.41 (m, 1H), 7.15 (ddd, J=8.0, 6.9, 1.1 Hz, 1H), 7.10 (ddd, J=8.0, 7.0, 1.2 Hz, 1H), 4.50 (t, J=6.6 Hz, 2H), 2.77 (t, J=6.6 Hz, 2H), 2.47-2.37 (m, 4H), 1.54-1.42 (m, 4H), 1.42-1.31 (m, 2H). $^{13}$C-NMR (101 MHz, DMSO-d$_6$) δ 142.2, 136.3, 124.7, 122.8, 121.5, 119.8, 119.7, 119.4, 111.7, 106.4, 57.9, 53.8, 47.0, 39.5, 25.6, 23.9; mp=151-152° C.; HRMS calculated ($C_{17}H_{21}N_5$, MH$^+$) 296.1870, found 296.1871.

1-(2-(4-(4-Chlorophenyl)-1,2,3-triazol-1-yl)ethyl)piperidine (PPRD13): The same method as IND1 was used. 1-(2-Azidoethyl)piperidine (0.0541 g, 0.35 mmol) was reacted with 1-chloro-4-ethynylbenzene (0.0543 g, 0.40 mmol) in 1 to 1 to 1 ratio of THF, t-BuOH and water for overnight. After that, the reaction mixture was purified by column chromatography (5% $CH_3OH$ in $CH_2Cl_2$). The trace azide was washed out by using cold diethyl ether to give white solid compound (83.62%). FTIR (ATR) (cm$^{-1}$) 3133, 2931, 2912, 2806, 2764, 1547, 1486, 1448, 1437, 1224, 1087, 817; $^1$H-NMR (500 MHz, CD$_3$OD) δ 8.36 (s, 1H), 7.83-7.77 (m, 2H), 7.46-7.41 (m, 2H), 4.57 (t, J=6.7 Hz, 2H), 2.87 (t, J=6.7 Hz, 2H), 2.58-2.44 (m, 4H), 1.59 (dt, J=11.3, 5.6 Hz, 4H), 1.46 (dt, J=11.0, 5.5 Hz, 2H); $^{13}$C-NMR (101 MHz, CD$_3$OD) δ 147.6, 135.0, 130.6, 130.1, 128.1, 122.9, 59.2, 55.5, 48.8, 26.8, 25.1; mp=132-133.5° C.; HRMS calculated ($C_{15}H_{19}ClN_4$, MH$^+$) 291.1371, found 291.1371.

Methyl 2-hydroxy-5-(1-(2-(piperidin-1-yl)ethyl)-1,2,3-triazol-4-yl)benzoate (PPRD14): The same method as IND1 was used. 1-(2-Azidoethyl)piperidine (0.0655 g, 0.42 mmol) was reacted with methyl 5-ethynyl-2-hydroxybenzoate (0.0744 g, 0.42 mmol) in 1 to 1 to 1 ratio of THF, t-BuOH and water for overnight and purified by column chromatography (3% $CH_3OH$ in $CH_2Cl_2$). The trace azide was washed out by using a few drops of $CH_2Cl_2$ in diethyl ether to give white solid compound (54.69%). FTIR (ATR) (cm$^{-1}$) 3205, 3133, 2931, 2851, 2798, 2779, 1676, 1619, 1593, 1483, 1437, 1361, 1327, 1292, 1209, 832, 794, 718; $^1$H-NMR (500 MHz, DMSO-d$_6$) 10.54 (s, 1H), 8.52 (s, 1H), 8.25 (d, J=2.1 Hz, 1H), 7.95 (dd, J=8.6, 2.2 Hz, 1H), 7.08 (d, J=8.6 Hz, 1H), 4.48 (t, J=6.3 Hz, 2H), 3.93 (s, 3H), 2.75 (br s, 2H), 2.40 (br s, 4H), 1.54-1.41 (m, 4H), 1.41-1.30 (m, 2H); $^{13}$C-NMR (126 MHz, DMSO-d$_6$) δ 168.8, 159.4, 145.1, 132.3, 126.3, 122.5, 121.0, 118.1, 113.6, 57.7, 53.8, 52.5, 47.1, 25.5, 23.8; mp=101-102° C.; HRMS calculated ($C_{17}H_{22}N_4O_3$, MH$^+$) 331.1765, found 331.1766.

Methyl 2-amino-5-(1-(2-(piperidin-1-yl)ethyl)-1,2,3-triazol-4-yl)benzoate (PPRD15): The same method as IND1 was used. 1-(2-Azidoethyl)piperidine (0.0668 g, 0.43 mmol) was reacted with methyl 2-amino-5-ethynylbenzoate (0.0745 g, 0.43 mmol) in 1 to 1 to 1 ratio of THF, t-BuOH and water for overnight and purified by column chromatography (3% $CH_3OH$ in $CH_2Cl_2$). After that the trace azide was washed out by diethyl ether to give white solid compound (42.05%). FTIR (ATR) (cm$^{-1}$) 3460, 3357, 3133, 2935, 2848, 2802, 1692, 1627, 1589, 1490, 1433, 1296, 1235, 1194, 1163, 1099, 829, 791; $^1$H-NMR (500 MHz, CD$_3$OD) δ 8.26 (d, J=2.1 Hz, 1H), 8.18 (s, 1H), 7.68 (dd, J=8.6, 2.1 Hz, 1H), 6.83 (d, J=8.6 Hz, 1H), 4.54 (t, J=6.8 Hz, 2H), 3.88 (s, 3H), 2.87 (t, J=6.8 Hz, 2H), 2.54-2.46 (m, 4H), 1.60 (dt, J=11.2, 5.6 Hz, 4H), 1.47 (dt, J=10.6, 5.7 Hz, 2H); $^{13}$C-NMR (126 MHz, DMSO-d$_6$) δ 167.7, 150.9, 146.0, 131.3, 127.0, 119.9, 117.8, 117.1, 108.7, 57.8, 53.8, 51.5, 47.1, 25.5, 23.9; mp=82-84° C.; HRMS calculated ($C_{17}H_{23}N_5O_2$, MH$^+$) 330.1924, found 330.1927.

3-(4-(Benzo-1,3-dioxol-5-yl)-1,2,3-triazol-1-yl)quinuclidine (QND1): The same method as IND1 was used. 3-Azidoquinuclidine (0.0581 g, 0.38 mmol) in THF, t-BuOH and water (1:1:1) was reacted with 5-ethynyl-1,3-benzodioxole (0.0696 g, 0.48 mmol) for overnight. The crude product was purified by column chromatography (5-10% $CH_3OH$ in $CH_2Cl_2$). The trace azide was washed out by a few drops of $CH_2Cl_2$ in diethyl ether to give white solid compound (56.46%). FTIR (ATR) (cm$^{-1}$) 3132, 3106, 2931, 2863, 1608, 1562, 1479, 1445, 1239, 1209, 1030, 802; $^1$H-NMR (500 MHz, CD$_3$OD) δ 8.33 (s, 1H), 7.35-7.30 (m, 2H), 6.88 (d, J=7.9 Hz, 1H), 5.98 (s, 2H), 4.85-4.79 (m, 1H), 3.73 (dd, J=14.3, 5.1 Hz, 1H), 3.48 (ddd, J=12.5, 10.0, 2.0 Hz, 1H), 3.21-3.08 (m, 1H), 3.01-2.86 (m, 3H), 2.31-2.24 (m, 1H), 1.89 (td, J=7.9, 2.9 Hz, 2H), 1.69-1.51 (m, 2H); 13C-NMR (126 MHz, DMSO-d$_6$) δ 149.7, 149.2, 148.7, 125.8, 121.6, 120.5, 109.6, 107.1, 102.7, 59.2, 52.4, 49.0, 47.8, 47.5, 29.2, 26.1, 20.6; mp=162-164° C.; HRMS calculated ($C_{16}H_{15}N_4O_2$, MH$^+$) 299.1502, found 299.1500.

3-(4-Aminophenyl-1,2,3-triazol-1-yl)quinuclidine (QND2): The same method as IND1 was used. 3-Azidoquinuclidine (0.051 g, 0.34 mmol) was reacted with 4-ethynylaniline (0.051 g, 0.44 mmol) for 3 d followed by purification with column chromatography (0-5% $CH_3OH$ in $CH_2Cl_2$ with 1% $Et_3N$ added) and washing with a few drops of $CH_3OH$ added in diethyl ether to remove traces of the 3-azidoquinuclidine. The product was isolated as a white to pale yellow powder (67.59%). FTIR (ATR) (cm$^{-1}$) 3387, 3318, 3166, 3106, 2938, 2917, 2864, 1646, 1610, 1491, 1467, 1307, 1176, 1054, 837, 798, 784; $^1$H-NMR (300 MHz, DMSO-d$_6$) δ 8.40 (s, 1H), 7.52 (d, J=7.9 Hz, 2H), 6.61 (d, J=7.9 Hz, 2H), 5.21 (br s, 2H), 4.72-4.65 (m, 1H), 3.45 (dd, J=14.3, 5.0 Hz, 1H), 3.34 (d, J=14.9 Hz, 1H), 3.02-2.91 (m, 1H), 2.82-2.69 (m, 3H), 2.19-2.12 (m, 1H), 1.79-1.62 (m, 2H), 1.49-1.30 (m, 2H); $^{13}$C-NMR (76 MHz, DMSO-d$_6$) 148.5, 147.1, 126.1, 118.6, 118.5, 113.9, 57.1, 51.8, 46.6, 46.4, 27.7, 25.3, 19.6; mp=223-224° C.; HRMS calculated ($C_{15}H_{19}N$, MH$^+$) 270.1713, found 270.1713.

3-(4-(4-Methoxyphenyl)-1,2,3-triazol-1-yl)quinuclidine (QND3): The same method as IND1 was used. 3-Azidoquniclidine (0.051 g, 0.34 mmol) was reacted with 1-ethynyl-4-methoxybenzene (0.049 g, 0.37 mmol) for overnight and purified by column chromatography (0-10% $CH_3OH$ in $CH_2Cl_2$ with 1% $Et_3N$ added) followed by washing with a few drops of $CH_3OH$ added in diethyl ether to remove traces of the azide. The product was isolated as a white powder (59.82%). FTIR (ATR) (cm$^{-1}$) 3133, 3110, 2935, 2863, 1616, 1559, 1494, 1452, 1441, 1251, 1178, 1030, 836, 794; $^1$H-NMR (500 MHz, CD$_2$Cl$_2$) δ 7.79 (s, 1H), 7.76 (d, J=8.4 Hz, 2H), 6.96 (d, J=8.4 Hz, 2H), 4.67-4.56 (m, 1H), 3.83 (s, 3H), 3.64 (dd, J=14.5, 4.4 Hz, 1H), 3.51-3.40 (m, 1H), 3.13-3.04 (m, 1H), 2.96-2.80 (m, 3H), 2.27-2.21 (m, 1H), 1.87-1.72 (m, 2H), 1.69-1.58 (m, 1H), 1.50-1.40 (m, 1H); $^{13}$C-NMR (126 MHz, CD$_2$Cl$_2$) δ 160.2, 147.6, 127.4, 124.2, 119.0, 114.7, 58.8, 55.8, 53.1, 47.8, 47.4, 28.8, 26.5, 20.6; mp=139-141° C.; HRMS calculated ($C_{16}H_{20}N_4O$, MH$^+$) 285.1710, found 285.1711.

3-(4-Tolyl-1,2,3-triazol-1-yl)quinuclidine (QND4): The same method as IND1 was used. 3-Azidoquinuclidine (0.0554 g, 0.36 mmol) was reacted with 1-ethynyl-4-methylbenzene (0.0412 g, 0.35 mmol) for overnight. The crude product was evaporated and purified by column chromatography (5% Et$_3$N and 5% CH$_3$OH in CH$_2$Cl$_2$) to give a white solid compound (70.88%). FTIR (ATR) (cm$^{-1}$) 3129, 2943, 2863, 1494, 1448, 1315, 1220, 1037, 969, 829, 806, 787; $^1$H-NMR (500 MHz, CD$_3$OD) δ 8.39 (s, 1H), 7.71 (d, J=8.1 Hz, 2H), 7.26 (d, J=8.1 Hz, 2H), 4.96-4.91 (m, 1H), 3.88 (dd, J=14.3, 5.3 Hz, 1H), 3.63-3.55 (m, 1H), 3.29-3.22 (m, 1H), 3.09-3.00 (m, 3H), 2.37 (s, 3H), 2.36-2.35 (m, 1H), 1.96 (td, J=8.4, 3.2 Hz, 2H), 1.74-1.59 (m, 2H); $^{13}$C-NMR (101 MHz, CD$_3$OD) δ 149.0, 139.5, 130.6, 128.9, 126.7, 121.8, 59.0, 52.3, 47.8, 47.5, 29.2, 25.9, 21.3, 20.4; mp=155.5-157.5° C.; HRMS calculated ($C_{16}H_{20}N_4$, MH$^+$) 269.1761, found 269.1760.

5-(1-(Quinuclidin-3-yl)-1,2,3-triazol-4-yl)-indole-3-carbaldehyde (QND5): The same method as IND1 was used. 3-Azidoquinuclidine (0.0407 g, 0.27 mmol) was reacted with 5-ethynyl-1H-indole-3-carbaldehyde (0.0332 g, 0.20 mmol) for overnight. The crude product was purified by column chromatography (5% Et$_3$N and 5% CH$_3$OH in CH$_2$Cl$_2$) to give a white solid compound (71.83%). FTIR (ATR) (cm$^{-1}$) 3121, 3099, 2946, 2931, 2878, 2810, 1650, 1448, 1235, 1125, 1049, 878, 817, 779, 669; $^1$H-NMR (500 MHz, DMSO-d$_6$) δ 9.96 (s, 1H), 8.74 (s, 1H), 8.61 (s, 1H), 8.32 (s, 1H), 7.81 (d, J=8.6 Hz, 1H), 7.57 (d, J=8.3 Hz, 1H), 4.75 (br s, 1H), 3.50 (d, J=12.9 Hz, 1H), 3.39 (d, J=11.1 Hz, 1H), 3.07-2.94 (m, 1H), 2.85-2.69 (m, 3H), 2.21 (br s, 1H), 1.80-1.66 (m, 2H), 1.53-1.32 (m, 2H); $^{13}$C-NMR (126 MHz, DMSO-d$_6$) δ 184.9, 147.0, 139.1, 136.7, 125.3, 124.5, 121.4, 120.3, 118.4, 117.5, 112.8, 57.4, 51.8, 46.6, 46.4, 27.7, 25.4, 19.7; mp=276-277° C.; HRMS calculated ($C_{18}H_{19}N_5O$, MH$^+$) 322.1662, found 322.1665.

3-(4-(6-Methoxynaphthalen-2-yl)-1,2,3-triazol-1-yl)quinuclidine (QND6): The same method as IND1 was used. 3-Azidoquniclidine (0.025 mg, 0.16 mmol) and 2-ethynyl-6-methoxynaphthalene (0.034 g, 0.19 mmol) were reacted for 3 d and purified by column chromatography (0-5% CH$_3$OH in CH$_2$Cl$_2$ with 1% Et$_3$N added) followed by washing with a few drops of CH$_3$OH added in diethyl ether to remove traces of the azide. The product was isolated as a pale yellow powder (94.67%). FTIR (ATR) (cm$^{-1}$) 3144, 3060, 2931, 2863, 1604, 1448, 1433, 1258, 1216, 1159, 1045, 1023, 859, 813, 791; $^1$H-NMR (300 MHz, DMSO-d$_6$) δ 8.82 (s, 1H), 8.34 (s, 1H), 7.98 (dd, J=8.6, 1.3 Hz, 1H), 7.90 (d, J=6.3 Hz, 1H), 7.88 (d, J=7.3 Hz, 1H), 7.34 (d, J=2.3 Hz, 1H), 7.19 (dd, J=9.0, 2.5 Hz, 1H), 4.91-4.78 (m, 1H), 3.89 (s, 3H), 3.60-3.43 (m, 2H), 3.14-2.99 (m, 1H), 2.94-2.76 (m, 3H), 2.30-2.22 (m, 1H), 1.86-1.72 (m, 2H), 1.57-1.41 (m, 2H); $^{13}$C-NMR (76 MHz, DMSO-d$_6$) δ 157.4, 146.4, 133.9, 129.5, 128.6, 127.3, 126.1, 124.2, 123.4, 120.9, 119.2, 106.0, 57.1, 55.2, 51.6, 46.5, 46.3, 27.6, 24.9, 19.4; mp=164-166° C.; HRMS calculated ($C_{20}H_{22}N_4O$, MH$^+$) 335.1866, found 335.1868.

3-(4-(Biphenyl-4-yl)-1,2,3-triazol-1-yl)quinuclidine (QND7): The same method as IND1 was used. 3-Azidoquinuclidine (0.0556 g, 0.37 mmol) was reacted with 4-ethynylbiphenyl (0.0534 g, 0.30 mmol) for overnight. The crude product was purified by column chromatography (1% Et$_3$N and 5% CH$_3$OH in CH$_2$Cl$_2$) to give a white solid compound (74.95%). FTIR (ATR) (cm$^{-1}$) 3102, 3030, 2935, 2867, 1481, 1229, 1212, 838, 815, 764, 727, 694; $^1$H-NMR (400 MHz, CDCl$_3$) δ 7.95-7.89 (m, 2H), 7.86 (s, 1H), 7.70-7.65 (m, 2H), 7.65-7.62 (m, 2H), 7.49-7.42 (m, 2H), 7.39-7.33 (m, 1H), 4.74-4.65 (m, 1H), 3.76 (dd, J=14.3, 5.6 Hz, 1H), 3.60-3.48 (m, 1H), 3.26-3.14 (m, 1H), 3.07-2.89 (m, 3H), 2.34-2.28 (m, 1H), 1.92-1.79 (m, 2H), 1.79-1.67 (m, 1H), 1.58-1.45 (m, 1H); $^{13}$C-NMR (101 MHz, CDCl$_3$) δ 147.5, 141.0, 140.7, 129.7, 129.0, 127.7, 127.6, 127.1, 126.2, 119.2, 58.4, 52.7, 47.4, 47.1, 28.3, 26.0, 20.1; mp=200-201° C.; HRMS calculated ($C_{21}H_{22}N_4$, MH$^+$) 331.1917, found 331.1921

3-(4-Aminophenyl-1,2,3-triazol-1-yl)quinuclidine (QND8): The same method as IND1 was used. 3-Azidoquinuclidine (0.0626 g, 0.41 mmol) was reacted with 4-ethynylphenol (0.0413 g, 0.35 mmol) for overnight. The crude product was purified by column chromatography (10% Et$_3$N and 10% CH$_3$OH in CH$_2$Cl$_2$) to obtain a white solid compound (22.11%). FTIR (ATR) (cm$^{-1}$) 3129, 3034, 2950, 2882, 1615, 1559, 1449, 1412, 1278, 1249, 1224, 840, 790; $^1$H-NMR (400 MHz, DMSO-d$_6$) δ 9.58 (s, 1H), 8.52 (s, 1H), 7.74-7.61 (m, 2H), 6.89-6.79 (m, 2H), 4.76-4.66 (m, 1H), 3.49-3.43 (m, 1H), 3.34 (dd, J=11.1, 3.1 Hz, 1H), 3.05-2.91 (m, 1H), 2.86-2.70 (m, 3H), 2.22-2.11 (m, 1H), 1.81-1.63 (m, 2H), 1.50-1.30 (m, 2H); $^{13}$C-NMR (101 MHz, DMSO-d$_6$) δ 157.2, 146.5, 126.6, 121.9, 119.5, 115.6, 57.2, 51.8, 46.6, 46.4, 27.7, 25.3, 19.6; mp=260-261° C.; HRMS calculated ($C_{15}H_{18}N_4O$, MH$^+$) 271.1553, found 271.1554.

3-(4-(1-Methyl-indol-5-yl)-1,2,3-triazol-1-yl)quinuclidine (QND9): The same method as IND1 was used. 3-Azidoquinuclidine (0.026 g, 0.17 mmol) and 5-ethynyl-methylindole (0.031 g, 0.20 mmol) was reacted for overnight and purified by column chromatography (0-5% CH$_3$OH in CH$_2$Cl$_2$ with 1% Et$_3$N added) followed by washing with diethyl ether with a few drops of CH$_3$OH added to remove traces of the 3-azidoquinuclidine. The product was isolated as a pale yellow powder (34.28%). $^1$H-NMR (300 MHz, DMSO-d$_6$) δ 8.74 (s, 1H), 8.05 (d, J=0.9 Hz, 1H), 7.67 (dd, J=8.5, 1.4 Hz, 1H), 7.52 (d, J=8.5 Hz, 1H), 7.37 (d, J=3.0 Hz, 1H), 6.48 (d, J=2.9 Hz, 1H), 5.22-5.12 (m, 1H), 4.00 (dd, J=13.8, 5.0 Hz, 1H), 3.95-3.84 (m, 1H), 3.81 (s, 3H), 3.47-3.40 (m, 1H), 3.32-3.22 (m, 4H), 2.07-1.98 (m, 2H), 1.82-1.63 (m, 2H); mp=262-264° C.; HRMS calculated ($C_{18}H_{21}N_5$, MH$^+$) 308.1870, found 308.1874.

9-((1-(Quinuclidin-3-yl)-1,2,3-triazol-4-yl)methyl)-purin-6-amine (QND10): The same method as IND1 was used. 3-Azidoquniclidine (0.026 g, 0.17 mmol) was reacted with 9-(propargyl)adenine (0.023 g, 0.13 mmol) for 3 d and purified by column chromatography (0-10% CH$_3$OH in CH$_2$Cl$_2$ with 1% Et$_3$N added) followed by washing with a few drops of CH$_3$OH added in diethyl ether to remove traces of the azide. The product was isolated as a pale yellow solid (46.28%). $^1$H-NMR (500 MHz, DMSO-d$_6$) δ 8.23 (s, 1H), 8.19 (s, 1H), 8.14 (s, 1H), 7.20 (s, 2H), 5.43 (s, 2H), 4.76-4.64 (m, 1H), 3.45-3.34 (m, 2H), 2.97-2.88 (m, 1H), 2.81-2.71 (m, 3H), 2.12-2.06 (m, 1H), 1.72-1.64 (m, 2H), 1.41-1.32 (m, 2H); mp=213-215° C.; HRMS calculated ($C_{15}H_{19}N_9$, MH$^+$) 326.1836, found 326.1842.

Methyl 3-(1-(quinuclidin-3-yl)-1,2,3-triazol-4-yl)-indole-5-carboxylate (QND11): The same method as IND1 was used. 3-Azidoquniclidine (0.0487 g, 0.32 mmol) was reacted with methyl 3-ethynyl-1H-indole-5-carboxylate (0.0575 g, 0.29 mmol) for overnight. After that, the reaction mixture was purified by column chromatography (0-5% Et$_3$N, 5% CH$_3$OH in CH$_2$Cl$_2$) as solvent system to give white solid compound (26.33%). FTIR (ATR) (cm$^{-1}$) 3100, 3023, 2938, 2871, 1710, 1626, 1592, 1444, 1424, 1306, 1236, 1205, 791, 764, 744; $^1$H-NMR (500 MHz, DMSO-d$_6$) δ 8.87 (s, 1H), 8.55 (s, 1H), 7.88 (s, 1H), 7.79 (d, J=8.1 Hz, 1H), 7.52 (d, J=8.4 Hz, 1H), 4.83-4.74 (m, 1H), 3.87 (s, 3H), 3.57-3.40 (m, 2H), 3.06-2.94 (m, 1H), 2.86-2.73 (m, 3H), 2.21 (s, 1H), 1.84-1.66 (m, 2H), 1.55-1.33 (m, 2H); $^{13}$C-NMR (101 MHz, DMSO-$d_6$) δ 167.3, 142.0, 138.8, 124.8, 124.5, 123.2, 122.6, 121.0, 119.6, 111.7, 107.8, 57.3, 51.9, 51.7, 46.7, 46.4, 27.8, 25.4, 19.8; mp>280° C.; HRMS calculated ($C_{19}H_{21}N_5O_2$, MH$^+$) 352.1768, found 352.1763.

3-(4-(Indol-3-yl)-1,2,3-triazol-1-yl)quinuclidine (QND12): The same method as IND1 was used. 3-Azidoquinuclidine (0.1162 g, 0.76 mmol) was reacted with ethyl 3-ethynyl-1H-indole-1-carboxylate (0.2161 g, 0.76 mmol) for overnight. The crude product was evaporated and purified by column chromatography (10% $CH_3OH$ in $CH_2Cl_2$) to give a white solid compound (32.55%). FTIR (ATR) (cm$^{-1}$) 3057, 3007, 2920, 2867, 1623, 1601, 1448, 1220, 1209, 791, 741; $^1$H-NMR (500 MHz, CDCl$_3$) δ 8.23 (d, J=7.4 Hz, 1H), 8.03 (d, J=8.6 Hz, 2H), 7.86 (s, 1H), 7.41-7.35 (m, 1H), 7.35-7.29 (m, 1H), 4.68-4.62 (m, 1H), 4.49 (q, J=7.1 Hz, 2H), 3.78-3.68 (m, 1H), 3.54-3.43 (m, 1H), 3.20-3.10 (m, 1H), 3.00-2.84 (m, 3H), 2.31-2.24 (m, 1H), 1.88-1.63 (m, 3H), 1.52-1.42 (m, 4H); $^{13}$C-NMR (126 MHz, DMSO-$d_6$) δ 150.9, 141.3, 135.8, 128.1, 125.1, 123.5, 122.8, 120.7, 119.4, 115.4, 112.4, 63.5, 58.5, 52.7, 47.4, 47.0, 28.3, 26.1, 20.2, 14.5. After that ethyl 3-(1-(quinuclidin-3-yl)-1H-1,2,3-triazol-4-yl)-1H-indole-1-carboxylate was deprotected by reacting with LiOH (0.0064 g, 0.27 mmol) in THF:$CH_3OH$:$H_2O$ (2:2:1) at room temperature for 3 h. The reaction mixture was added brine solution, extracted with EtOAc, and concentrated under reduced pressure. The crude product was added $CH_3OH$, filtered via buchner funnel, and washed with $CH_2Cl_2$ and $CH_3OH$ to get white solid compound (48.84%). $^1$H-NMR (500 MHz, DMSO-$d_6$) δ 8.51 (s, 1H), 8.08 (d, J=7.9 Hz, 1H), 7.77 (d, J=2.5 Hz, 1H), 7.43 (d, J=8.0 Hz, 1H), 7.18-7.13 (m, 1H), 7.13-7.07 (m, 1H), 4.78-4.72 (m, 1H), 3.54 (dd, J=14.2, 5.3 Hz, 1H), 3.42-3.34 (m, 1H), 3.04-2.96 (m, 1H), 2.83-2.72 (m, 3H), 2.25-2.19 (m, 1H), 1.80-1.67 (m, 2H), 1.52-1.43 (m, 1H), 1.43-1.34 (m, 1H); $^{13}$C-NMR (126 MHz, DMSO-$d_6$) δ 142.4, 136.3, 124.7, 123.0, 121.5, 120.1, 119.4, 119.0, 111.7, 106.4, 57.2, 51.8, 46.7, 46.4, 27.8, 25.4, 19.8; mp=268.5-270° C.; HRMS calculated ($C_{17}H_{19}N_5$, MH$^+$) 294.1713, found 294.1718.

3-(4-chlorophenyl-1,2,3-triazol-1-yl)quinuclidine (QND13): The same method as IND1 was used. 3-Azidoquinuclidine (0.0533 g, 0.35 mmol) in THF, t-BuOH and water (1:1:1) was reacted with 1-chloro-4-ethynylbenzene (0.0548 g, 0.40 mmol) for overnight. The crude product was purified by column chromatography (5% $CH_3OH$ in $CH_2Cl_2$) to give a white solid compound (33.32%). FTIR (ATR) (cm$^{-1}$) 3125, 3053, 2931, 2867, 1547, 1479, 1448, 1232, 1091, 969, 825, 779; $^1$H-NMR (500 MHz, CD$_3$OD) δ 8.47 (s, 1H), 7.87-7.80 (m, 2H), 7.48-7.42 (m, 2H), 4.90-4.85 (m, 1H), 3.74 (dd, J=14.5, 4.1 Hz, 1H), 3.55-3.46 (m, 1H), 3.21-3.10 (m, 1H), 3.00-2.88 (m, 3H), 2.33-2.26 (m, 1H), 1.95-1.86 (m, 2H), 1.69-1.51 (m, 2H); $^{13}$C-NMR (101 MHz, CD$_3$OD) δ 147.7, 135.0, 130.6, 130.1, 128.1, 122.4, 59.4, 52.5, 47.8, 47.5, 29.3, 26.2, 20.6; mp=134.5-135.5° C.; HRMS calculated ($C_{15}H_{17}ClN_4$, MH$^+$) 289.1214, found 289.1214.

Methyl 2-amino-5-(1-(quinuclidin-3-yl)-1H-1,2,3-triazol-4-yl)benzoate (QND15): The same method as IND1 was used. 3-Azidoquinuclidine (0.0530 g, 0.35 mmol) in THF, t-BuOH and water (1:1:1) was reacted with methyl 2-amino-5-ethynylbenzoate (0.0586 g, 0.33 mmol) for overnight. The crude product was purified by column chromatography (10% $CH_3OH$ in $CH_2Cl_2$) to give a white solid compound (33.79%). FTIR (ATR) (cm$^{-1}$) 3445, 3323, 3171, 3129, 2935, 2867, 1692, 1619, 1593, 1483, 1437, 1300, 1235, 1216, 1072, 829, 787; $^1$H-NMR (500 MHz, CD$_3$OD) δ 8.32-8.25 (m, 2H), 7.70 (dd, J=8.7, 2.0 Hz, 1H), 6.83 (d, J=8.6 Hz, 1H), 4.83-4.78 (m, 1H), 3.88 (s, 3H), 3.73 (dd, J=14.6, 4.8 Hz, 1H), 3.51-3.42 (m, 1H), 3.14 (td, J=12.4, 5.0 Hz, 1H), 3.00-2.86 (m, 3H), 2.30-2.25 (m, 1H), 1.92-1.84 (m, 2H), 1.69-1.50 (m, 2H); $^{13}$C-NMR (126 MHz, DMSO-$d_6$) δ 169.7, 152.8, 148.7, 132.6, 129.3, 120.7, 119.1, 118.2, 111.0, 59.2, 52.4, 52.0, 47.8, 47.5, 29.3, 26.2, 20.6; mp=146.5-148.5° C.; HRMS calculated ($C_{17}H_{21}N_5O_2$, MH$^+$) 328.1768, found 328.1765.

2. Activity Testing

Cell lines expressing specific subtypes of receptors and a genetically encoded fluorescence resonance energy transfer (FRET)-based calcium sensor (TN-XXL) were prepared[29]. The human α7-nAChRs and α4β2-nAChRs were expressed in HEKtsA201 cells, whereas hα7/m5HT$_{3A}$ chimeric receptors and mouse 5HT$_{3A}$ receptors were expressed in HEK293 cells. Cells were cultured in DMEM (Corning, Cellgro, Manassas, Va.) supplemented with 10% FBS (Gibco, Life Technologies, Grand Island, N.Y.) and 1% glutamine (Gibco, Life Technologies, Grand Island, N.Y.) and incubated at 37° C. with 10% $CO_2$.

2.1) Intact Cell Binding Assay

Cell based neurotransmitter fluorescent engineered reporters (CNiFERs) expressing $Ca^{2+}$ permeable LGIC receptors were used to determine the $K_d$ values of the compounds. Cells were harvested by centrifugation (Beckman coulter, Brea, Calif.) at 500 rpm for 5 min, and then mixed and incubated on ice for 30 min, after counting, with Wheat Germ Agglutinin SPA beads (20 mg/mL) (Perkin Elmer, Waltham, Mass.) in Hank's Balanced Salt Solution (HBSS) (Gibco, Life Technologies, Grand Island, N.Y.) at the specified concentrations: 1) hα7/m5HT$_{3A}$ chimera-TN-XXL: 200K cells/well, 1 mg/mL SPA beads 2) hα4β2-TN-XXL: 100K cells/well, 0.5 mg/mL SPA beads, and 3) m5HT$_{3A}$-TN-XXL: 100K cells/well, 1 mg/mL SPA beads. The compounds were initially screened at 10 μM final concentration. Nonspecific binding was measured by using 100 μM of MLA (Tocris Bioscience, Bristol, UK) for α7/5HT$_{3A}$ chimeric receptors, 10 μM of varenicline (Tocris Bioscience, Bristol, UK) for α4β2-nAChR, and 300 nM of tropisetron (Tocris Bioscience, Bristol, UK) for 5HT$_{3A}$ receptors. After that, the radioactive ligands were added at 20 nM final concentration of [$^3$H]-(±)-epibatidine for α7/5HT$_{3A}$ chimeric receptors, 5 nM of [$^3$H]-(±)-epibatidine for α4β2-nAChR, and 10 nM of [$^3$H]-granisetron for 5HT$_{3A}$ receptors. The mixtures were measured on the Wallac 1450 MicroBeta® Trilux with 1 h intervals for a total of 15 measurements. Compounds that displaced over 50% of the bound radioligand from the LGIC-CNiFERs were analyzed in separate experiments for $K_d$ values by the Cheng-Prusoff equation using GraphPad Prism. Mean $K_d$ values and standard deviations were calculated from at least 3 independent experiments.

2.2) Functional Assays for Agonists and Antagonists[29]

Agonist and antagonist elicited responses were characterized using the above CNiFER cell expressing Cys-loop ligand-gated ion channel (LGIC) receptors. A fluorometric imaging plate reader system (FlexStation 3; Molecular Devices, Sunnyvale, Calif.) was used to detect FRET responses from HEK cells expressed α7-nAChRs, α4β2-nAChRs, and 5HT$_{3A}$ receptors. A 96-well black, clear-bottom microplate (Greiner bio-one, Germany) was coated with poly-D-lysine (Sigma-Aldrich, St. Louis, Mo.) 50 μL/well for 30 min and washed out with Phosphate-Buffered Saline (PBS) (Corning, Cellgro, Manassas, Va.) before plating the cells. After plating and incubation at 37° C. for 1 day, the media was replaced with 100 μL of artificial cerebrospinal fluid (aCSF: 121 mM NaCl, 5 mM KCl, 26 mM NaHCO₃, 1.2 mM NaH₂PO₄.H₂O, 10 mM glucose, 2.4 mM CaCl₂, 1.3 mM MgSO₄, 5 mM HEPES, pH 7.4) for α4β2 and 5HT$_{3A}$ receptors, whereas 10 μM PNU-120596 (Tocris Bioscience, Bristol, UK) in aCSF with 30 min incubation at 37° C. was used for α7-nAChR. The tested compounds were prepared in aCSF for all receptors except α7-nAChR, where 10 μM PNU-120596, a positive allosteric modulator (PAM) was used. The prepared compounds were added in a separate 96-well polypropylene plate (Costar, Corning, N.Y.). Experiments were conducted at 37° C. using 436-nm excitation. Emitted light was collected at 485 nm and 528 nm. Basal fluorescence was recorded for 30 s, followed by addition of 50 μL of ligand (first addition). Measurements were made at 3.84 s intervals for 2 min to measure the agonistic effect. After that, the agonist compound, which was 100 nM final concentration of (±)-epibatidine (Tocris Bioscience, Bristol, UK) for α7- and α4β2-nAChRs, and 1 μM of 5-hydroxytryptamine (5-HT) (Tocris Bioscience, Bristol, UK) for the 5HT$_{3A}$ receptor were added to evaluate the antagonistic effect of tested compounds. Agonist and antagonist properties were sequentially screened at the final concentration of 13.3 and 10 μM, respectively, which differed from the screening concentration from intact cell binding assay (10 μM). Therefore, some compounds that do not bind to Cys-loop ligand-gated ion channel (LGIC) receptors at screening concentrations still exhibit agonist and antagonist responses in functional screening characterizations. Compounds whose fraction of the maximal response (Δ/Δ$_{max}$) was higher than 0.20 were further evaluated to determine their EC$_{50}$, whereas compounds that inhibit A/Amax more than 0.50 were further characterized to determine the type of antagonism and also calculate the antagonist dissociation constant (K$_A$). The K$_A$ for competitive antagonists and noncompetitive antagonists were calculated from the Schild equations 1 and 2.

$$K_A=[A]/[DR-1] \quad (1)$$

$$K_A=[A]/[(\Delta_{max}/\Delta)-1], \quad (2)$$

where [A] is the concentration of compound, DR (dose-ratio) is the EC$_{50}$ ratio of tested compound over the control compound, which is (±)-epibatidine for α7- and α4β2-nAChR, and 5HT for 5HT$_{3A}$, and Δ/Δ$_{max}$ is the fraction of the maximal response. Average values and standard deviations were calculated from at least 3 independent experiments.

5HT, 5-hydroxytryptamine; AChBP, acetylcholine binding protein; aCSF, artificial cerebrospinal fluid; AD, Alzheimer's disease; BBB, blood brain barrier; CNiFERs; cell based neurotransmitter fluorescent engineered reporters; CuAAC, copper catalyzed azide-alkyne cycloaddition; DMEM, Dulbecco's modified eagle medium; DR, dose-response; ESI, electrospray ionization; FRET, fluorescence resonance energy transfer; FTIR, Fourier transform infrared spectroscopy; HBSS, Hank's balanced salt solution; HRMS, high resolution mass spectrometry, LC-MS, liquid chromatography mass spectrometry, Cys-loop ligand-gated ion channel (LGIC), ligand-gated ion channel; Ls, *Lymnaea stagnalis*; MLA, methyllycaconitine; nAChR, nicotinic acetylcholine receptor; NMR, nuclear magnetic resonance; RBA, radioligand binding assay; SPA, signal proximity assay.

TABLE S1

Physiochemical properties and distance between basic amine and triazole ring of TTIn-1 and IND series. We need a footnote as th how these were determined.

| Compounds | pKa | logP | logD at pH 7.40 | logBB | PSA | H-bond donor | H-bond acceptor | Distance between basic amine and triazole ring (Å) |
|---|---|---|---|---|---|---|---|---|
| TTIn-1 | 9.67 | 2.7 | 0.46 | 0.04 | 49.74 | 1 | 3 | 4.1 |
| IND1 | 9.13 | 3.02 | 1.29 | 0.08 | 49.74 | 1 | 3 | 3.8 |
| IND2 | 9.66 | 3.08 | 0.85 | 0.09 | 49.74 | 1 | 3 | 5.1 |
| IND3 | 9.65 | 3.6 | 1.37 | 0.17 | 49.74 | 1 | 3 | 6.4 |
| IND4 | 6.93 | 1.95 | 1.83 | −0.19 | 58.97 | 1 | 4 | 3.8 |
| IND5 | 7.46 | 2.01 | 1.68 | −0.18 | 58.97 | 1 | 4 | 5.1 |
| IND6 | 7.45 | 2.53 | 2.2 | −0.11 | 58.97 | 1 | 4 | 6.4 |
| IND7 | 9.54 | 3.15 | 1.02 | 0.1 | 49.74 | 1 | 3 | 3.8 |
| IND8 | 9.17 | 2.53 | 0.76 | 0.01 | 49.74 | 1 | 3 | 3.7 |
| IND9 | 9.28 | 1.63 | −0.24 | −0.27 | 61.77 | 2 | 4 | 3.8 |
| IND10 | 9.67 | 2.25 | 0.02 | −0.13 | 58.53 | 2 | 3 | 3.8 |
| IND11 | 8.85 | 2.64 | 1.17 | 0.03 | 49.74 | 1 | 3 | 3.8 |
| IND12 | 8.63 | 2.17 | 0.92 | −0.04 | 49.74 | 1 | 3 | 3.8 |
| IND13 | 9.26 | 2.58 | 0.72 | 0.02 | 49.74 | 1 | 3 | 3.8 |
| IND14 | 9.59 | 3.47 | 1.29 | 0.15 | 49.74 | 1 | 3 | 3.8 |

TABLE S2

Physiochemical properties of PPRD series.

| Compounds | pKa | logP | logD at pH 7.40 | logBB | PSA | H-bond donor | H-bond acceptor | Distance between basic amine and triazole ring (Å) |
|---|---|---|---|---|---|---|---|---|
| PPRD1 | 9.13 | 2.55 | 0.81 | −0.04 | 52.41 | 0 | 5 | 3.8 |
| PPRD2 | 9.14, 3.18 | 2.09 | 0.36 | −0.18 | 59.97 | 1 | 4 | 3.8 |
| PPRD3 | 9.13 | 2.76 | 1.03 | 0.11 | 43.18 | 0 | 4 | 3.8 |
| PPRD4 | 9.13 | 3.44 | 1.7 | 0.32 | 33.95 | 0 | 3 | 3.8 |
| PPRD5 | 9.13 | 2.73 | 1 | −0.17 | 66.81 | 1 | 4 | 3.8 |
| PPRD6 | 9.13 | 3.75 | 2.02 | 0.25 | 43.18 | 0 | 4 | 3.8 |
| PPRD7 | 9.13 | 4.57 | 2.84 | 0.49 | 33.95 | 0 | 3 | 3.8 |
| PPRD8 | 8.9 | 2.62 | 0.89 | −0.12 | 54.18 | 1 | 4 | 3.8 |
| PPRD9 | 9.13 | 3.24 | 1.52 | 0.24 | 38.88 | 0 | 3 | 3.8 |
| PPRD10 | 8.70, 5.11 | 0.41 | −0.91 | −0.96 | 103.57 | 1 | 7 | 3.8 |
| PPRD11 | 9.11 | 3.02 | 1.31 | −0.23 | 76.04 | 1 | 4 | 3.8 |
| PPRD12 | 9.12 | 3.02 | 1.3 | 0.08 | 49.74 | 1 | 3 | 3.8 |
| PPRD13 | 9.13 | 3.53 | 1.8 | 0.34 | 33.95 | 0 | 3 | 3.8 |
| PPRD14 | 9.4 | 3.27 | 1.56 | −0.35 | 80.48 | 1 | 5 | 3.8 |
| PPRD15 | 9.14, 1.07 | 2 75 | 1.01 | −0.4 | 86.27 | 1 | 5 | 3.8 |

TABLE S3

Physiochemical properties of QND series.

| Compounds | pKa | logP | logD at pH 7.40 | logBB | PSA | H-bond donor | H-bond acceptor | Distance between basic amine and triazole ring (Å) |
|---|---|---|---|---|---|---|---|---|
| QND1 | 9.17 | 2.05 | 0.28 | −0.12 | 52.42 | 0 | 5 | 3.7 |
| QND2 | 9.17, 3.12 | 1.6 | −0.17 | −0.25 | 59.97 | 1 | 4 | 3.7 |
| QND3 | 9.17 | 2.27 | 0.5 | 0.03 | 43.18 | 0 | 4 | 3.7 |
| QND4 | 9.17 | 2.94 | 1.17 | 0.25 | 33.95 | 0 | 3 | 3.7 |
| QND5 | 9.17 | 2.24 | 0.47 | −0.24 | 66.81 | 1 | 4 | 3.7 |
| QND6 | 9.17 | 3.26 | 1.49 | 0.18 | 43.18 | 0 | 4 | 3.7 |
| QND7 | 9.17 | 4.08 | 2.31 | 0.42 | 33.95 | 0 | 3 | 3.7 |
| QND8 | 8.93 | 2.13 | 0.36 | −0.19 | 54.18 | 1 | 4 | 3.7 |
| QND9 | 9.17 | 2.75 | 0.98 | 0.17 | 38.88 | 0 | 3 | 3.7 |
| QND10 | 9.09, 5.11 | −0 08 | −1.77 | −1.03 | 103.57 | 1 | 7 | 3.7 |
| QND11 | 9.17 | 2.53 | 0.76 | −0.3 | 76.04 | 1 | 4 | 3.7 |
| QND12 | 9.17 | 2.53 | 0.76 | 0.01 | 49.74 | 1 | 3 | 3.7 |
| QND13 | 9.17 | 3.03 | 1.26 | 0.26 | 33.95 | 0 | 3 | 3.7 |
| QND15 | 9.17, 1.06 | 2 25 | 0.48 | −0.47 | 86.27 | 1 | 5 | 3.7 |

FIG. 8: cα4β2-nAChR antagonist dose-response curves of IND7. FRET ratios were normalized to the maximum response to (±)-epibatidine (greater than 300 nM).

FIG. 9: $5HT_{3A}$ agonist dose-response curves of IND8. FRET ratios were normalized to the maximum response by 10 μM 5-HT.

FIG. 10: $5HT_{3A}$ antagonist dose-response curves. FRET ratios were normalized to the maximum response by 10 μM 5-HT. (A) IND9, (B) IND10 and (C) IND12 are mix-competitive antagonist, whereas (D) IND14 showed competitive antagonism.

FIG. 11: $5HT_{3A}$ receptor antagonist dose-response curves of PPRD series. (A) PPRD8, (C) PPRD12, (D) PPRD14, and (E) PPRD15 are competitive antagonist, and (B) PPRD9 is a mixed (competitive,non-competive) antagonist. FRET ratios were normalized to the maximum response by 10 μM 5-HT.

FIG. 13: α4β2 nAChR antagonist dose-response curves of QND series. (A) QND6, (C) QND9, and (E) QND13 are mix-competitive antagonist, whereas (B) QND8, (D) QND11, and (F) QND15 showed competitive antagonism. FRET ratios were normalized to the maximum response by 316 nM (±)-epibatidine.

FIG. 14: $5HT_{3A}$ receptor agonist characterization of QND series. FRET ratios were normalized to the maximum response by 10 μM 5-hydroxytryptamine (5-HT).

FIG. 15: $5HT_{3A}$ receptor antagonist dose-response curves of QND series. (A) QND4 is mix-competitive antagonist, and (B) QND11 is non-competitive antagonist. FRET ratios were normalized to the maximum response by 10 μM 5-HT.

FIG. 16: α4β2-nAChR antagonist dose-response curves of PPRD series. (A) PPRD9 is mix-competitive antagonist, and (B) PPRD11 is competitive antagonist. FRET ratios were normalized to the maximum response to (±)-epibatidine (approximately 300 nM).

Example 2: Exemplary Compounds IND8 and QND8 are Potent α7-nAChR Agonists

This example demonstrates the effectiveness of exemplary compositions as provided herein as selective α7 nicotinic acetylcholine receptor (nAChR) agonists. This example demonstrates that exemplary compounds IND8 and QND8 are potent α7-nAChR agonists, can reverse amnesia and improve spatial working memory, episodic short-term memory, and reference long-term memory—all behavioral parameters typically impaired in AD. Moreover, they can be used to enhance cognition.

nAChR is a recognized drug target for dementias of aging and for certain developmental disorders. Two selective and potent α7-nAChR agonists, 5-((quinuclid-3-yl)-1H-1,2,3-triazol-4-yl)-1H-indole (IND8) and 3-(4-hydroxyphenyl-1, 2,3-triazol-1-yl) quinuclidine (QND8), were evaluated for the cognitive improvement in both short-term and long-term memory. Three behavioral tests namely: a modified Y-maze, object recognition test (ORT) and water maze were performed in scopolamine-induced amnesic mice. Intraperitoneal injection of these two compounds significantly improved the cognitive impairment in modified Y-maze test (5 μmol/kg for IND8 and 10 μmol/kg for QND8), ORT (10 μmol/kg) and water maze test (25 μmol/kg). For physiologically induced amnesia or natural memory loss in mice, IND8 and QND8 at 10 μmol/kg i.p. were able to enhance memory when evaluated using ORT time delay model. The cognitive enhancement of IND8 and QND8 was mediated through α7-nAChRs as evidenced by the complete abolition of the cognitive enhancement after pretreatment with a selective α7-nAChR antagonist, methyllycaconitine. These data demonstrate that IND8 and QND8 and their congeners are potential candidates for treatment of cognitive disorders and the substituted triazole series warrants further preclinical optimization.

Figure 20:
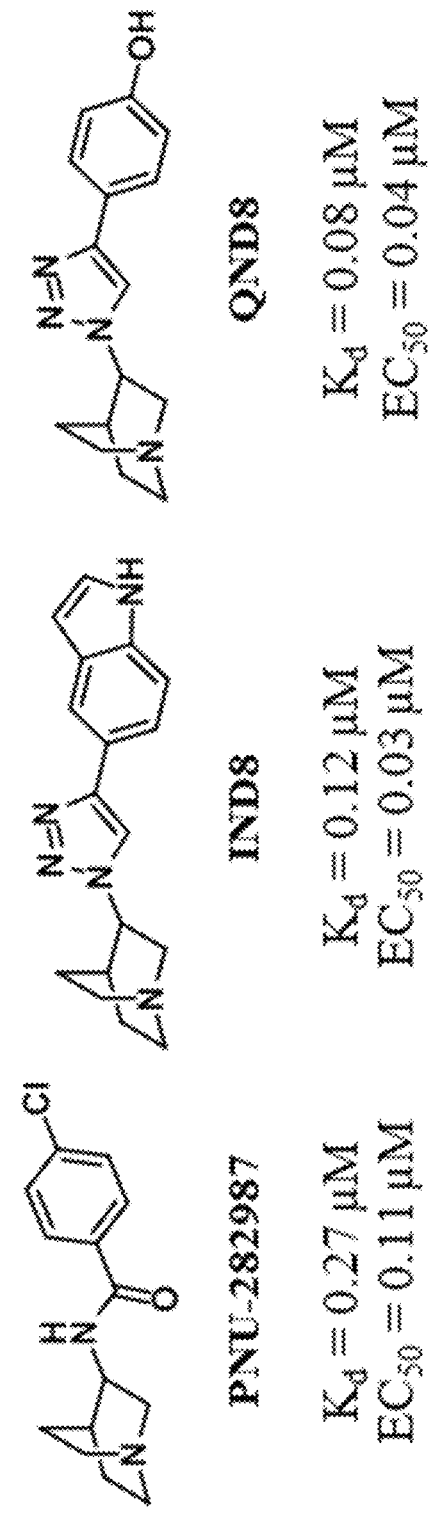
FIG. 20 schematically illustrates structures of the exemplary PNU-282987, IND8 and QND8 compounds as provided herein, evaluated as α7-nAChR agonists with the binding affinity ($K_d$) and agonist potency ($EC_{50}$) to α7-nAChRs, as further described in Example 2, below.

Two promising candidates, IND8 and QND8 selected by optimization of substituted 1,2,3-triazoles as selective and potent α7-nAChR agonists[22] were evaluated for the cognitive improvement and enhancement in amnesic mouse model. The structures, binding, and functional data of IND8, QND8, and PNU-282987, the reference α7-nAChR agonist, are shown in FIG. 20. In this study, three models of behavioral testing i.e. modified Y-maze, object recognition test (ORT), and water maze were performed in mice to evaluate these α7-nAChR agonists on cognitive improvements for both short-term and long-term memory in scopolamine-induced amnesic mouse model. Moreover, the cognitive enhancement in physiological (natural memory loss) amnesia was accessed using ORT time delay model. Functional antagonism was evaluated to verify that cognitive enhancement was mediated through α7-nAChR activation.

FIG. 20 illustrates structures of evaluated α7-nAChR agonists with the binding affinity ($K_d$) and agonist potency ($EC_{50}$) to α7-nAChRs.

Results and Discussion

IND8 and QND8 were tested for the cognitive improvement in pharmacologically-induced amnesia in mice using three behavioral models. Doses of 5-50 μmol/kg are the range of tested dose for IND8 (1.5-14.7 mg/kg) and QND8 (1.4-13.5 mg/kg) which came from the range of doses reported in the behavioral studies of α7-nAChR agonists in animal models[12-18] e.g. EVP-5141 (0.3-3 mg/kg),[18] SEN12333 (1-10 mg/kg),[15] and PNU-282987 (10 and 33 μmol/kg or 3 and 10 mg/kg).[12] However, great variation exists in testing protocols, animal species, and dose regimens emphasizing the need for multiple cognitive improvement studies.

Figure 31A:
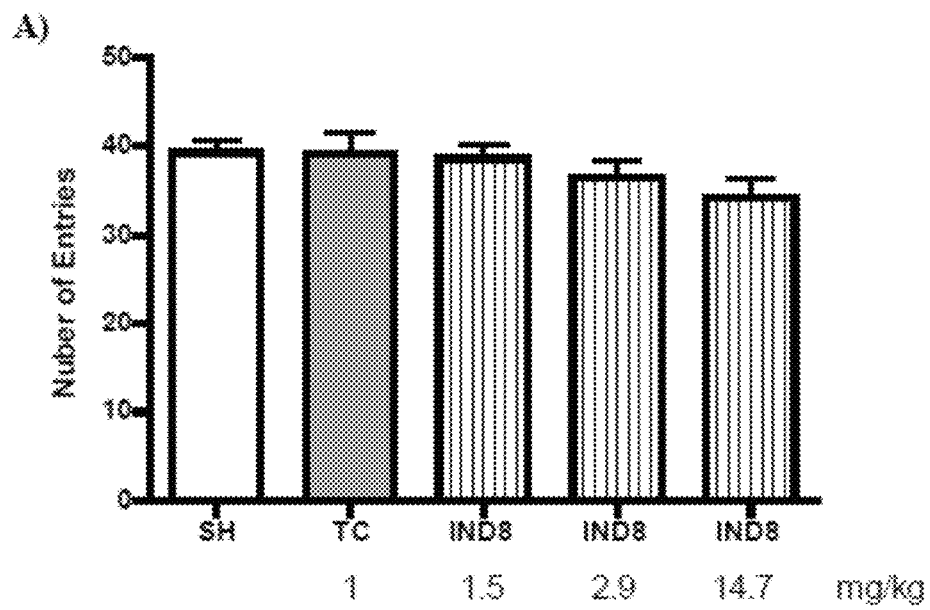
FIG. 31A and FIG. 31B graphically illustrate evaluation of initial screening of IND8 (FIG. 31A) and QND8 (FIG. 31B) to rule out the effect on locomotor activity at all tested doses; IND8 and QND8 were evaluated for their effects on different types of memory impairment by using mouse models for cognitive deficits, as further described in Example 2, below.
Figure 31B:
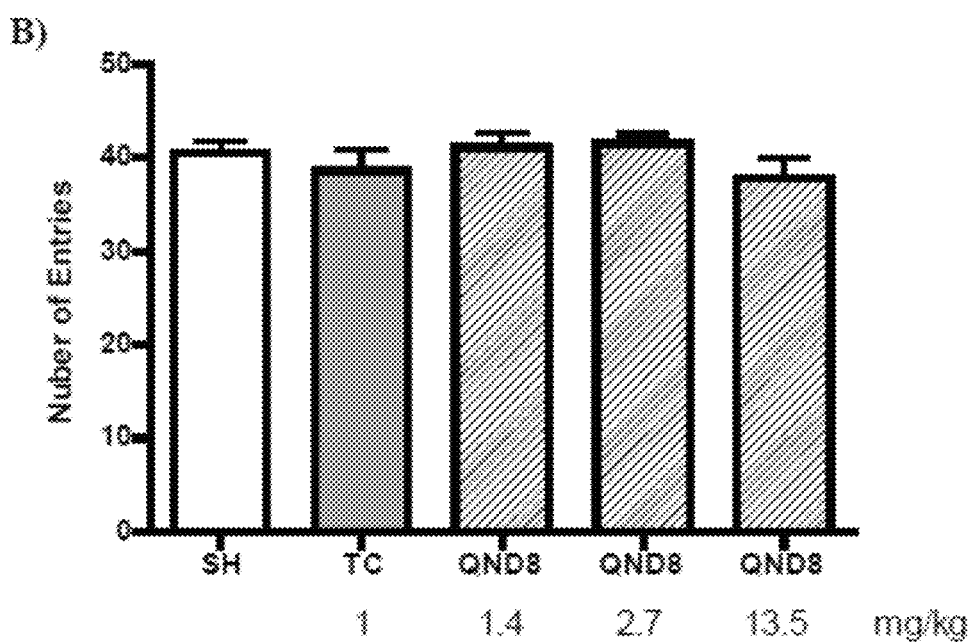

IND8 and QND8 were evaluated for their effects on different types of memory impairment by using mouse models for cognitive deficits. Scopolamine, a muscarinic antagonist, was used to impair cholinergic neurotransmission, shown to elicit deficits in AD patients, and to induce amnesic state in animal and human subjects.[23,24] PNU-282987 was chosen to be a representative of α7-nAChR agonist reference for in vivo profile comparison because its structure contains the same cationic center (quinuclidine ring), and in vitro and in vivo data have been reported.[12-14] PNU-282987, at dose of 10-33 μmol/kg (3-10 mg/kg) was evaluated for cognitive improvement in two study models, the modified Y-maze, and the ORT time delay. These two models reflect different types of memory for deficit analysis: spatial working memory for modified Y-maze and episodic short-term memory for ORT. The experiments were divided into 2 parts, pharmacologically and physiologically induced amnesia. IND8 and QND8 were initially screened to rule out the effect on locomotor activity at all tested doses: neither a reduction nor an increase in locomotor activity was observed (FIG. 31).

1) Effects on Cognition of Pharmacologically Induced Amnesia

The effect of IND8 and QND8 on short-term and long-term memory was evaluated by using modified Y-maze,[25] ORT,[26] and water maze[27] as study models. The data from the scopolamine-treated group (SP) in all experiments indicated that 1 mg/kg of scopolamine can generate amnesia in mice compared with a control group (SH) ($p<0.05$). Because of its historical significance as an AD drug, tacrine (TC), an acetylcholinesterase inhibitor, was used as a positive reference compound. Pretreatment with 1 mg/kg of tacrine 30 min before scopolamine can improve cognitive deficits induced by scopolamine in all test models ($p<0.05$) as shown in FIG. 21.

1.1) Modified Y-Maze[25]

The modified Y-maze test was performed to evaluate spatial working memory. The experiment was divided into 3 sessions; (i) IND8 at 5, 10, and 50 μmol/kg or 1.5, 2.9, and 14.7 mg/kg doses, (ii) QND8 at 5, 10, and 50 μmol/kg or 1.4, 2.7, 13.5 mg/kg doses, and (iii) IND8 and QND8 at dose of 25 μmol/kg or 7.3 and 6.8 mg/kg, respectively and PNU-282987 at 10, 33 μmol/kg or 3, 10 mg/kg doses. An increase of unfamiliar (novelty) arm exploration, when compared with scopolamine-treated group, indicates that these compounds can compensate for cholinergic deficits and improve spatial working memory. The results are shown in FIG. 21. In all 3 sessions, the unfamiliar arm for exploration of the control group was significantly higher than that of scopolamine-treated group, so the mice were in amnesic state. Tacrine, as well as IND8 in all tested doses (1.5-14.7 mg/kg), apparently reversed the cognitive deficit induced by scopolamine as indicated by higher percentage of novelty-arm exploration than that of the amnesic group ($p<0.05$, one-way ANOVA with Fisher's LSD post hoc comparison), whereas QND8 improved the cognitive deficit significantly only at the 2.7 mg/kg dose. Hence, the third testing session was conducted at 25 μmol/kg to confirm the response at high QND8 dose and compare its potency with the reference PNU-282987. The results showed that both IND8 and QND8 significantly improved cognitive deficits in lower doses than that of PNU-282987, seven-fold for IND8 and four-fold for QND8.

Figure 21A:
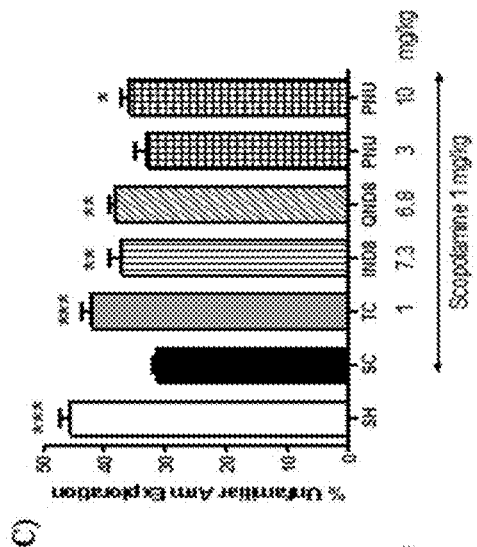
FIG. 21A, FIG. 21B and FIG. 21C graphically illustrates data showing the percentage of unfamiliar arm exploration in modified Y-maze for the exemplary IND8 (FIG. 21A), QND8 (FIG. 21B), and IND8, QND8 and PNU-282987 (FIG. 21C), as further described in Example 2, below.
Figure 21B:
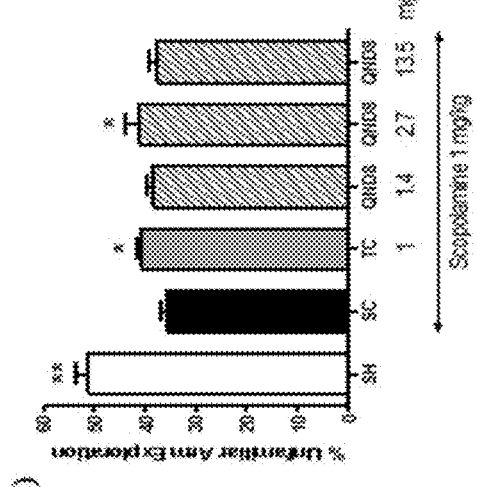
Figure 21C:
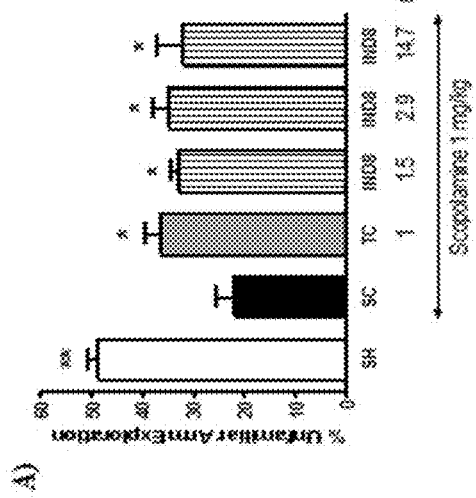

FIG. 21 illustrates the percentage of unfamiliar arm exploration in modified Y-maze of IND8 (FIG. 21A), QND8 (FIG. 21B), and IND8, QND8, PNU-282987 (FIG. 21C). IND8, QND8, PNU-282987, vehicle (15% Tween80, SH) and tacrine (TC) were injected 1 h and scopolamine (SC) 30 min before sample phase, respectively. Each mouse was placed at the end of one arm and allowed to access 2 arms of Y-maze for 5 min in sample phase. After a 30 min period, the mouse was allowed to explore 3 arms for 5 min. The number of entries for each arm was recorded and the percentage of unfamiliar arm exploration was calculated. Data represented in means±standard errors (SE). There was a significant difference of percentage of unfamiliar arm exploration ($F_{5,48}=8.065$, $p<0.001$, n=8-10 mice/group for IND8 (FIG. 21A); $F_{5,52}=10.301$, $p<0.001$, n=9-10 mice/group for QND8 (FIG. 21B); $F_{6,52}=10.930$, $p<0.001$, n=7-10 mice/group for IND8, QND8, PNU-282987 (FIG. 21C)). *$p<0.05$, $p<0.01$, *$p<0.001$ vs scopolamine-treated group (SC), one-way ANOVA with Fisher's LSD post hoc comparison.

Object Recognition Test (ORT)[26]

The effect of compounds to improve episodic (non-spatial) short term memory, that is usually impaired in AD patients, was evaluated by an ORT based on an innate preference of mice to explore a novel object rather than a familiar one. Mice with amnesia induced by scopolamine spent equal time to explore novel and familiar objects ($p>0.05$, paired student's t-test), whereas mice in control group or amnesic mice treated with test compounds exhibited significantly different exploration time between objects (FIG. 22), reflecting a significant improvement from amnesic state ($p<0.05$, paired student's t-test).

Figure 22A:
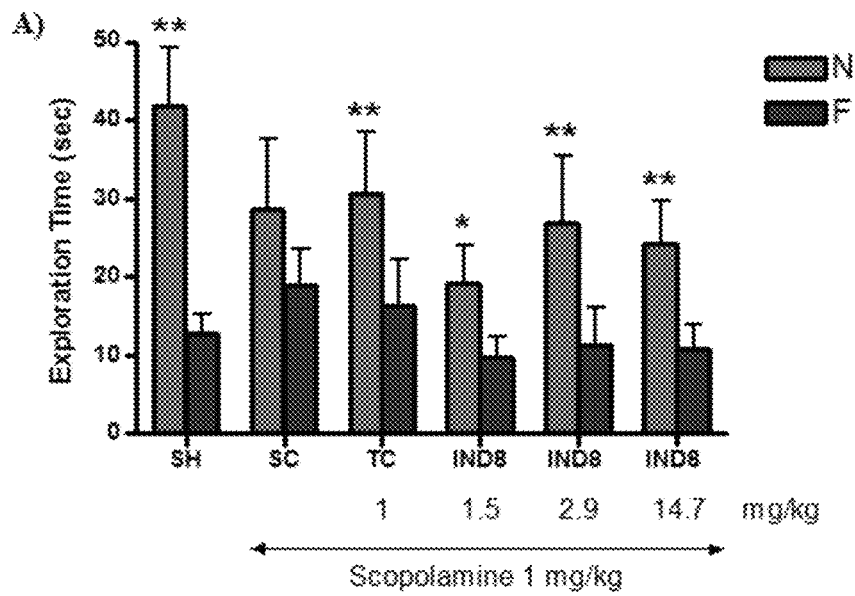
FIG. 22A and FIG. 22B graphically illustrate exploration time to familiar (F) and novel (N) objects after administration of IND8 (FIG. 22A) and QND8 (FIG. 22B) in test phase of an object recognition test (ORT); the exploration time of these objects was recorded, as further described in Example 2, below.
Figure 22B:
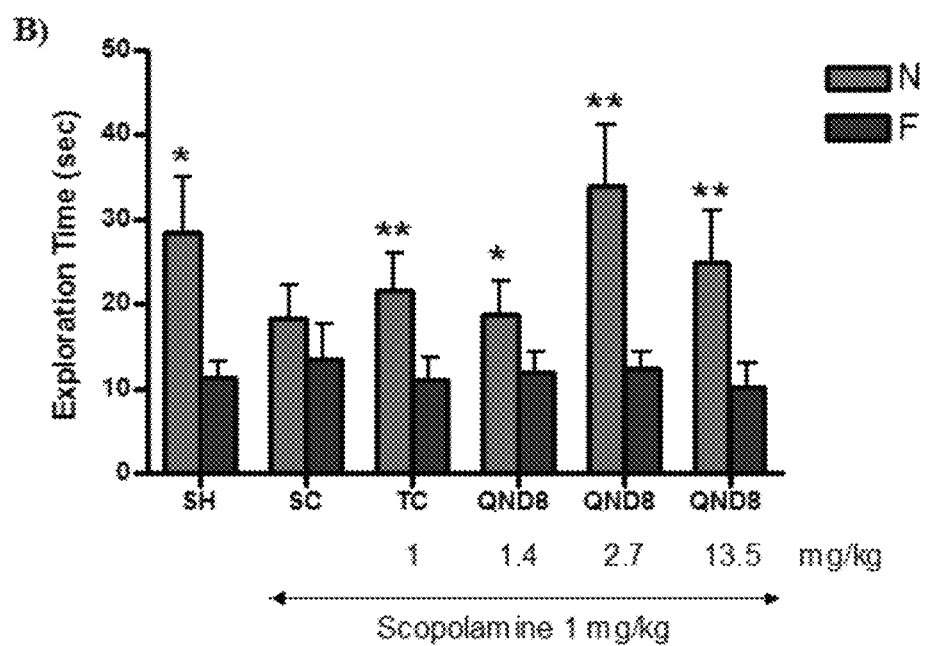

FIG. 22 illustrates exploration time to familiar (F) and novel (N) objects of IND8 (A) and QND8 (B) in test phase of ORT. Each mouse was allowed to explore an open field apparatus for 5 min in a habituation phase. After a 24 h period, IND8, QND8, PNU-282987, vehicle (15% Tween80, SH) and tacrine (TC) were injected 1 h and scopolamine (SC) 30 min before sample phase, respectively. Each mouse explored 2 identical objects in the sample phase for 5 min and then placed in its cage for 10 min before the test phase began. In the 5 min of test phase, one of the objects was changed to a new one. The exploration time of these objects was recorded. Data are presented in means±SE. *$p<0.05$, **$p<0.01$ vs exploration time of familiar object, paired student's t-test.

Figure 23A:
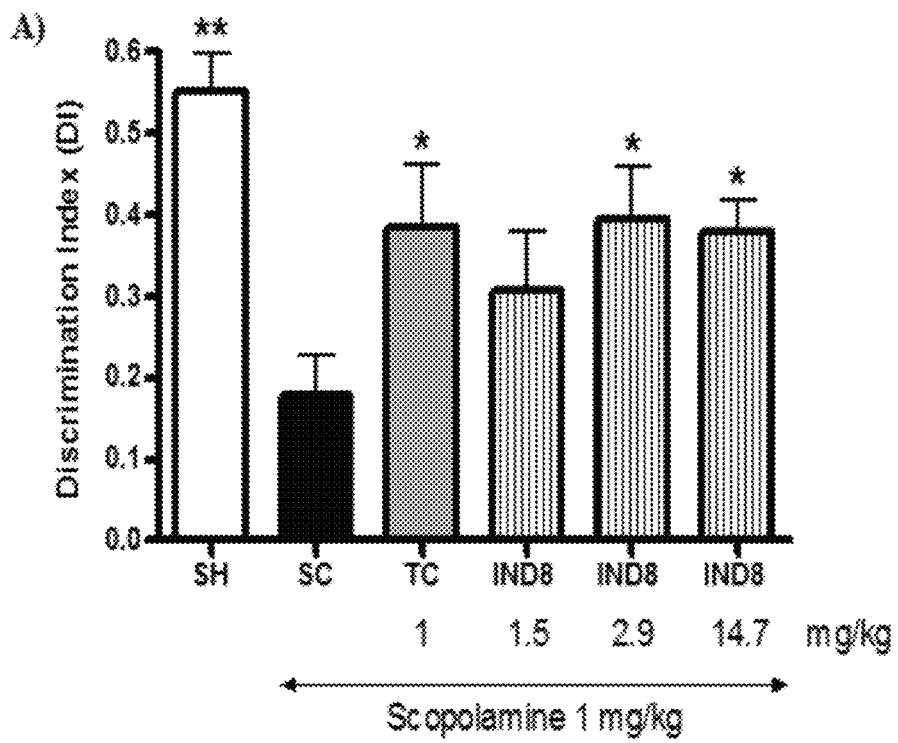
FIG. 23A and FIG. 23B graphically illustrate a discrimination index ($T_N-T_F/T_N+T_F$) of IND8 (FIG. 23A) and QND8 (FIG. 23B) in the test phase of an object recognition test (ORT), as further described in Example 2, below.
Figure 23B:
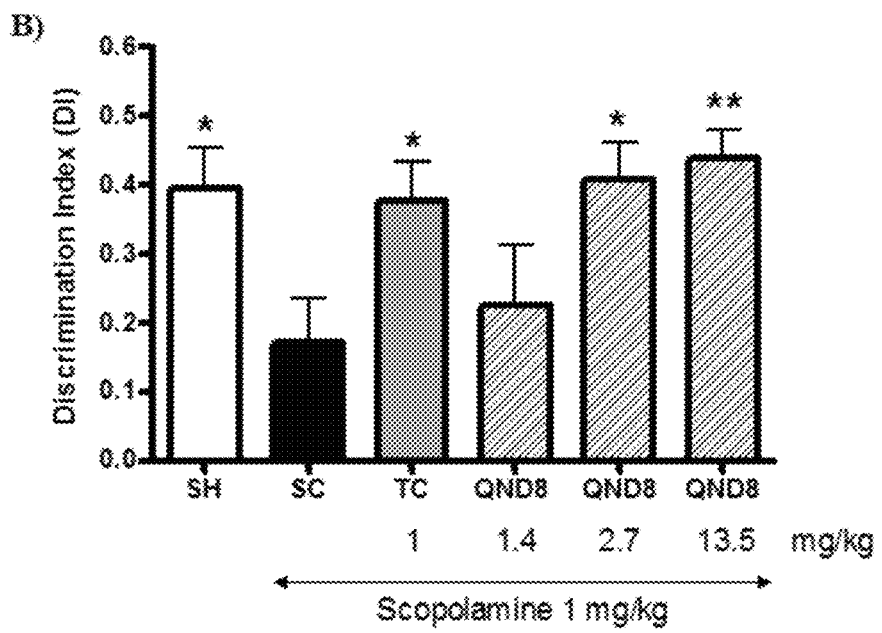

In both data sets, a discrimination index (DI) was calculated and used to evaluate the ability of mice to discriminate between familiar and novel objects. Data are represented in FIG. 23. The higher DI than that of scopolamine-treated group refers to the compensation for cholinergic deficits and improvement in episodic short-term memory. The DI of control group was significantly higher than scopolamine-treated group reflecting their ability to discriminate between familiar and novel objects. Tacrine at 1 mg/kg and IND8 and QND8 at 10 and 50 mol/kg (2.9, 14.7 mg/kg for IND8 and 2.7, 13.5 mg/kg for QND8) significantly improved episodic short-term memory ($p<0.05$) as monitored by the increase of DI compared with amnesic group ($p<0.05$, one-way ANOVA with Fisher's LSD post hoc comparison).

FIG. 23 illustrates discrimination index ($T_N-T_F/T_N+T_F$) of IND8 (A) and QND8 (B) in the test phase of ORT. Data presented as means±SE. There was a significant difference of DI ($F_{5,38}=4.694$; $p=0.002$; n=7-8 mice/group for IND8 group; $F_{5,44}=2.900$; $p=0.024$; n=7-9 mice/group for QND8 group). *$p<0.05$, **$p<0.01$ vs scopolamine-treated group (SC), one-way ANOVA with Fisher's LSD post hoc comparison. SH, control group (vehicle); TC, tacrine group.

1.1) Water Maze[27]

Figure 24A:
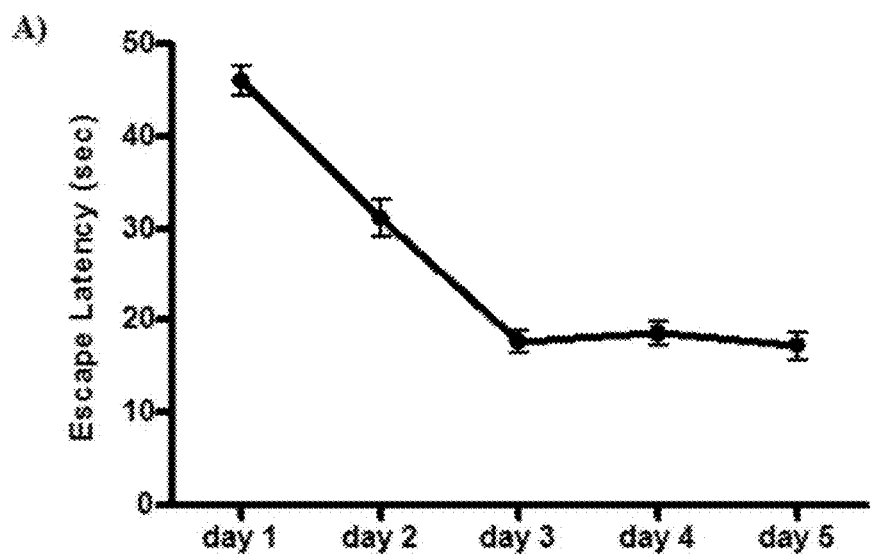
FIG. 24A and FIG. 24B graphically illustrate the results of a water maze test, a model for spatial learning and reference memory related to function in the hippocampus: data shows escape latency time during the training period after administration of IND8 (FIG. 24A) and QND8 (FIG. 24B) groups, as further described in Example 2, below.
Figure 24B:
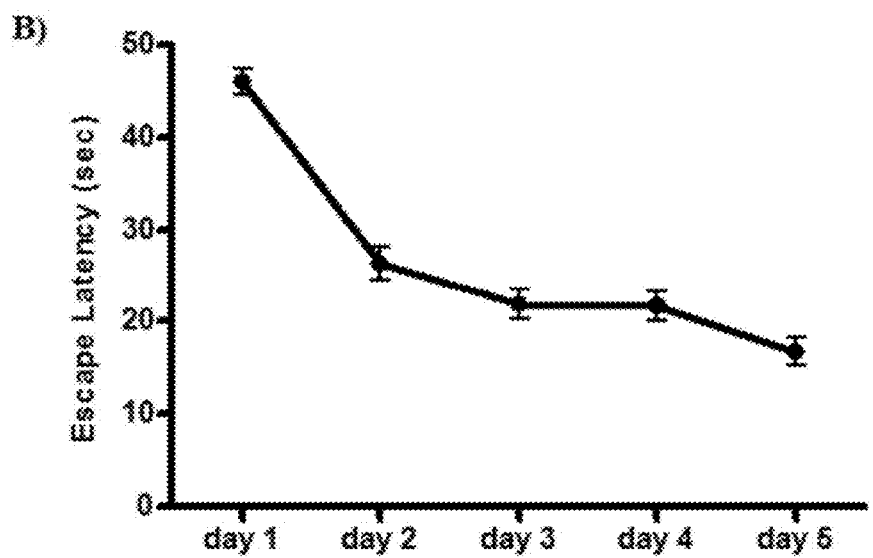

The water maze test, a model for spatial learning and reference memory, related to function in the hippocampus, was also used as a study model in which mice locate a hidden platform after training session. Mice were trained to locate a hidden platform until a steady state measured by a shortened escape latency time was reached. During the training period, the escape latency dramatically decreased during the first three days and reached the steady state around day 5 as shown in FIG. 24, which illustrates the escape latency time during training period of IND8 (A) and QND8 (B) groups.

Figure 25A:
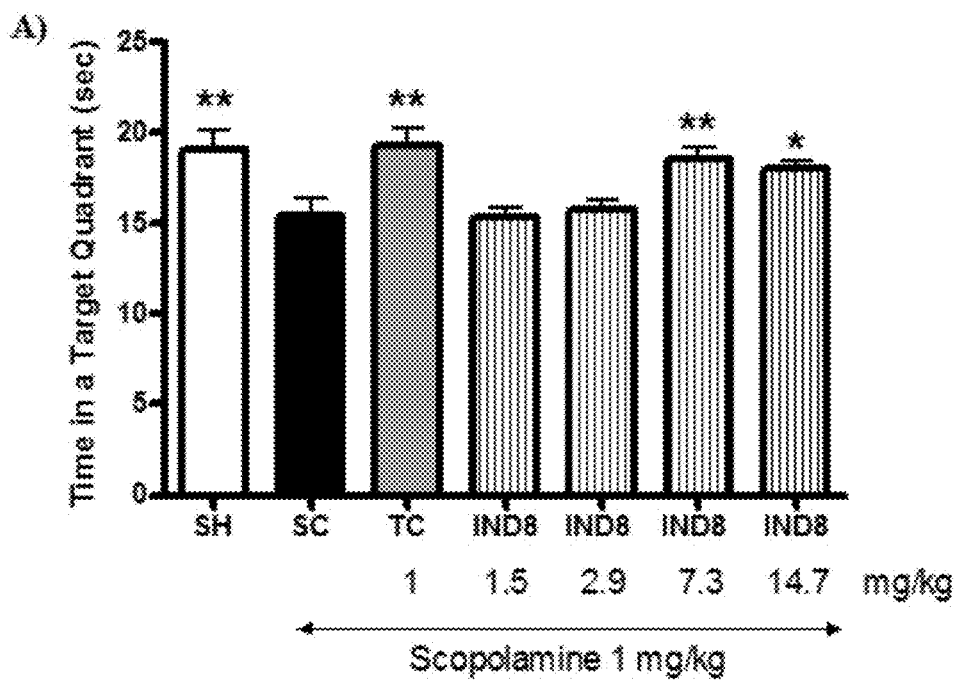
FIG. 25A and FIG. 25B graphically illustrate average swimming time in a target quadrant where the platform had previously been placed was measured in the test day, day 8; treatment group of mice that spent more time in the target quadrant than scopolamine-treated group indicates spatial memory improvement: mice treated with IND8 (FIG. 25A) at 25 and 50 μmol/kg (7.3 and 14.7 mg/kg), and QND8 (FIG. 25B) at 25 μmol/kg (6.8 mg/kg) also significantly spent more time than amnesia group ($p<0.05$) in the target quadrant indicating spatial long-term memory improvement, as further described in Example 2, below.
Figure 25B:
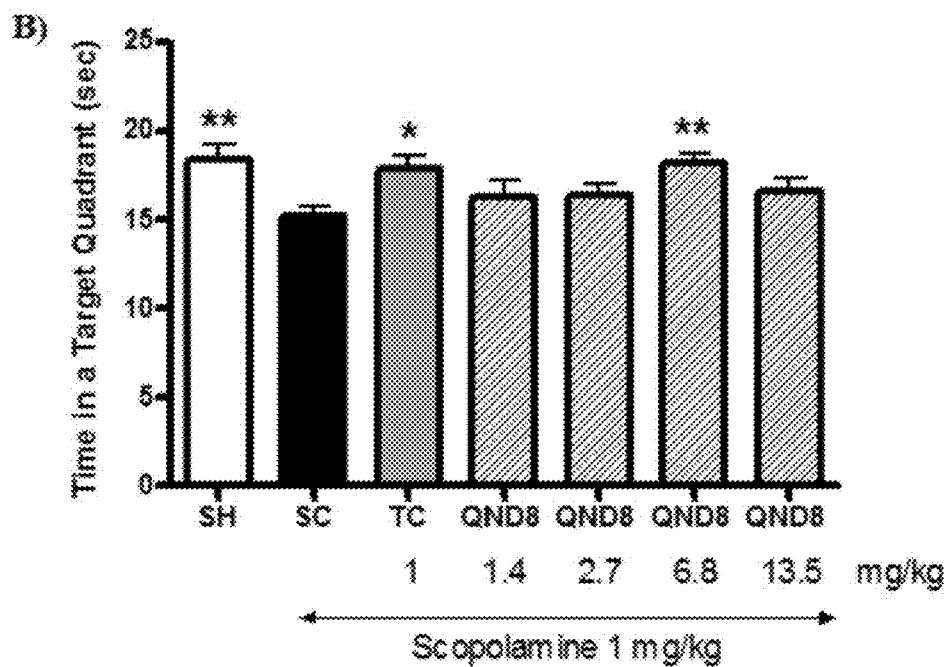

The average swimming time in a target quadrant where the platform had previously been placed was measured in the test day, day 8 (FIG. 25). The treatment group of mice, that spent more time in the target quadrant than scopolamine-treated group, indicates spatial memory improvement. The time spent in the target quadrant of control group was significantly higher than the scopolamine-treated group. Tacrine significantly improved cognitive deficits indicated by spending more time in the target quadrant than amnesia group. Mice treated with IND8 at 25 and 50 µmol/kg (7.3 and 14.7 mg/kg), and QND8 at 25 µmol/kg (6.8 mg/kg) also significantly spent more time than amnesia group ($p<0.05$) in the target quadrant indicating spatial long-term memory improvement.

FIG. 25 illustrates the average swimming time in the target quadrant of water maze test. Data are presented in means±SE. IND8, QND8, PNU-282987, vehicle (15% Tween80, SH) and tacrine (TC) were injected 1 h and scopolamine (SC) 30 min before testing, respectively. There was a significant difference of time spent in the target quadrant ($F_{6,45}=5.079$, $p<0.001$, n=7-10 mice/group for IND8 group; $F_{6,56}=2.465$, $p=0.035$, n=9 mice/group for QND8 group). *$p<0.05$, **$p<0.01$ vs scopolamine-treated group (SC), one-way ANOVA with Fisher's LSD post hoc comparison.

The results from the amnesic mouse model induced by scopolamine indicated that IND8 and QND8, α7-nAChR agonists, clearly improved cognitive learning and memory performance in mice with cholinergic deficits. A possible mechanism is indirect enhancement of acetylcholine release via presynaptic α7-nAChR activation or enhancement of postsynaptic α7-nAChR activation.[12] However, the pattern of IND8 and QND8 behavioral responses is an inverted-U shape, where efficacy decreases in a higher dose range, similar to reports on compounds acting in the cholinergic system.[15,28]

2) Effects on Cognition of Physiologically Induced Amnesia[17]

Figure 26:
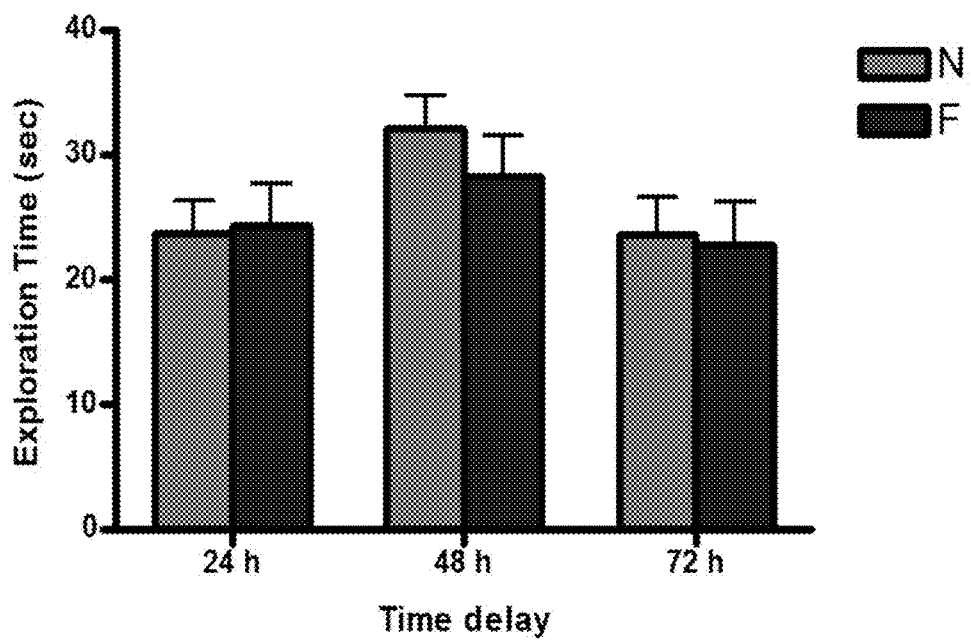
FIG. 26 graphically illustrates exploration time of protocol validation: exploration time of test phase studied with 24, 48, and 72 h time delay between sample and test phase, as further described in Example 2, below.

Both compounds were further evaluated on a physiologic amnesic model by using ORT with 24 h time delay to induce natural memory loss in mice. The appropriate time delay causing amnesia was initially selected by varying delay times (24, 48, and 72 h) between sample and test phase that have identical and different objects, respectively. The exploration time between 2 different objects was not significantly different in the test phase after 24, 48, and 72 h of first exploration ($p>0.05$, paired student's t-test) as shown in FIG. 26. Based on this result, mice did not retain memory of objects after 24 h of first exploration. Therefore, 24 h was used as the time delay between sample and test phase.

FIG. 26 illustrates exploration time of protocol validation. Exploration time of test phase studied with 24, 48, and 72 h time delay between sample and test phase. Each mouse was allowed to explore 2 identical objects in the sample phase for 5 min. After 24 h, 48 h or 72 h time intervals, one of the objects was changed to a different visual shape and color, and the mouse was allowed to explore these objects for 5 min. The exploration time of these objects was recorded. Data presented in mean±SE, n=7-8 mice/group. Paired student's t-test was used to evaluate the different exploration time between novel and familiar objects.

Figure 27:
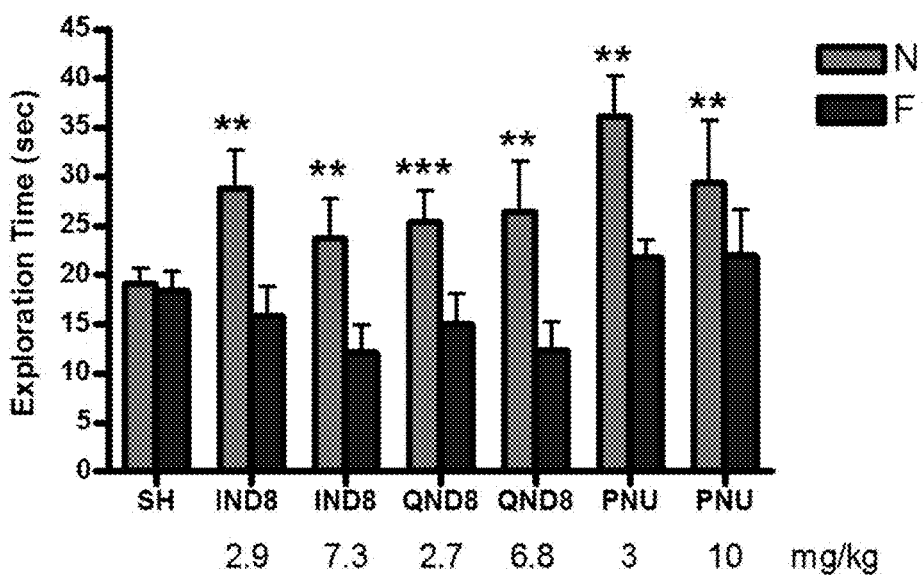
FIG. 27 graphically illustrates exploration time to familiar (F) and novel (N) objects in test phase of ORT following a time delay; each mouse was allowed to explore an open field apparatus for 5 min in a habituation phase one day before a sample phase, as further described in Example 2, below.

FIG. 27 illustrates exploration time to familiar (F) and novel (N) objects in test phase of ORT following a time delay. Each mouse was allowed to explore an open field apparatus for 5 min in a habituation phase one day before a sample phase. In the test day, vehicle (SH) and test compounds IND8, QND8 and PNU were injected 1 h before measurement of exploration time. Each mouse was allowed to explore 2 identical objects in the sample phase for 5 min. On the next day (24 h), one of the objects was changed to a new one and the mouse was allowed to explore these objects for 5 min. The exploration time of these objects was recorded. Data are presented as means±SE, n=6-8 mice/group. $p<0.01$, *$p<0.001$ vs exploration time of familiar object, paired student's t-test.

Figure 28:
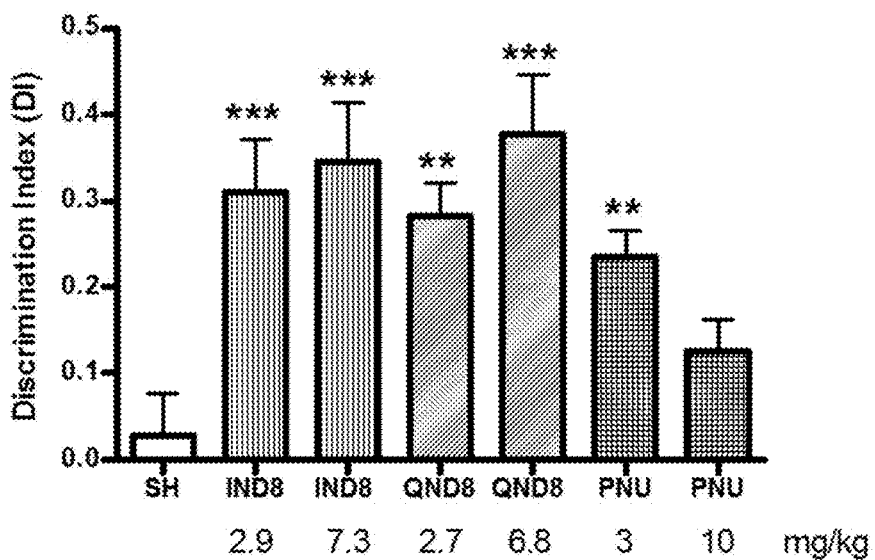
FIG. 28 graphically illustrates exploration times between novel and familiar objects; the DI was calculated and compared with the control group (SH) to evaluate IND8, QND8, and PNU-282987 enhancement of cognitive function, data shown illustrates the discrimination index ($T_N$-$T_F$/$T_N$+$T_F$) of each compound in the test phase of ORT with time delay protocol, as further described in Example 2, below.

The exploration times between novel and familiar objects were significantly different in all treatment groups ($p<0.05$) except for mice in control group that received only vehicle (FIG. 27). The DI was calculated and compared with the control group to evaluate IND8, QND8, and PNU-282987 enhancement of cognitive function. Data are shown in FIG. 28, which illustrates discrimination index ($T_N-T_F/T_N+T_F$) of each compound in the test phase of ORT with time delay protocol. There was a significant difference in DI ($F_{6,43}=6.097$, $p<0.001$, n=6-8 mice/group). * *$p<0.01$, ***$p<0.001$ vs vehicle group (SH), one-way ANOVA with Fisher's LSD post hoc comparison.

Administration of IND8 and QND8 can enhance cognition with the same pattern as PNU-282987 as monitored by the increase of DI. Mice received IND8 and QND8 at 10 and 25 µmol/kg (2.9, 7.3 mg/kg for IND8 and 2.7, 6.8 mg/kg for QND8) and PNU-282987 at 3 mg/kg were able to enhance cognition ($p<0.05$ vs control group, one-way ANOVA with Fisher's LSD post hoc comparison).

3) Mechanism of the Cognitive Enhancement Action

Figure 29:
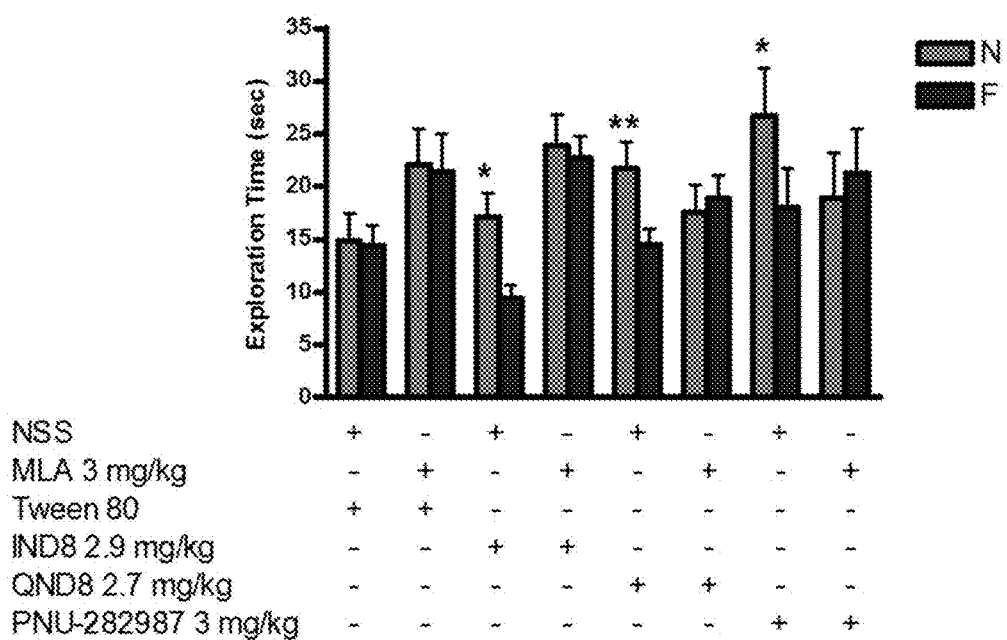
FIG. 29 graphically illustrates exploration time to familiar (F) and novel (N) objects in test phase (B) of ORT after administration of IND8, QND8, and PNU-282987, for establishing that the mechanism of action is mediated through α7-nAChRs, as further described in Example 2, below.

To verify that the mechanism of action of IND8 and QND8 on the cognitive enhancement is mediated through α7-nAChRs, IND8 and QND8 at the minimum effective doses from previous experiments, 10 µmol/kg (2.9 and 2.7 mg/kg, respectively), and PNU-282987 10 µmol/kg (3 mg/kg) were evaluated by using the selective α7-nAChR antagonist. Methyllycaconitine (MLA) was injected to block the α7-nAChR agonist response. The ORT in natural memory loss mice described above was the study model. The exploration time between two objects in both sample and test phase of mice receiving MLA was not significantly different; obtaining the same pattern as vehicle, indicated that MLA itself does not enhance episodic memory as shown in FIG. 29, which illustrates exploration time to familiar (F) and novel (N) objects in test phase (B) of ORT for establishing that the mechanism of action is mediated through α7-nAChRs. Each mouse was allowed to explore an open field apparatus for 5 min in a habituation phase. After 24 hours, MLA (3 mg/kg) was injected 5 min before injection of test compounds. After 1 h of injected test compounds, each mouse explored 2 identical objects in the sample phase for 5 min. On the next day, one of the objects was changed to a new one and the mouse was allowed to explore these objects for 5 min. The exploration time of these objects was recorded. Data are presented in mean±SE, n=7-10 mice/group. $p<0.01$, *$p<0.001$ vs exploration time of familiar object, by the paired student's t-test.

The exploration time between 2 identical objects in sample phase was not significantly different between all treatment groups (data not shown), whereas time to explore between novel and familiar objects was significantly different ($p<0.05$) in all treatment groups, and test compound alone (FIG. 29). As expected, the exploration time between novel and familiar objects of control group and the MLA pretreatment groups were not significantly different. The results indicated that IND8 and QND8 mediated the episodic memory enhancement through α7-nAChRs, since MLA, is a selective α7-nAChR antagonist.

Figure 30:
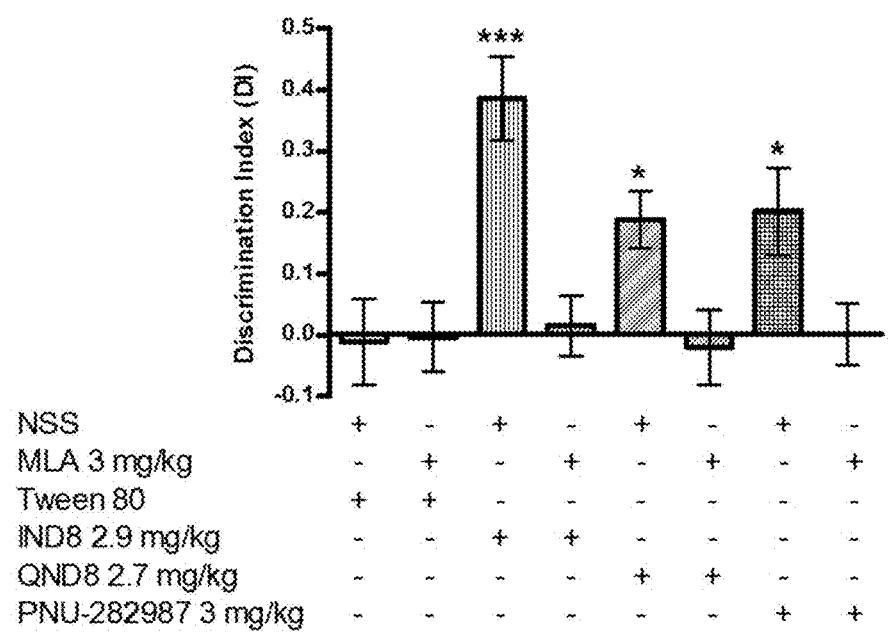
FIG. 30 graphically illustrates discrimination index ($T_N$-$T_F$/$T_N$+$T_F$) of each compound IND8, QND8, and PNU-282987 in the test phase of ORT for proving mechanism of action, as further described in Example 2, below.

FIG. 30 illustrates discrimination index $(T_N-T_F/T_N+T_F)$ of each compound in the test phase of ORT for proving mechanism of action. There was a significant difference of DI ($F_{7,60}$=5.617, p<0.001, n=7-10 mice/group). p<0.01, *p<0.001 vs vehicle group, one-way ANOVA with Fisher's LSD post hoc comparison.

For DI, mice receiving vehicle did not recognize the object that they had explored in the sample phase and MLA alone did not have cognitive enhancement effect; therefore, the DI in both groups was near 0. For IND8, QND8, and PNU-282987, the DI in these 3 groups were significantly higher than that of control group which indicated the memory enhancement in mice (p<0.05 vs control group (SH), one-way ANOVA with Fisher's LSD post hoc comparison) as shown in FIG. 11. This cognitive enhancement was abolished by MLA, where the DI of MLA pretreated group returned to the same value as vehicle or MLA groups. Therefore, the cognitive enhancement of IND8, QND8, and PNU-282987 was mediated through α7-nAChR as seen in the DI difference of with and without MLA.

From in vivo results, IND8 and QND8 (5 and 10 μmol/kg, respectively) have higher potency than PNU-282987 (33 μmol/kg) for the improvement of spatial working memory as observed in scopolamine-induced cognitive deficit mice in modified Y-maze test. The same potency of IND8 and QND8 (10 μmol/kg) to improve episodic short-term memory and reference long-term memory in cognitive deficit mice was observed in ORT and water maze test. Moreover, these α7-nAChR agonists, IND8, QND8, and PNU-282987, are able to enhance cognitive function that was evaluated in ORT with time delay to induce amnesia. The binding and agonist activation data correlate well with the minimum effective doses in vivo as summarized in Table 5.

TABLE 5

In vitro agonist binding properties and in vivo efficacy in ICR amnesia mice.

| Compound | $K_d$ ± SD (μM)* | $EC_{50}$ ± SD (μM)* | Minimum effective dose (μmol/kg) | | | |
|---|---|---|---|---|---|---|
| | | | Modified Y-maze[#] | ORT[#] | Water maze[#] | RT[§] |
| PNU-282987 | 0.27 ± 0.14 | 0.11 ± 0.01 | 33 | n.d. | n.d. | 10 |
| IND8 | 0.12 ± 0.06 | 0.028 ± 0.010 | 5 | 10 | 25 | 10 |
| QND8 | 0.081 ± 0.029 | 0.037 ± 0.009 | 10 | 10 | 25 | 10 |

*$K_d$ and $EC_{50}$ for α7-nAChR agonist from radioligand binding assay and functional assays using cells expressed LGIC receptors.[22]
[#]Pharmacologically (scopolamine) induced amnesia model. n.d., not determined.
[§]Physiologically induced amnesia (memory retention) model In Silico Drug Disposition Predictions.

Drug similarity parameters for human ether-a-go-go related gene (hERG) $K^+$ channels blockade, serum albumin binding, permeability properties, and cytochromes P450 inhibition of IND8, QND8, and PNU-282987, α7-nAChR agonists were predicted in silico by QikProp version 4.1[29] and WhichCYP version 1.2.[30] The in silico prediction points out that these compounds have properties that likely enable them to be absorbed orally, pass the blood-brain barrier, and are likely not to be rapidly metabolized. The predicted values of all compounds and the recommended range of drug-similarity are shown in (Table 6, below). The predicted values of all permeation parameters i.e. brain/blood partition coefficient, Caco-2 cell permeability, and cell permeation MDCK values are parallel to their physiochemical properties and $pK_a$ values. IND8 and QND8 that have diminished unprotonated species based on their $pK_a$ values of 9.17 and 8.93, respectively, they still have moderate intestinal (P Caco-2) and BBB permeability (P MDCK and log BB) when compared to PNU-282987 with its lower $pK_a$ value of 7.86. IND8 and QND8 may inhibit CYP450 isoform 2D6, whereas PNU-282987 probably inhibits two isoforms, CYP2D6 and CYP2C19. IND8 has enhanced likelihood to bind to plasma protein and block hERG $K^+$ channels compared to PNU-282987 and QND8. As PNU-282987 showed 57% inhibition of hERG at 20 μM in a patch clamp hERG $K^+$ channel assay,[31] these two optimized lead compounds should be evaluated in vitro for ion channel blockade together with other preclinical assays, such as CYP inhibition, multi-drug resistant (MDR), and P-glycoprotein (PgP) assays.

TABLE 6

Predicted drug-likeness properties of IND8, QND8, and PNU-282987*

| Properties | Parameter | IND8 | QND8 | PNU-282987 | Recommended range |
|---|---|---|---|---|---|
| Human serum protein binding | logKhas | 0.346 | 0.002 | −0.003 | −1.5-1.5 |
| Brain/blood partition coefficient | logBB | 0.198 | −0.075 | 0.678 | −3.0-1.2 |
| Caco-2 cell permeability | P Caco-2 | 389.58 | 218.23 | 1068.749 | <25 poor, >500 great |
| Cell permeability | P MDCK | 197.57 | 105.60 | 1448.244 | <25 poor, >500 great |
| CYP inhibition | CYP isoform | 2D6 | 2D6 | 2D6, 2C19 | |
| $K^+$ channels blockage | logHERG | −5.717 | −5.178 | −5.096 | >−5 |

*In silico prediction by QikProp version 4.1 and WhichCYP version 1.2: logKhas, human serum protein binding; logHERG, $logIC_{50}$ for HERG $K^+$ channels blockage; logBB, brain/blood partition coefficient; P Caco-2, Caco-2 cell permeability in nm/sec; P MDCK, MDCK cell permeability in nm/sec; CYP isoform, cytochromes P450 isoform inhibition.

Taken in vitro and in vivo results together, IND8 and QND8 have higher potencies than PNU-282987, even though the drug-disposition data predicted in silico suggested the slower brain penetration of IND8 and QND8 than that of PNU-282987 due to lower P MDCK and log BB and higher $pK_a$ values. The reason is that the protonated quinuclidine is the active species forming a hydrogen bond donor with the backbone carbonyl oxygen of Trp 149 (α7 numbering) in the α7-nAChR.

Conclusions

The exemplary compounds as provided herein IND8 and QND8, are novel potent α7-nAChR agonists, derived and refined from in situ click-chemistry synthetic leads, can reverse amnesia and improve spatial working memory, episodic short-term memory, and reference long-term memory—all behavioral parameters typically impaired in AD. Moreover, they can be used to enhance cognition. Based on correlations between occupation and activation of α7-nAChRs in intact cells and antagonism of the behavioral response by MLA, this enhancement is mediated through α7-nAChRs. The physical characteristics of the substituted triazoles bode well for crossing the blood-brain barrier and being retained in the CNS. Hence, these findings support the utility of IND8 and QND8 and other substituted 1,2,3 triazole analogues as preclinical candidates in treatment of cognitive disorders.

Materials and Methods

1) In Vivo Assay

Animal Model

Male ICR mice (6-weeks of age) were housed in 5 per cage with free access to food and tap water under 12 h light and dark cycle (light on 6:00 to 18:00) in a temperature and humidity controlled room. They were acclimated in a laboratory at least 7 days prior to starting experiments. The experimental protocols were approved by the Animal Care and Use Committee of KhonKaen University, Thailand.

Compound Preparation and Administration

Tacrine hydrochloride (Sigma-Aldrich, St. Louis, Mo.), PNU-282987 hydrochloride (Alamone, Jerusalem, Israel) and test compounds were prepared as suspensions by using 15% tween 80 in distilled water as a vehicle, whereas scopolamine hydrochloride (Sigma-Aldrich, St. Louis, Mo.) and methyllycaconitine citrate (MLA) (Abcam, Cambridge, England) were prepared as a solution by dissolving with 0.9% normal saline solution (NSS). All compounds were administered by intraperitoneal (i.p.) injection in the amount of 5 mL/kg. Test compounds were injected 1 h and scopolamine was administered 30 min before the experiments, whereas MLA was injected 5 min before the test compounds.

Determination of scopolamine-induced cognitive deficit improvement Amnesia was induced pharmacologically in mice via scopolamine injection (single dose) for 30 min prior to start the experiments. They were divided into vehicle group: receiving 15% tween 80 and 0.9% NSS, amnesia group: receiving scopolamine 1 mg/kg, standard positive control group receiving tacrine 1 mg/kg, and test group: receiving IND8, QND8 at dose 5, 10, 25, 50 μmol/kg, or PNU-282987 3, 10 mg/kg, single dose. All mice were acclimated in an experimental room at least 30 min before the experiments.

Locomotor Activity Test

A black polyvinyl chloride Y-maze, which was 40 cm long, 3 cm wide at the bottom and 10 cm wide at the top, and 12 cm high in each arm, was used to study the effect of synthesized compounds on locomotor activity. Each mouse was placed at the end of one arm and was allowed to move freely in Y-maze for 8 min after 1 h injection of vehicle or test compounds. The number of entries to all arms was recorded visually if mice accessed into each arm at least 10 cm from the middle of the maze.

Modified Y-Maze Test[25]

The maze in this experiment is the same apparatus using in locomotor activity test except there is the black partition to close one of three arms. The mice were randomly separated into different treatment groups. They were injected with test compounds and scopolamine at 1 h and 30 min, respectively, before the sample phase. In this phase which one arm of Y-maze was closed by the black partition, each mouse was placed at the end of one arm and allowed to move through 2 arms for 5 min to get familiar with the two opened arms. After 30 min of resting, all arms were opened and the mouse was allowed to move freely through all 3 arms. The maze area and the partition were cleaned with 70% ethanol between each experiment to remove olfactory cues. The number of entries in each arm was counted visually if mice accessed into each arm at least 10 cm. The percentage of unfamiliar arm exploration was calculated as following equation:

$$\text{Percentage of unfamiliar arm exploration} = \frac{\text{number of unfamiliar arm}}{\text{number of all arms entry}} \times 100$$

-Novel object recognition test $(ORT)^{26}$

The apparatus was made of black polyvinyl chloride (52×52×40 cm). The objects used in this experiment had different visual shapes and colors to be discriminated. They were placed 10 cm from the side wall in the balanced manner. The box area and objects were cleaned with 70% ethanol between each experiment to remove odor cues.

The mice were randomly divided into different treatment groups. They were allowed to freely explore the open field apparatus for 5 min for habituation in the day prior to the experiments to get familiar with the apparatus. On the experimental day, test compounds injected 1 h, whereas scopolamine administered 30 min before the sample phase (acquisition trial). The mice were placed in the apparatus to explore 2 identical objects. After 10 min of acclimation in their cages, one object was changed to a new one, and mice were allowed to explore these objects for 5 min in the test phase (retention trial). The exploration time of each object was recorded if the nose of mice approached the objects within 3 cm or touched the objects. The discrimination index (DI) was calculated by using $(T_N-T_F)/(T_N+T_F)$; $T_N$ and $T_F$ represented exploration time of new and familiar objects, respectively.

Water Maze[27]

A black circular tank (diameter 70 cm; height 28 cm) was divided into 4 quadrants with a removable escape platform (6×7.5×14 cm) centered in a target quadrant. The tank was filled with water to 15 cm height and the platform was located 1 cm below the water surface.

Mice were trained from 5-7 days to get the steady state of escape latency. During day 1 to 5, each mouse was trained to swim from each quadrant with 1 min maximum time and allowed to stay on the platform for 10 sec. The mouse is placed on the platform for 10 s if it cannot find the hidden platform within 1 min. The escape latency time from each quadrant was measured. At the end of training session, mice that cannot locate the platform and do not show the learning ability measured by the decrease of escape latency time were excluded. The probe test began when the escape latency time reached the steady state. The platform was removed and time spent in the target quadrant was measured. On the next day, all conditions were the same as probe test, but the platform was brought back to remind the mice of the target quadrant location. All mice were injected with test compounds 1 h and scopolamine 30 min before testing. The swimming time in the target quadrant was measured.

Determination of Cognitive Enhancement Through α7-nAChRs[17]

The apparatus used in this experiment was the same as ORT test. This experiment was divided into 2 parts directed to dose finding and establishing mechanism of action. The mice were physiologically induced amnesia (natural temporal memory loss) with 24 h time delay protocol.

For dose finding protocol, the mice were randomly divided into different treatment groups, a control group receiving a vehicle and tested groups receiving PNU-282987 at 3, 10 mg/kg, and IND8, QND8 for 10, 25 μmol/kg, single dose. They were allowed to freely explore the open field apparatus for 5 min for habituation in a day before the experiment (day 1). On the test day (day 2), the test compound was injected 1 h before the sample phase. In this phase, mice were placed in the apparatus to explore two identical objects. On the next day (day 3), one object was changed to a new one and mice were allowed to explore these objects for 5 min in the test phase. For proving cognitive enhancement mediated through α7-nAChRs, the protocol was the same as mentioned above except MLA (3 mg/kg), selective α7-nAChR antagonist, was injected 5 min before test compounds in the sample phase (day 2) to block the cognitive enhancement effect from test compounds. The dose of test compounds is selected from the effective dose from the former experiment. The exploration time of each object was recorded if the nose of mouse came within 3 cm or touched the objects. The discrimination index (DI) was calculated by using $(T_N-T_F)/(T_N+T_F)$; $T_N$ and $T_F$ represented exploration time of new and familiar objects, respectively.

Statistics

All results were represented as the mean±standard error (SE) for each data group. The statistics was analyzed by using SigmaStat32. Differences of p<0.05 were considered significant.

The different results of number of entries for locomotor activity testing between test groups and vehicle group were analyzed with a one-way ANOVA, followed by Fisher's least significant difference (LSD) post hoc comparison.

For determination of scopolamine-induced cognitive deficit improvement in modified Y-maze, ORT, and water maze, the results between test groups and amnesia group were analyzed with the one-way ANOVA, followed by Fisher's LSD post hoc comparison except the exploration time between sample and test phase for ORT was analyzed by paired student's t-test.

For determination of cognitive enhancement through α7-nAChRs, one-way ANOVA, followed by Fisher's LSD post hoc comparison was used to compare the DI between test and vehicle groups in dose finding protocol and compared between with and without MLA injection in proving the mechanism of action protocol. The exploration time between sample and test phase was analyzed by paired student's t-test.

2) In Silico Prediction

Structures of IND8 and QND8 were prepared in neutralized form and generated all stereoisomers by LigPrep version 3.1.[32] The physiochemical and pharmaceutical properties of prepared ligands were predicted by QikPrep version 4.1.[29]

TABLE S1

Binding affinity, measured as $K_d$, and functional properties of test compounds with cell-based assays.

| Compound | $K_d$ ± SD | | $EC_{50}$ ± SD | | $K_A$ ± SD | |
|---|---|---|---|---|---|---|
| | α4β2 | 5HT$_{3A}$ | α4β2 | 5HT$_{3A}$ | α4β2 | 5HT$_{3A}$ |
| PNU-282987 | >10 | >10 | >10 | — | >10 | 1.2 ± 0.3[C] |
| IND8 | 0.75 ± 0.20 | 0.052 ± 0.008 | >10 | 0.21 ± 0.08* | >10 | — |
| QND8 | >10 | 0.54 ± 0.05 | — | 0.90 ± 0.09* | 6.2 ± 1.7[C] | — |

The competitive binding assays were performed by scintillation proximity assay (SPA) and functional properties characterization was performed by fluorescence resonance energy transfer (FRET) assay. All values are reported as mean $K_d$±SD (μM) for binding assay and $EC_{50}$±SD or $K_A$±SD for agonist or antagonist (μM), respectively of at least three independent experiments, with each experiment containing at least duplicate samples. *partial agonist; [C]competitive antagonist.

FIG. S1. Locomotor activity testing of IND8 (A) and QND8 (B). Mice were injected vehicle or test compounds 1 h before moving freely in Y-maze for 8 min. The number of entries into 3 arms was recorded. The one-way ANOVA was used to evaluate the different result between test and vehicle groups. There was no significant difference for IND8 ($F_{4,40}$=1.327, p=0.277, n=8-10 mice/group) and also QND8 ($F_{4,45}$=0.870, p=0.489, n=10 mice/group) compared to vehicle group.

REFERENCES

References—Example 1

1. Cummings, J. L., Alzheimer's disease. N Engl J Med 2004, 351 (1), 56-67.
2. Brookmeyer, R.; Johnson, E.; Ziegler-Graham, K.; Arrighi, H. M., Forecasting the global burden of Alzheimer's disease. Alzheimers Dement 2007, 3 (3), 186-91.
3. Huang, Y.; Mucke, L., Alzheimer mechanisms and therapeutic strategies. Cell 2012, 148 (6), 1204-22.
4. Holtzman, D. M.; Morris, J. C.; Goate, A. M., Alzheimer's disease: the challenge of the second century. Sci Transl Med 2011, 3 (77), 77sr1.
5. Lane, R. F.; Shineman, D. W.; Steele, J. W.; Lee, L. B.; Fillit, H. M., Beyond amyloid: the future of therapeutics for Alzheimer's disease. Adv Pharmacol 2012, 64, 213-71.
6. Querfurth, H. W.; LaFerla, F. M., Alzheimer's disease. N Engl J Med 2010, 362 (4), 329-44.
7. Auld, D. S.; Kornecook, T. J.; Bastianetto, S.; Quirion, R., Alzheimer's disease and the basal forebrain cholinergic system: relations to beta-amyloid peptides, cognition, and treatment strategies. Prog Neurobiol 2002, 68 (3), 209-45.
8. Cummings, J. L.; Morstorf, T.; Zhong, K., Alzheimer's disease drug-development pipeline: few candidates, frequent failures. Alzheimers Res Ther 2014, 6 (4), 37.
9. Jensen, A. A.; Frolund, B.; Liljefors, T.; Krogsgaard-Larsen, P., Neuronal nicotinic acetylcholine receptors:

structural revelations, target identifications, and therapeutic inspirations. J Med Chem 2005, 48 (15), 4705-45.
10. Gotti, C.; Clementi, F., Neuronal nicotinic receptors: from structure to pathology. Prog. Neurobiol. 2004, 74 (6), 363-96.
11. Gaimarri, A.; Moretti, M.; Riganti, L.; Zanardi, A.; Clementi, F.; Gotti, C., Regulation of neuronal nicotinic receptor traffic and expression. Brain Res Rev 2007, 55 (1), 134-43.
12. Lippiello, P.; Bencherif, M.; Hauser, T.; Jordan, K.; Letchworth, S.; Mazurov, A., Nicotinic receptors as targets for therapeutic discovery. Expert Opin Drug Discov 2007, 2 (9), 1185-1203.
13. Taly, A.; Corringer, P. J.; Guedin, D.; Lestage, P.; Changeux, J. P., Nicotinic receptors: allosteric transitions and therapeutic targets in the nervous system. Nat Rev Drug Discov 2009, 8 (9), 733-50.
14. Briggs, C. A.; Anderson, D. J.; Brioni, J. D.; Buccafusco, J. J.; Buckley, M. J.; Campbell, J. E.; Decker, M. W.; Donnelly-Roberts, D.; Elliott, R. L.; Gopalakrishnan, M.; Holladay, M. W.; Hui, Y. H.; Jackson, W. J.; Kim, D. J.; Marsh, K. C.; O'Neill, A.; Prendergast, M. A.; Ryther, K. B.; Sullivan, J. P.; Arneric, S. P., Functional characterization of the novel neuronal nicotinic acetylcholine receptor ligand GTS-21 in vitro and in vivo. Pharmacol Biochem Behav 1997, 57 (1-2), 231-41.
15. Hibbs, R. E.; Sulzenbacher, G.; Shi, J.; Talley, T. T.; Conrod, S.; Kem, W. R.; Taylor, P.; Marchot, P.; Bourne, Y., Structural determinants for interaction of partial agonists with acetylcholine binding protein and neuronal alpha7 nicotinic acetylcholine receptor. EMBO J 2009, 28 (19), 3040-51.
16. Wallace, T. L.; Callahan, P. M.; Tehim, A.; Bertrand, D.; Tombaugh, G.; Wang, S.; Xie, W.; Rowe, W. B.; Ong, V.; Graham, E.; Terry, A. V., Jr.; Rodefer, J. S.; Herbert, B.; Murray, M.; Porter, R.; Santarelli, L.; Lowe, D. A., RG3487, a novel nicotinic alpha7 receptor partial agonist, improves cognition and sensorimotor gating in rodents. J Pharmacol Exp Ther 2011, 336 (1), 242-53.
17. Toyohara, J.; Hashimoto, K., alpha7 Nicotinic Receptor Agonists: Potential Therapeutic Drugs for Treatment of Cognitive Impairments in Schizophrenia and Alzheimer's Disease. Open Med Chem J 2010, 4, 37-56.
18. Mazurov, A.; Hauser, T.; Miller, C. H., Selective alpha7 nicotinic acetylcholine receptor ligands. Curr Med Chem 2006, 13 (13), 1567-84.
19. Radek, R. J.; Robb, H. M.; Stevens, K. E.; Gopalakrishnan, M.; Bitner, R. S., Effects of the novel alpha7 nicotinic acetylcholine receptor agonist ABT-107 on sensory gating in DBA/2 mice: pharmacodynamic characterization. J Pharmacol Exp Ther 2012, 343 (3), 736-45.
20. Ghiron, C.; Haydar, S. N.; Aschmies, S.; Bothmann, H.; Castaldo, C.; Cocconcelli, G.; Comery, T. A.; Di, L.; Dunlop, J.; Lock, T.; Kramer, A.; Kowal, D.; Jow, F.; Grauer, S.; Harrison, B.; La Rosa, S.; Maccari, L.; Marquis, K. L.; Micco, I.; Nencini, A.; Quinn, J.; Robichaud, A. J.; Roncarati, R.; Scali, C.; Terstappen, G. C.; Turlizzi, E.; Valacchi, M.; Varrone, M.; Zanaletti, R.; Zanelli, U., Novel alpha-7 nicotinic acetylcholine receptor agonists containing a urea moiety: identification and characterization of the potent, selective, and orally efficacious agonist 1-[6-(4-fluorophenyl)pyridin-3-yl]-3-(4-piperidin-1-yl-butyl) urea (SEN34625/WYE-103914). J Med Chem 2010, 53 (11), 4379-89.
21. Horenstein, N. A.; Leonik, F. M.; Papke, R. L., Multiple pharmacophores for the selective activation of nicotinic alpha7-type acetylcholine receptors. Mol Pharmacol 2008, 74 (6), 1496-511.
22. Bunnelle, W. H.; Dart, M. J.; Schrimpf, M. R., Design of ligands for the nicotinic acetylcholine receptors: the quest for selectivity. Curr Top Med Chem 2004, 4 (3), 299-334.
23. Mazurov, A. A.; Speake, J. D.; Yohannes, D., Discovery and development of alpha7 nicotinic acetylcholine receptor modulators. J Med Chem 2011, 54 (23), 7943-61.
24. Grimster, N. P.; Stump, B.; Fotsing, J. R.; Weide, T.; Talley, T. T.; Yamauchi, J. G.; Nemecz, A.; Kim, C.; Ho, K. Y.; Sharpless, K. B.; Taylor, P.; Fokin, V. V., Generation of candidate ligands for nicotinic acetylcholine receptors via in situ click chemistry with a soluble acetylcholine binding protein template. J Am Chem Soc 2012, 134 (15), 6732-40.
25. Yamauchi, J. G.; Gomez, K.; Grimster, N.; Dufouil, M.; Nemecz, A.; Fotsing, J. R.; Ho, K. Y.; Talley, T. T.; Sharpless, K. B.; Fokin, V. V.; Taylor, P., Synthesis of selective agonists for the alpha7 nicotinic acetylcholine receptor with in situ click-chemistry on acetylcholine-binding protein templates. Mol Pharmacol 2012, 82 (4), 687-99.
26. Hein, C. D.; Liu, X. M.; Wang, D., Click chemistry, a powerful tool for pharmaceutical sciences. Pharm Res 2008, 25 (10), 2216-30.
27. Leonik, F. M.; Papke, R. L.; Horenstein, N. A., Quinuclidines as selective agonists for alpha-7 nicotinic acetylcholine receptors. Bioorg Med Chem Lett 2007, 17 (6), 1520-2.
28. Md Tohid, S. F.; Ziedan, N. I.; Stefanelli, F.; Fogli, S.; Westwell, A. D., Synthesis and evaluation of indole-containing 3,5-diarylisoxazoles as potential pro-apoptotic antitumour agents. Eur J Med Chem 2012, 56, 263-70.
29. Yamauchi, J. G.; Nemecz, A.; Nguyen, Q. T.; Muller, A.; Schroeder, L. F.; Talley, T. T.; Lindstrom, J.; Kleinfeld, D.; Taylor, P., Characterizing ligand-gated ion channel receptors with genetically encoded Ca2++ sensors. PLoS One 2011, 6 (1), e16519.
30. Huang, X.; Zheng, F.; Chen, X.; Crooks, P. A.; Dwoskin, L. P.; Zhan, C. G., Modeling subtype-selective agonists binding with alpha4beta2 and alpha7 nicotinic acetylcholine receptors: effects of local binding and long-range electrostatic interactions. J Med Chem 2006, 49 (26), 7661-74.
31. Yamauchi, J. G., Approaches in developing selective pharmacological lead compounds for the alpha7 nicotinic acetylcholine receptor with click-chemistry. Ph.D. Dissertation, University of California, San Diego, Calif. 2012.
32. Beckmann, H. S.; Wittmann, V., One-pot procedure for diazo transfer and azide-alkyne cycloaddition: triazole linkages from amines. Org Lett 2007, 9 (1), 1-4.
33. Coppo, F., Teen; Maskell, E., S. L.; Redshaw, S.; Skidmore, J.; Ward, R., William; Wilson, D., Matthew, 2-phenyl-5-amino-1,3,4-oxadiazoles and their use as nicotinic acetylcholine receptor ligands. European patent WO2007138033 2007.
34. Suzuki, T.; Ota, Y.; Ri, M.; Bando, M.; Gotoh, A.; Itoh, Y.; Tsumoto, H.; Tatum, P. R.; Mizukami, T.; Nakagawa, H.; Iida, S.; Ueda, R.; Shirahige, K.; Miyata, N., Rapid discovery of highly potent and selective inhibitors of histone deacetylase 8 using click chemistry to generate candidate libraries. J Med Chem 2012, 55 (22), 9562-75.
35. Dimitrov, I.; Jankova, K.; Hvilsted, S., Synthesis of polystyrene-based random copolymers with balanced number of basic or acidic functional groups. Journal of Polymer Science Part A: Polymer Chemistry 2010, 48 (9), 2044-2052.

References—Example 2

1. Mariani, E.; Monastero, R.; Mecocci, P., Mild cognitive impairment: a systematic review. *J Alzheimers Dis* 2007, 12 (1), 23-35.
2. Holtzman, D. M.; Morris, J. C.; Goate, A. M., Alzheimer's disease: the challenge of the second century. *Sci Transl Med* 2011, 3 (77), 77sr1.
3. Schliebs, R.; Arendt, T., The significance of the cholinergic system in the brain during aging and in Alzheimer's disease. *J Neural Transm* 2006, 113 (11), 1625-44.
4. Auld, D. S.; Kornecook, T. J.; Bastianetto, S.; Quirion, R., Alzheimer's disease and the basal forebrain cholinergic system: relations to beta-amyloid peptides, cognition, and treatment strategies. *Prog Neurobiol* 2002, 68 (3), 209-45.
5. Banerjee, C.; Nyengaard, J. R.; Wevers, A.; de Vos, R. A.; Jansen Steur, E. N.; Lindstrom, J.; Pilz, K.; Nowacki, S.; Bloch, W.; Schroder, H., Cellular expression of alpha7 nicotinic acetylcholine receptor protein in the temporal cortex in Alzheimer's and Parkinson's disease—a stereological approach. *Neurobiol Dis* 2000, 7 (6 Pt B), 666-72.
6. Jensen, A. A.; Frolund, B.; Liljefors, T.; Krogsgaard-Larsen, P., Neuronal nicotinic acetylcholine receptors: structural revelations, target identifications, and therapeutic inspirations. *J. Med Chem* 2005, 48 (15), 4705-45.
7. Gotti, C.; Clementi, F., Neuronal nicotinic receptors: from structure to pathology. *Prog Neurobiol* 2004, 74 (6), 363-96.
8. Lippiello, P.; Bencherif, M.; Hauser, T.; Jordan, K.; Letchworth, S.; Mazurov, A., Nicotinic receptors as targets for therapeutic discovery. *Expert Opin Drug Discov* 2007, 2 (9), 1185-1203.
9. Lindstrom, J. M., Nicotinic acetylcholine receptors of muscles and nerves: comparison of their structures, functional roles, and vulnerability to pathology. *Ann NY Acad Sci* 2003, 998, 41-52.
10. Gotti, C.; Clementi, F.; Fornari, A.; Gaimarri, A.; Guiducci, S.; Manfredi, I.; Moretti, M.; Pedrazzi, P.; Pucci, L.; Zoli, M., Structural and functional diversity of native brain neuronal nicotinic receptors. *Biochem Pharmacol* 2009, 78 (7), 703-11.
11. Rubboli, F.; Court, J. A.; Sala, C.; Morris, C.; Chini, B.; Perry, E.; Clementi, F., Distribution of nicotinic receptors in the human hippocampus and thalamus. *Eur J Neurosci* 1994, 6 (10), 1596-604.
12. Redrobe, J. P.; Nielsen, E. O.; Christensen, J. K.; Peters, D.; Timmermann, D. B.; Olsen, G. M., Alpha7 nicotinic acetylcholine receptor activation ameliorates scopolamine-induced behavioural changes in a modified continuous Y-maze task in mice. *Eur J Pharmacol* 2009, 602 (1), 58-65.
13. Vicens, P.; Ribes, D.; Torrente, M.; Domingo, J. L., Behavioral effects of PNU-282987, an alpha7 nicotinic receptor agonist, in mice. *Behav Brain Res* 2011, 216 (1), 341-8.
14. Pandya, A. A.; Yakel, J. L., Activation of the alpha7 nicotinic ACh receptor induces anxiogenic effects in rats which is blocked by a 5-HT(1)a receptor antagonist. *Neuropharmacology* 2013, 70, 35-42.
15. Roncarati, R.; Scali, C.; Comery, T. A.; Grauer, S. M.; Aschmi, S.; Bothmann, H.; Jow, B.; Kowal, D.; Gianfriddo, M.; Kelley, C.; Zanelli, U.; Ghiron, C.; Haydar, S.; Dunlop, J.; Terstappen, G. C., Procognitive and neuroprotective activity of a novel alpha7 nicotinic acetylcholine receptor agonist for treatment of neurodegenerative and cognitive disorders. *J Pharmacol Exp Ther* 2009, 329 (2), 459-68.
16. Pichat, P.; Bergis, O. E.; Terranova, J. P.; Urani, A.; Duarte, C.; Santucci, V.; Gueudet, C.; Voltz, C.; Steinberg, R.; Stemmelin, J.; Oury-Donat, F.; Avenet, P.; Griebel, G.; Scatton, B., SSR180711, a novel selective alpha7 nicotinic receptor partial agonist: (II) efficacy in experimental models predictive of activity against cognitive symptoms of schizophrenia. *Neuropsychopharmacology* 2007, 32 (1), 17-34.
17. Prickaerts, J.; van Goethem, N. P.; Chesworth, R.; Shapiro, G.; Boess, F. G.; Methfessel, C.; Reneerkens, O. A.; Flood, D. G.; Hilt, D.; Gawryl, M.; Bertrand, S.; Bertrand, D.; Konig, G., EVP-6124, a novel and selective alpha7 nicotinic acetylcholine receptor partial agonist, improves memory performance by potentiating the acetylcholine response of alpha7 nicotinic acetylcholine receptors. *Neuropharmacology* 2012, 62 (2), 1099-110.
18. Boess, F. G.; de Vry, J.; Erb, C.; Flessner, T.; Hendrix, M.; Luithle, J.; Methfessel, C.; Schnizler, K.; van der Staay, F. J.; van Kampen, M.; Wiese, W. B.; Konig, G., Pharmacological and behavioral profile of N-[(3R)-1-azabicyclo[2.2.2]oct-3-yl]-6-chinolincarboxamide (EVP-5141), a novel alpha7 nicotinic acetylcholine receptor agonist/serotonin 5-HT3 receptor antagonist. *Psychopharmacology (Berl)* 2013, 227 (1), 1-17.
19. Thomsen, M. S.; Hansen, H. H.; Timmerman, D. B.; Mikkelsen, J. D., Cognitive improvement by activation of alpha7 nicotinic acetylcholine receptors: from animal models to human pathophysiology. *Curr Pharm Des* 2010, 16 (3), 323-43.
20. Wallace, T. L.; Ballard, T. M.; Pouzet, B.; Riedel, W. J.; Wettstein, J. G., Drug targets for cognitive enhancement in neuropsychiatric disorders. *Pharmacol Biochem Behav* 2011, 99 (2), 130-45.
21. Lendvai, B.; Kassai, F.; Szajli, A.; Nemethy, Z., alpha7 nicotinic acetylcholine receptors and their role in cognition. *Brain Res Bull* 2013, 93, 86-96.
22. Arunrungvichian, K.; Fokin, V. V.; Vajragupta, O.; Taylor, P., Selectivity optimization of substituted 1,2,3-triazoles as α7 nicotinic acetylcholine receptor agonists Submitted companion manuscript.
23. Falsafi, S. K.; Deli, A.; Hoger, H.; Pollak, A.; Lubec, G., Scopolamine administration modulates muscarinic, nicotinic and NMDA receptor systems. *PLoS One* 2012, 7 (2), e32082.
24. Decker, M. W.; McGaugh, J. L., The role of interactions between the cholinergic system and other neuromodulatory systems in learning and memory. *Synapse* 1991, 7 (2), 151-68.
25. Dellu, F.; Contarino, A.; Simon, H.; Koob, G. F.; Gold, L. H., Genetic differences in response to novelty and spatial memory using a two-trial recognition task in mice. *Neurobiol Learn Mem* 2000, 73 (1), 31-48.
26. Ennaceur, A.; Delacour, J., A new one-trial test for neurobiological studies of memory in rats. 1: Behavioral data. *Behav Brain Res* 1988, 31 (1), 47-59.
27. Morris, R., Developments of a water-maze procedure for studying spatial learning in the rat. *J Neurosci Methods* 1984, 11 (1), 47-60.
28. Lanni, C.; Lenzken, S. C.; Pascale, A.; Del Vecchio, I.; Racchi, M.; Pistoia, F.; Govoni, S., Cognition enhancers between treating and doping the mind. *Pharmacol Res* 2008, 57 (3), 196-213.

29. Small-Molecule Drug Discovery Suite 2014-3: QikProp, v., Schrödinger, LLC, New York, N.Y., 2014.
30. Rostkowski, M.; Spjuth, O.; Rydberg, P., WhichCyp: prediction of cytochromes P450 inhibition. *Bioinformatics* 2013, 29 (16), 2051-2.
31. Walker, D. P.; Wishka, D. G.; Piotrowski, D. W.; Jia, S.; Reitz, S. C.; Yates, K. M.; Myers, J. K.; Vetman, T. N.; Margolis, B. J.; Jacobsen, E. J.; Acker, B. A.; Groppi, V. E.; Wolfe, M. L.; Thornburgh, B. A.; Tinholt, P. M.; Cortes-Burgos, L. A.; Walters, R. R.; Hester, M. R.; Seest, E. P.; Dolak, L. A.; Han, F.; Olson, B. A.; Fitzgerald, L.; Staton, B. A.; Raub, T. J.; Hajos, M.; Hoffmann, W. E.; Li, K. S.; Higdon, N. R.; Wall, T. M.; Hurst, R. S.; Wong, E. H.; Rogers, B. N., Design, synthesis, structure-activity relationship, and in vivo activity of azabicyclic aryl amides as alpha7 nicotinic acetylcholine receptor agonists. *Bioorg Med Chem* 2006, 14 (24), 8219-48.
32. Schrödinger Release 2014-3: LigPrep, v., Schrödinger, LLC, New York, N.Y., 2014.

A number of embodiments have been described. Nevertheless, it will be understood that various modifications may be made without departing from the spirit and scope of the invention. Accordingly, other embodiments are within the scope of the following claims.

What is claimed is:

1. A method for:
    (a) treating
        a Central Nervous System (CNS) disorder involving an acetylcholine-mediated response;
    comprising:
    administering to a patient or an individual in need thereof, a compound, a compound having the formula:

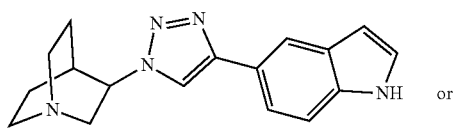

IND8 or

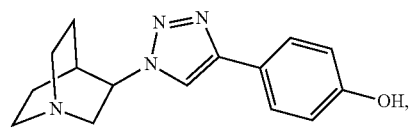

QND8 or (b) a stereoisomer or a pharmaceutically acceptable salt thereof.

2. The method of claim 1, wherein the compound or formulation is administered enterally.

3. The method of claim 1, wherein the compound or formulation is administered orally.

4. The method of claim 1, wherein the compound or formulation is administered parenterally.

5. The method of claim 1, wherein the compound or formulation is administered by inhalation spray.

6. The method of claim 1, wherein the compound or formulation is administered nasally.

7. The method of claim 1, wherein the compound or formulation is administered topically.

8. The method of claim 1, wherein the compound or formulation is administered intrathecally.

9. The method of claim 1, wherein the compound or formulation is administered intracerebrally.

10. The method of claim 1, wherein the compound or formulation is administered epidurally.

11. The method of claim 1, wherein the compound or formulation is administered intracranially.

12. The method of claim 1, wherein the compound or formulation is administered rectally.

* * * * *